(12) United States Patent
Beaumont et al.

(10) Patent No.: US 10,703,741 B2
(45) Date of Patent: Jul. 7, 2020

(54) COVALENT INHIBITORS OF PAD4

(71) Applicant: Padlock Therapeutics, Inc., Princeton, NJ (US)

(72) Inventors: Edward Jean Beaumont, Abingdon (GB); Rajesh Devraj, Chesterfield, MO (US); Philip Stephen Kerry, Abingdon (GB); Gnanasambandam Kumaravel, Lexington, MA (US); Pui Leng Loke, Abingdon (GB); Mirco Meniconi, Abingdon (GB); Jordan John Palfrey, Abingdon (GB); Carl North, Abingdon (GB); Cristina Lecci, Abingdon (GB); Heather Tye, Abingdon (GB)

(73) Assignee: Padlock Therapeutics, Inc., Princeton, NJ (US)

( * ) Notice: Subject to any disclaimer, the term of this patent is extended or adjusted under 35 U.S.C. 154(b) by 0 days.

(21) Appl. No.: 16/319,006

(22) PCT Filed: Jul. 27, 2017

(86) PCT No.: PCT/US2017/044194
§ 371 (c)(1),
(2) Date: Jan. 18, 2019

(87) PCT Pub. No.: WO2018/022897
PCT Pub. Date: Feb. 1, 2018

(65) Prior Publication Data
US 2019/0276432 A1    Sep. 12, 2019

Related U.S. Application Data

(60) Provisional application No. 62/367,389, filed on Jul. 27, 2016.

(51) Int. Cl.
*A61K 31/44* (2006.01)
*C07D 401/14* (2006.01)
*C07D 471/04* (2006.01)
*A61K 45/06* (2006.01)

(52) U.S. Cl.
CPC ......... *C07D 401/14* (2013.01); *C07D 471/04* (2013.01); *A61K 45/06* (2013.01)

(58) Field of Classification Search
CPC .... C07D 401/14; C07D 471/04; A61K 45/06; A61K 31/4545; A61K 31/437; A61K 31/4184; A61P 35/00; A61P 35/02; A61P 31/18; A61P 17/00; A61P 9/00; A61P 3/00; A61P 37/00
USPC ...................................................... 514/300
See application file for complete search history.

(56) References Cited

FOREIGN PATENT DOCUMENTS

| WO | WO2014015905 A1 | 1/2014 |
| WO | WO2016185279 A1 | 11/2016 |
| WO | WO2017/100601 A1 | 6/2017 |
| WO | WO2017/100594 A1 | 7/2017 |
| WO | WO2017147102 A1 | 8/2017 |
| WO | WO2018049296 A1 | 3/2018 |

OTHER PUBLICATIONS

Berge et al., "Pharmaceutical Salts", Journal of Pharmaceutical Sciences, vol. 66(1), pp. 1-19 (1977).
Brinkmann et al., "Neutrophil extracellular traps kill bacteria", Science vol. 303(5663) pp. 1532-1535 ( 2004).
Chang, et al., "Increased PADI4 expression in blood and tissues of patients with malignant tumors", BMC Cancer, vol. 9(40), pp. 1-11 (2009).
Chumanevich, et al., "Suppression of colitis in mice by Cl-amidine: a novel peptidylarginine deiminase inhibitor", American J of Physiology, Gastrointestinal and Liver Physiology, vol. 300(6), pp. G929-G938 (2011).
Clark, et al., "Platelet TLR4 activates neutrophil extracellular traps to ensnare bacteria in septic blood", Nature Medicine, vol. 13(4), pp. 463-469 (2007).
Dworski et al., "Eosinophil and neutrophil extracellular DNA traps in human allergic asthmatic airways", The Journal of Allergy and Clinical Immunology, vol. 127(5), pp. 1260-1266 (2011).
Fuchs, et al., "Extracellular DNA traps promote thrombosis", PNAS, vol. 107(36), pp. 15880-15885 (2010).
Hakkim et al., "Impairment of neutrophil extracellular trap degradation is associated with lupus nephritis", PNAS, vol. 107(21), pp. 9813-9818 (2010).
ISR issued by USPTO for Application No. PCT/US2016/065857 dated Apr. 17, 2017 (10 pages).
Jones et al., "Protein arginine deiminase 4 (PAD4): current understanding and future therapeutic potential", Current Opinion in Drug Discovery & Development, vol. 12(5), pp. 616-627 (2009).

(Continued)

*Primary Examiner* — Taylor V Oh
(74) *Attorney, Agent, or Firm* — Hong Liu

(57) ABSTRACT

The present invention provides compounds of formula I useful as inhibitors of PAD4, compositions thereof, and methods of treating PAD4-related disorders.

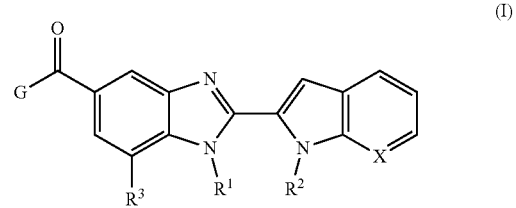

13 Claims, No Drawings

(56) References Cited

OTHER PUBLICATIONS

Kessenbrock et al., "Netting neutrophils in autoimmune small-vessel vasculitis", Nature Medicine, vol. 15(6), pp. 623-625 (2009).
Kochi et al., "PADI4 polymorphism predisposes male smokers to rheumatoid arthritis", Annals of the Rheumatic Diseases, vol. 70(3), pp. 512-515 (2011).
Lange et al., "Protein deiminases: New players in the developmentally regulated loss of neutral regenerative ability", Developmental Biology, vol. 355(2), 205-214 (2011).
Lewis et al., "Inhibition of PAD4 activity is sufficient to disrupt mouse and human NET formation", Nature Chemical Lewis Biology, vol. 11(3) pp. 189-191 (2015).
Li et al., "PAD4 is essential for antibacterial innate immunity mediated by neutrophil extracellular traps", JEM, vol. 207(9), pp. 1853-1862 (2010).
Li et al., "Regulation of p53 Target Gene Expression by Peptidylarginine Deiminase 4", Molecular and Cellular Biology, vol. 28(15), pp. 4745-4758 (2008).
Lin et al., "Mast Cells and Neutrophils Release IL-17 through Extracellular Trip Formation in Psoriasis", The Journal of Immunology, vol. 187(1), pp. 490-500 (2011).
Neeli et al., "Histone Deimination As a Response to Inflammatory Stimuli in Neutrophils", The Journal of Immunology, vol. 108(3), pp. 1895-1902 (2008).
Pubchem, "Substance Record for SID 1730220505," retrieved from http://pubchem.ncbi.nim.nih.gov/substance/173022050#section=Top accessed on Mar. 24, 2018 (5 pages).
Savchenko et al., "Long pentraxin 3 (PTX3) expression and release by neutrophils in nitro and in ulcerative colitis".
Slack et al., "Protein Arginine Deiminase 4: a target for an epigenetic cancer therapy", Cellular and Molecular Life Sciences, vol. 68(4), pp. 709-720 (2011).
Villanueva et al., "Netting Neutrophils Induce Endothelial Damage, Infiltrate Tissues, and Expose Immunostimulatory Molecules in Systemic Lupus Erythematosus", The Journal of Immunology, vol. 187(1), pp. 538-552 (2011).
Vitkov et al., "Neutrophil Fate in Gingival Crevicular Fluid", Ultrastructrual Pathology, vol. 34(1), pp. 1-6 (2010).
Wegner et al., "Autoimmunity to specific citrullinated proteins gives the first clues to the etiology of rheumatoid arthritis", Immunological Reviews, vol. 233(1), pp. 34-54 (2010).
Willis et al., "N-a-Benzoyl-N5-(2-Chloro-1-Iminoethyl)-L-Ornithine Amide, a Protein Arginine Deiminase Inhibitor, Reduces the Severity of Murine Collagen-Induced Arthritis", The J. of Immunology, vol. 186(7), pp. 4396-4404 (2011).

COVALENT INHIBITORS OF PAD4

This application is a 371 of International Application No. PCT/US2017/044194, filed on Jul. 27, 2017, which claims benefit of 62/367,389, filed on Jul. 27, 2016.

BACKGROUND OF THE INVENTION

PAD4 is a member of the peptidylarginine deiminase (PAD) family of enzymes capable of catalysing the citrullination of arginine into citrulline within peptide sequences. PAD4 is responsible for the deimination or citrullination of a variety of proteins in vitro and in vivo, with consequences of diverse functional responses in a variety of diseases (Jones J. E. et al, Curr. Opin. Drug Discov. Devel., 12(5), (2009), 616-627). Examples of exemplar diseases include rheumatoid arthritis, diseases with neutrophilic contributions to pathogenesis (for example vasculitis, systemic lupus erythematosus, ulcerative colitis) in addition to oncology indications. PAD4 inhibitors also have wider applicability as tools and therapeutics for human disease through epigenetic mechanisms.

Inhibitors of PAD4 have utility against Rheumatoid Arthritis (RA). RA is an auto-immune disease affecting approximately 1% of the population (Wegner N. et al, Immunol. Rev., 233(1) (2010), 34-54). It is characterised by inflammation of articular joints leading to debilitating destruction of bone and cartilage. A weak genetic association between PAD4 polymorphisms and susceptibility to RA has been suggested, albeit inconsistently, in a number of population studies (Kochi Y. et al, Ann. Rheum. Dis., 70, (2011), 512-515). PAD4 (along with family member PAD2) has been detected in synovial tissue where it is responsible for the deimination of a variety of joint proteins. This process is presumed to lead to a break of tolerance to, and initiation of immune responses to, citrullinated substrates such as fibrinogen, vimentin and collagen in RA joints. These anti-citrullinated protein antibodies (ACPA) contribute to disease pathogenesis and may also be used as a diagnostic test for RA (e.g. the commercially available CCP2 or cyclic citrullinated protein 2 test). In addition, increased citrullination may also offer additional direct contributions to disease pathogenesis through its ability to affect directly the function of several joint and inflammatory mediators (e.g. fibrinogen, anti-thrombin, multiple chemokines). In a smaller subset of RA patients, anti-PAD4 antibodies can be measured and may correlate with a more erosive form of the disease.

PAD4 inhibitors are also useful for the reduction of pathological neutrophil activity in a variety of diseases. Studies suggest that the process of Neutrophil Extracellular Trap (NET) formation, an innate defence mechanism by which neutrophils are able to immobilise and kill pathogens, is associated with histone citrulllination and is deficient in PAD4 knockout mice (Neeli I. et al, J. Immunol., 180, (2008), 1895-1902 and Li P. et al, J. Exp. Med., 207(9), (2010), 1853-1862). PAD4 inhibitors may therefore have applicability for diseases where NET formation in tissues contributes to local injury and disease pathology. Such diseases include, but are not limited to, small vessel vasculitis (Kessenbrock K. et al, Nat. Med., 15(6), (2009), 623-625), systemic lupus erythematosus (Hakkim A. et al, Proc. Natl. Acad. Sci. USA, 107(21), (2010), 9813-9818 and Villanueva E. et al, J. Immunol., 187(1), (2011), 538-52), ulcerative colitis (Savchenko A. et al, Pathol. Int., 61(5), (2011), 290-7), cystic fibrosis, asthma (Dworski R. et al, J. Allergy Clin. Immunol., 127(5), (2011), 1260-6), deep vein thrombosis (Fuchs T et al, Proc. Natl. Acad. Sci. USA, 107(36), (2010), 15880-5), periodontitis (Vitkov L. et al, Ultrastructural Pathol., 34(1), (2010), 25-30), sepsis (Clark S. R. et al, Nat. Med., 13(4), (2007), 463-9), appendicitis (Brinkmann V. et al, Science, 303, (2004), 1532-5), and stroke. In addition, there is evidence that NETs may contribute to pathology in diseases affecting the skin, eg in cutaneous lupus erythematosis (Villanueva E. et al, J. Immunol., 187(1), (2011), 538-52) and psoriasis (Lin A. M et al., J. Immunol., 187(1), (2011), 490-500), so a PAD4 inhibitor may show benefit to tackle NET skin diseases, when administered by a systemic or cutaneous route. PAD4 inhibitors may affect additional functions within neutrophils and have wider applicability to neutrophilic diseases.

Studies have demonstrated efficacy of tool PAD inhibitors (for example chloro-amidine) in a number of animal models of disease, including collagen-induced arthritis (Willis VC. et al, J. Immunol., 186(7), (2011), 4396-4404), dextran sulfate sodium (DSS)-induced experimental colitis (Chumanevich A. A. et al, Am. J. Physiol. Gastrointest. Liver Physiol., 300(6), (2011), G929-G938), spinal cord repair (Lange S. et al, Dev. Biol., 355(2), (2011), 205-14), and experimental autoimmune encephalomyelitis (EAE). The DSS colitis report also demonstrates that chloro-amidine drives apoptosis of inflammatory cells both in vitro and in vivo, suggesting that PAD4 inhibitors may be effective more generally in widespread inflammatory diseases.

PAD4 inhibitors are also useful in the treatment of cancers (Slack. J. L. et al, Cell. Mol. Life Sci., 68(4), (2011), 709-720). Over-expression of PAD4 has been demonstrated in numerous cancers (Chang X. et al, BMC Cancer, 9, (2009), 40). An anti-proliferative role has been suggested for PAD4 inhibitors from the observation that PAD4 citrullinates arginine residues in histones at the promoters of p53-target genes such as p21, which are involved in cell cycle arrest and induction of apoptosis (Li P. et al, Mol. Cell Biol., 28(15), (2008), 4745-4758).

The aforementioned role of PAD4 in deiminating arginine residues in histones may be indicative of a role for PAD4 in epigenetic regulation of gene expression. PAD4 is the primary PAD family member observed to be resident in the nucleus as well as the cytoplasm. Early evidence that PAD4 may act as a histone demethyliminase as well as a deiminase is inconsistent and unproven. However, it may reduce histone arginine methylation (and hence epigenetic regulation associated with this mark) indirectly via depletion of available arginine residues by conversion to citrulline. PAD4 inhibitors are useful as epigenetic tools or therapeutics for affecting expression of varied target genes in additional disease settings. Through such mechanisms, PAD4 inhibitors may also be effective in controlling citrullination levels in stem cells and may therefore therapeutically affect the pluripotency status and differentiation potential of diverse stem cells including, but not limited to, embryonic stem cells, neural stem cells, haematopoietic stem cells and cancer stem cells. Accordingly, there remains an unmet need to identify and develop PAD4 inhibitors for the treatment of PAD4-mediated disorders.

SUMMARY OF THE INVENTION

It has now been found that compounds of formula I are useful as inhibitors of PAD4:

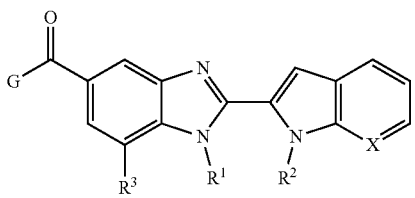

I or a pharmaceutically acceptable salt thereof, wherein each of G, $R^1$, $R^2$, $R^3$ and X is as defined and described herein.

In some embodiments, a provided compound demonstrates selectivity for PAD4 with respect to PAD2. The present invention also provides pharmaceutically acceptable compositions comprising a provided compound. Provided compounds are useful in treatment of various disorders associated with PAD4. Such disorders are described in detail, herein, and include, for example rheumatoid arthritis, vasculitis, systemic lupus erythematosus, ulcerative colitis, cancer, cystic fibrosis, asthma, cutaneous lupus erythematosis, and psoriasis.

DETAILED DESCRIPTION OF THE INVENTION

1. General Description of Certain Aspects of the Invention

In some embodiments, such compounds include those of the formulae described herein, or a pharmaceutically acceptable salt thereof, wherein each variable is as defined herein and described in embodiments. Such compounds have the structure of formula I:

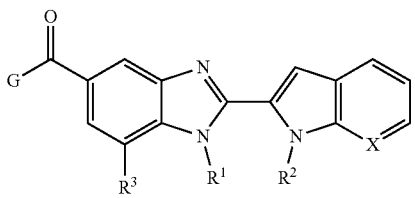

I or a pharmaceutically acceptable salt thereof, wherein:
G is

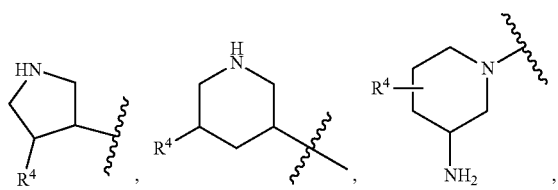

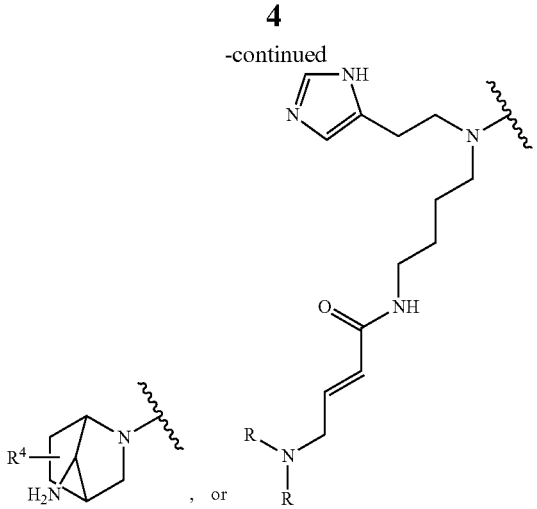

each $R^4$ is independently selected from

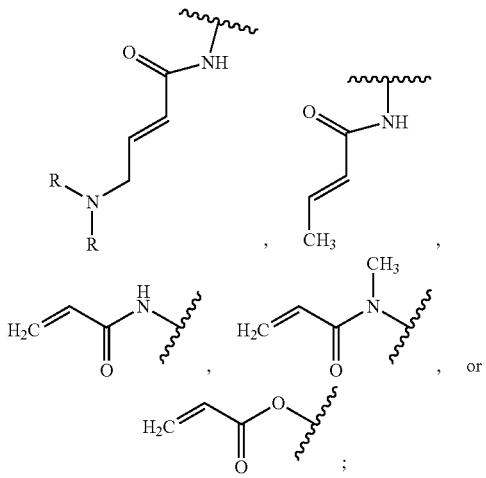

$R^1$ is hydrogen or $C_{1-6}$ aliphatic;
$R^2$ is hydrogen or $C_{1-10}$ aliphatic;
X is selected from N or CH;
$R^3$ is —R, or —OR; and
each R is independently hydrogen or $C_{1-6}$ aliphatic optionally substituted with 1-3 fluorine atoms.

2. Definitions

Compounds of the present invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}C$- or $^{14}C$-enriched carbon are within the scope of this invention. Such compounds are useful, for example, as analytical tools, as probes in biological assays, or as therapeutic agents in accordance with the present invention.

The terms "measurable affinity" and "measurably inhibit," as used herein, means a measurable change in PAD4 activity between a sample comprising a compound of the present invention, or composition thereof, and PAD4, and an equivalent sample comprising PAD4 in the absence of said compound, or composition thereof.

3. Description of Exemplary Compounds

According to one aspect, the present invention provides a compound of formula I:

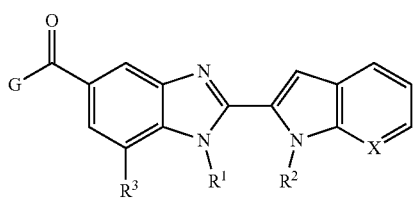

or a pharmaceutically acceptable salt thereof, wherein:

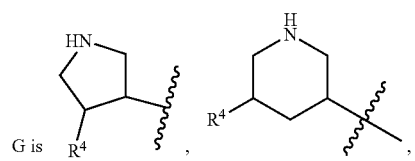

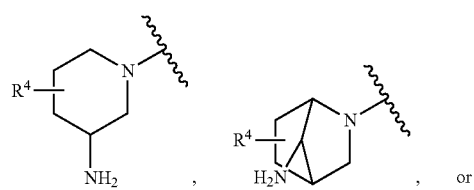

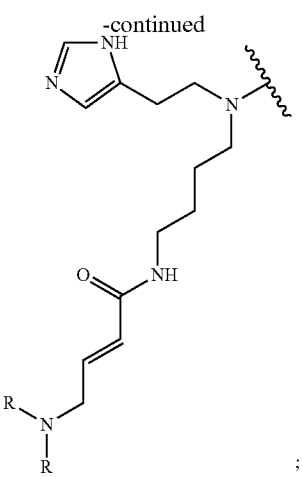

each R⁴ is independently selected from

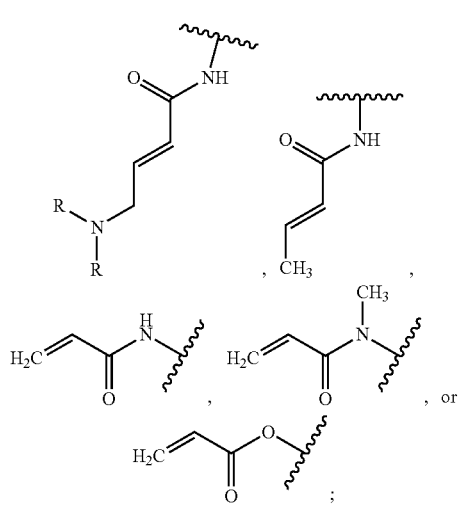

$R^1$ is hydrogen or $C_{1-6}$ aliphatic;

$R^2$ is hydrogen or $C_{1-10}$ aliphatic;

X is selected from N or CH;

$R^3$ is —R, or —OR; and each R is independently hydrogen or $C_{1-6}$ aliphatic optionally substituted with 1-3 fluorine atoms.

As defined above and described herein, $R^1$ is hydrogen, or $C_{1-6}$ aliphatic. In some embodiments, $R^1$ is hydrogen. In some embodiments, $R^1$ is $C_{1-6}$ aliphatic. In some embodiments, $R^1$ is methyl.

As defined above and described herein, $R^2$ is hydrogen or $C_{1-10}$ aliphatic. In some embodiments, $R^2$ is hydrogen. In some embodiments, $R^2$ is $C_{1-10}$ aliphatic. In some embodiments, $R^2$ is —CH₂-cyclopropyl.

In some embodiments, $R^3$ is —R or —OR. In some embodiments, $R^3$ is —R. In some embodiments, $R^3$ is —OR. In some embodiments, $R^3$ is hydrogen. In some embodiments, $R^3$ is —OCH₃.

As defined above and described herein, X is selected from N or CH. In some embodiments, X is N. In some embodiments, X is CH.

As defined above and described herein, G is

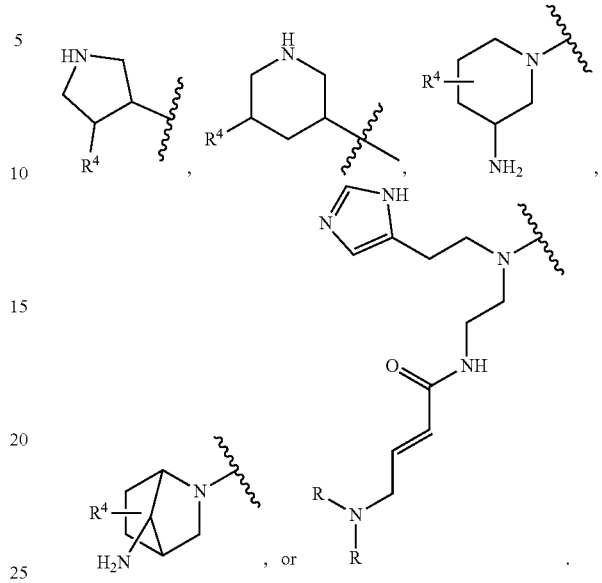

In some embodiments, G is

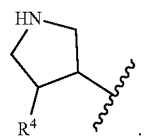

In some embodiments, G is

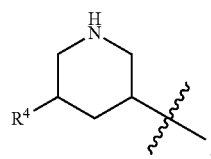

In other embodiments, G is

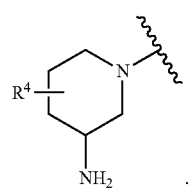

In some embodiments, G is

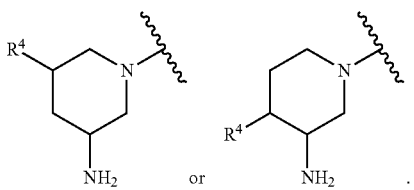

In some embodiments, G is
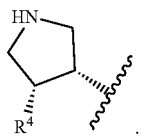
In other embodiments, G is
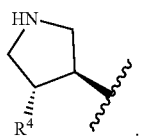
In certain embodiments, G is
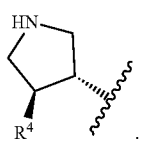
In some embodiments, G is
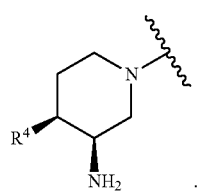
In other embodiments, G is
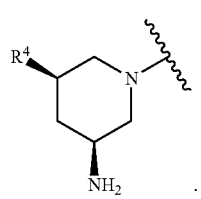
In certain embodiments, G is
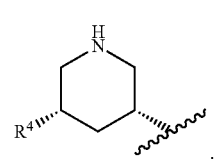
In some embodiments, G is
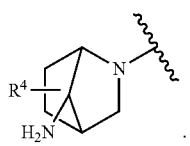
In some embodiments, G is R
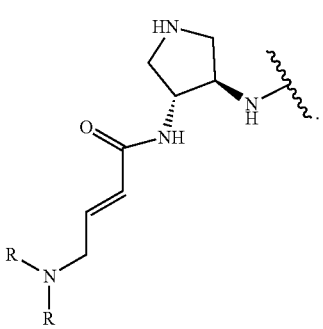
In some embodiments, G is
In some embodiments, G is In some embodiments, G is
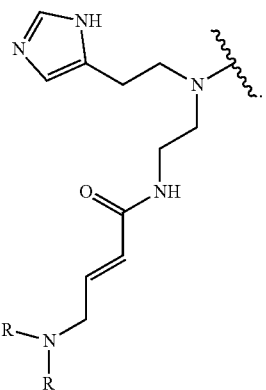
In some embodiments, G is
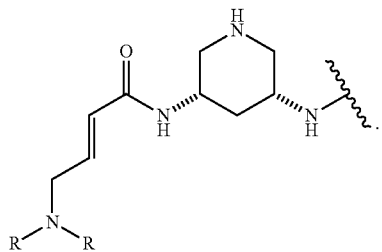
In some embodiments, G is
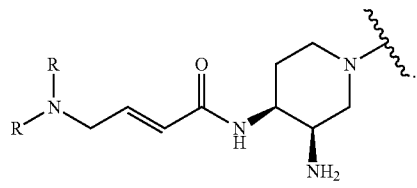
In some embodiments, G is
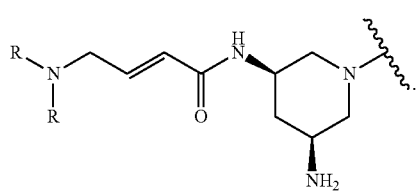
In some embodiments, G is
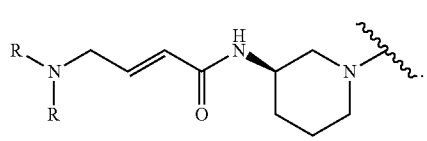
In some embodiments, G is selected from
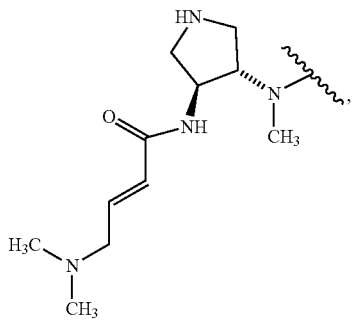 [SMILES: *N(C)[C@H]1CNC[C@@H]1NC(=O)/C=C/CN(C)C]
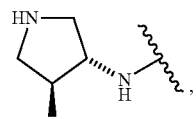
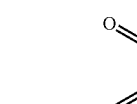
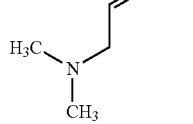
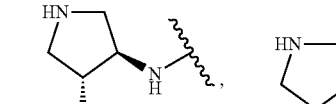
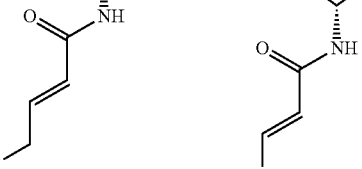
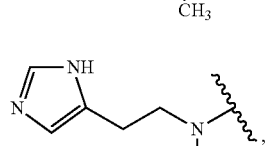
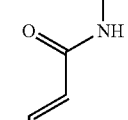
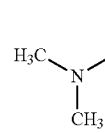
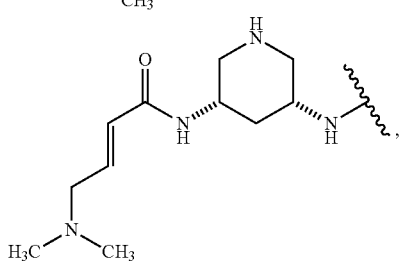

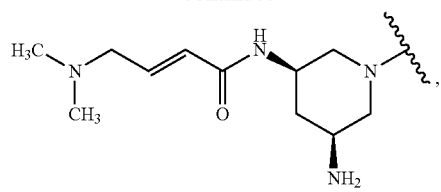
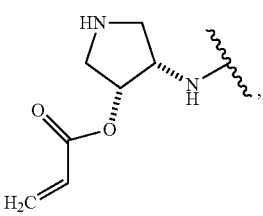
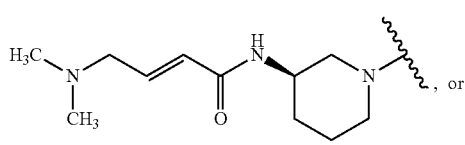
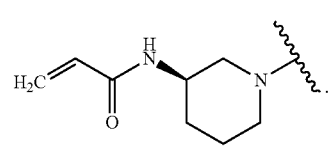
In some embodiments, G is
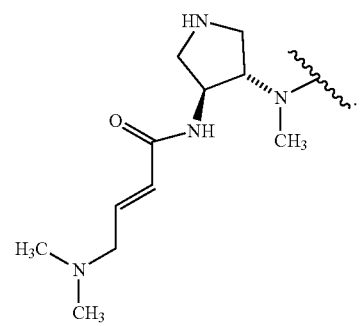 [SMILES: *N(C)[C@H]1CNC[C@@H]1NC(=O)/C=C/CN(C)C]
In some embodiments, G is
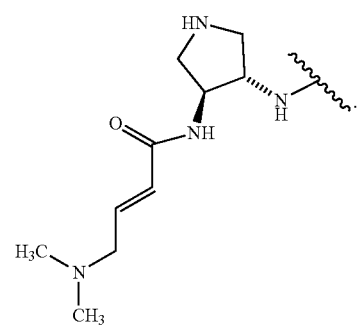 [SMILES: *N[C@H]1CNC[C@@H]1NC(=O)/C=C/CN(C)C]
In some embodiments, G is
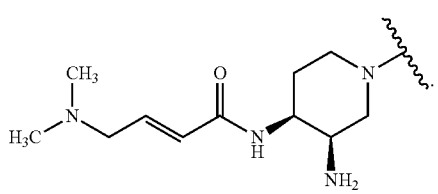 [SMILES: *N1CC[C@H](NC(=O)/C=C/CN(C)C)[C@H](N)C1]
In some embodiments, G is
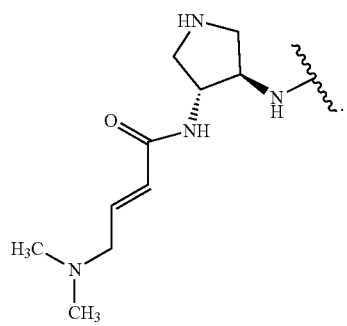 [SMILES: *N[C@@H]1CNC[C@H]1NC(=O)/C=C/CN(C)C]
In some embodiments, G is
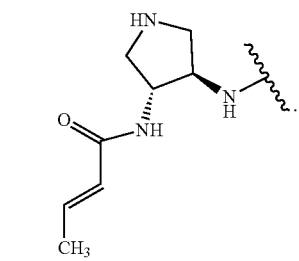 [SMILES: *N[C@@H]1CNC[C@H]1NC(=O)/C=C/C]
In some embodiments, G is
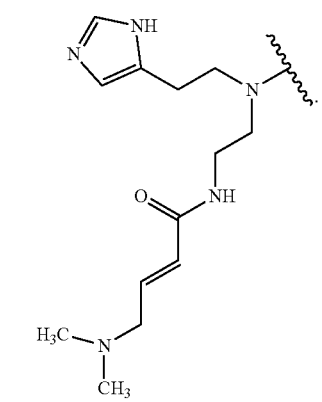 [SMILES: *N(CCNC(=O)/C=C/CN(C)C)CCc1cnc[nH]1]

In some embodiments, G is
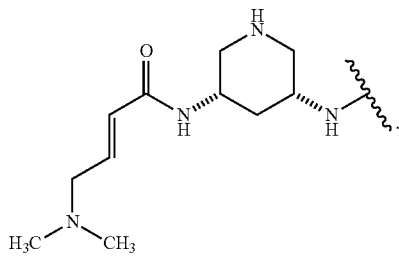
In some embodiments, G is
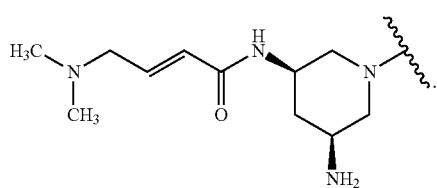 [SMILES: *N1C[C@@H](N)C[C@@H](NC(=O)/C=C/CN(C)C)C1]
In some embodiments, G is
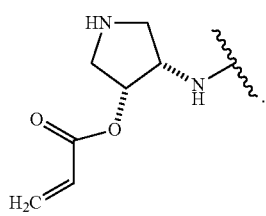 [SMILES: *N[C@H]1CNC[C@H]1OC(=O)C=C]
In some embodiments, G is
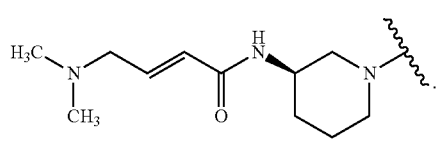 [SMILES: *N1CCC[C@@H](NC(=O)/C=C/CN(C)C)C1]
In some embodiments, G is
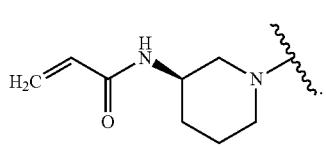 [SMILES: *N1CCC[C@@H](NC(=O)C=C)C1]
In some embodiments, G is
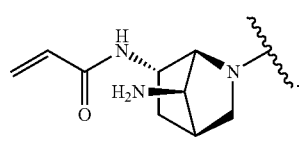 [SMILES: *N1C[C@H]2C[C@H](NC(=O)C=C)[C@@H]1[C@@H]2N]
In some embodiments, G is
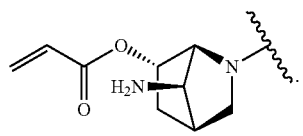 [SMILES: *N1C[C@H]2C[C@H](OC(=O)C=C)[C@@H]1[C@@H]2N]
In some embodiments, G is
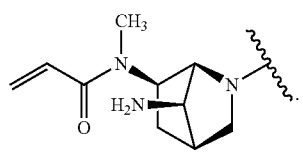 [SMILES: *N1C[C@H]2C[C@@H](N(C)C(=O)C=C)[C@@H]1[C@@H]2N]
In some embodiments, G is
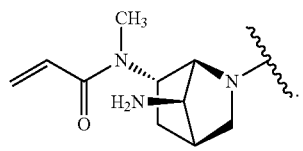 [SMILES: *N1C[C@H]2C[C@H](N(C)C(=O)C=C)[C@@H]1[C@@H]2N]
As defined above and described herein, each $R^4$ is independently selected from
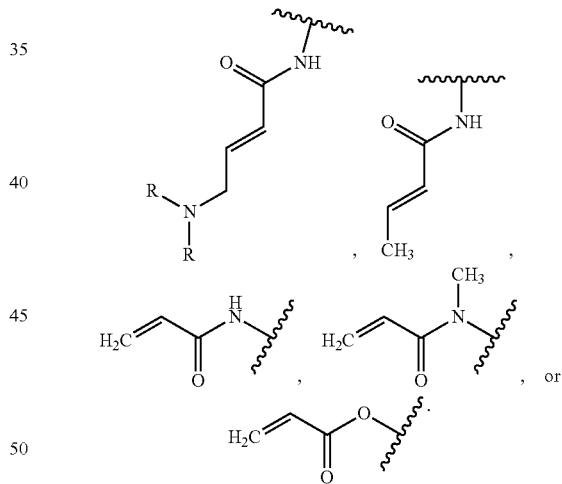
In some embodiments, $R^4$ is
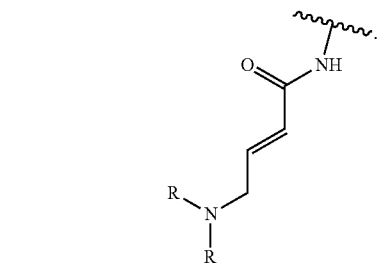

In some embodiments, R⁴ is
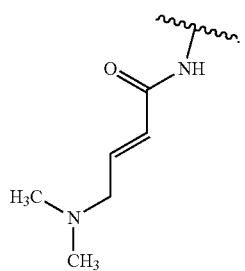 [SMILES: *NC(=O)/C=C/CN(C)C]
In some embodiments, R⁴ is
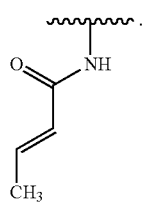
In some embodiments, R⁴ is
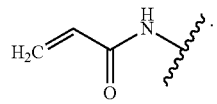
In some embodiments,
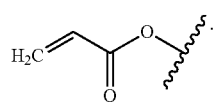
In some embodiments, R⁴ is
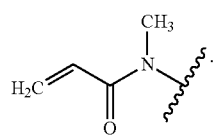
In some embodiments, the compound of formula I is selected from those depicted below in Table 1.
TABLE 1
Exemplary Compounds of Formula I TABLE 1-continued
Exemplary Compounds of Formula I
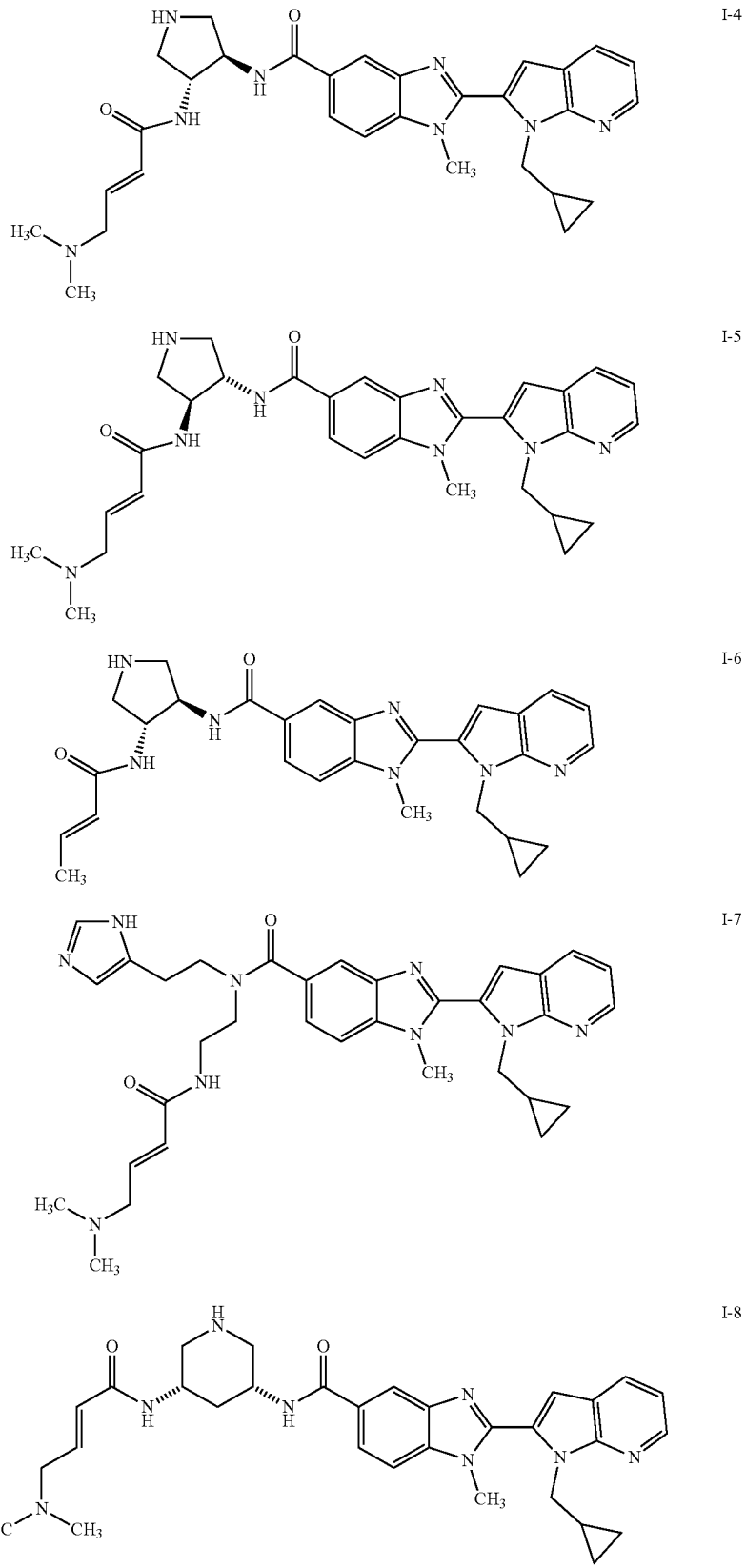

TABLE 1-continued
Exemplary Compounds of Formula I
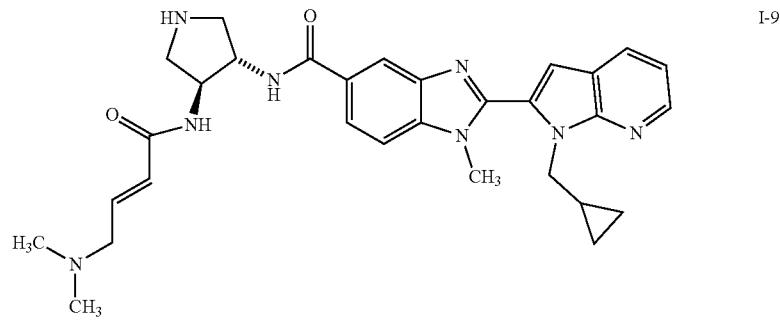
I-9
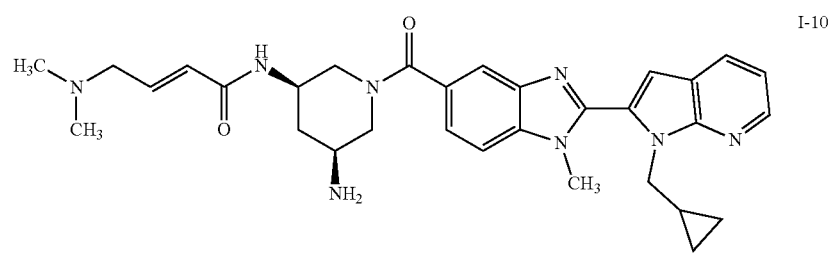
I-10
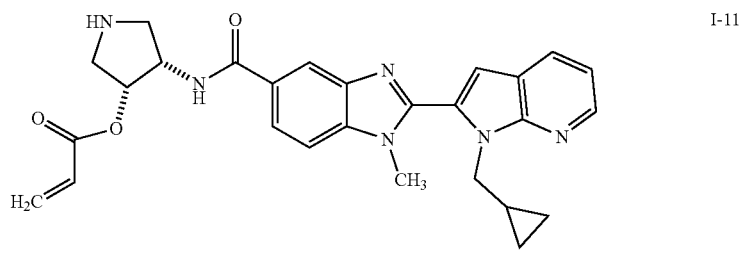
I-11
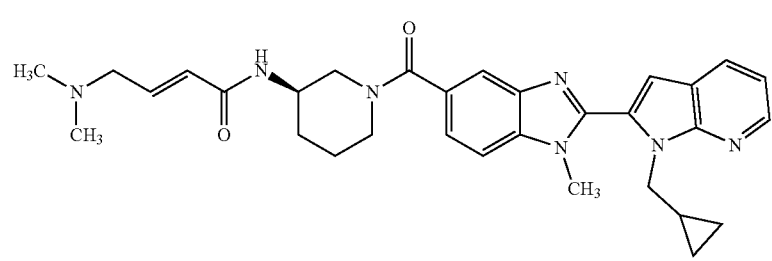 [SMILES: CN(C)C/C=C/C(=O)N[C@@H]1CCCN(C(=O)c2ccc3c(c2)nc(-c2cc4cccnc4n2CC2CC2)n3C)C1]
I-12
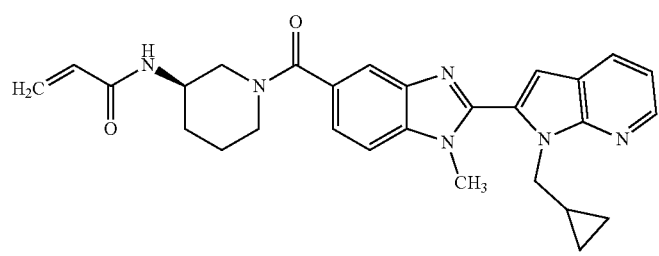 [SMILES: C=CC(=O)N[C@@H]1CCCN(C(=O)c2ccc3c(c2)nc(-c2cc4cccnc4n2CC2CC2)n3C)C1]
I-13

TABLE 1-continued

Exemplary Compounds of Formula I

I-14

I-15

I-16

I-17

In certain embodiments, the present invention provides any compound described above and herein, or a pharmaceutically acceptable salt thereof. In some embodiments, the present invention provides a compound as depicted in Table 1, above, or a pharmaceutically acceptable salt thereof.

In certain embodiments, the present invention provides a conjugate comprising PAD4 having a cysteine residue, Cys645, wherein the Cys645 is covalently, and irreversibly, bonded to an inhibitor described above and herein, such that inhibition of the PAD4 is maintained.

In certain embodiments, the present invention provides a conjugate of formula X:

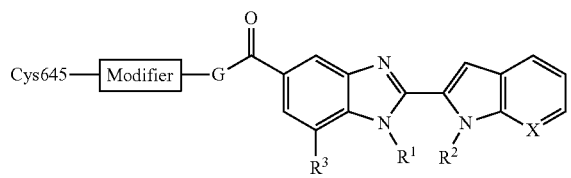

wherein:
Cys645 is cysteine 645 of PAD4;
Modifier is a bivalent group resulting from covalent bonding of a Warhead Group with the Cys645 of the PAD4; and
Warhead Group is a functional group on G capable of covalently binding to the Cys645 of the PAD4.

In some embodiments, the present invention provides a conjugate of formula X-a:

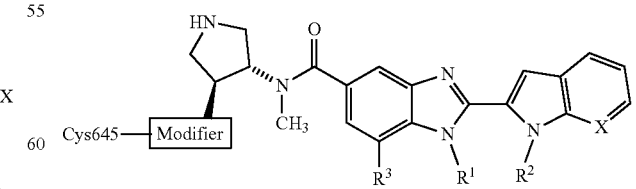

wherein each of Cys645, Modifier, $R^1$, $R^2$, $R^3$, and X is as defined above and described herein.

In some embodiments, the present invention provides a conjugate of formula X-b:

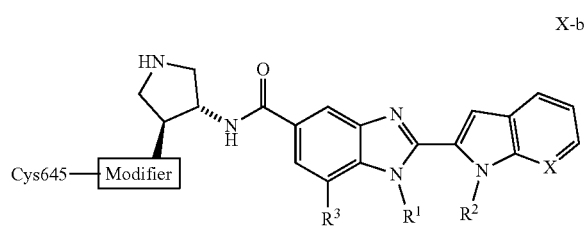

X-b wherein each of Cys645, Modifier, $R^1$, $R^2$, $R^3$, and X is as defined above and described herein.

In some embodiments, the present invention provides a conjugate of formula X-c:

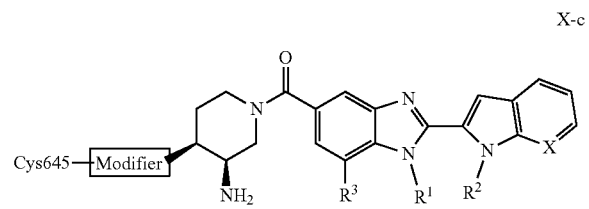

X-c wherein each of Cys645, Modifier, $R^1$, $R^2$, $R^3$, and X is as defined above and described herein.

In some embodiments, the present invention provides a conjugate of formula X-d:

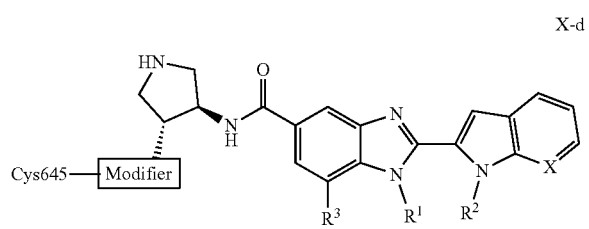

X-d wherein each of Cys645, Modifier, $R^1$, $R^2$, $R^3$, and X is as defined above and described herein.

In some embodiments, the present invention provides a conjugate of formula X-e:

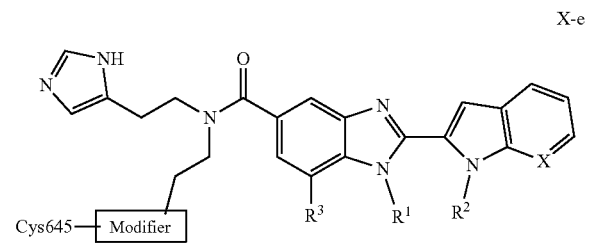

X-e wherein each of Cys645, Modifier, $R^1$, $R^2$, $R^3$, and X is as defined above and described herein.

In some embodiments, the present invention provides a conjugate of formula X-f:

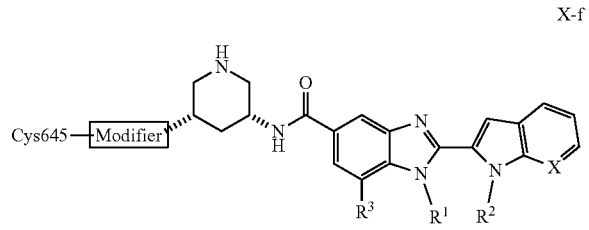

X-f wherein each of Cys645, Modifier, $R^1$, $R^2$, $R^3$, and X is as defined above and described herein.

In some embodiments, the present invention provides a conjugate of formula X-g:

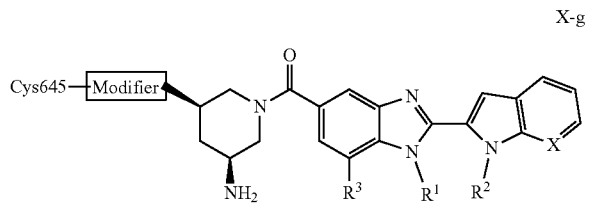

X-g wherein each of Cys645, Modifier, $R^1$, $R^2$, $R^3$, and X is as defined above and described herein.

In some embodiments, the present invention provides a conjugate of formula X-h:

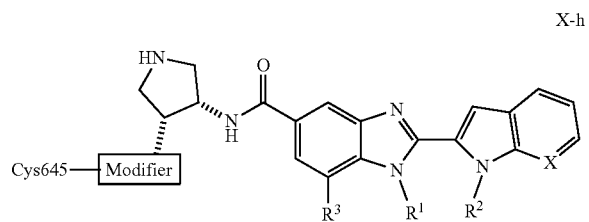

X-h wherein each of Cys645, Modifier, $R^1$, $R^2$, $R^3$, and X is as defined above and described herein.

In some embodiments, the present invention provides a conjugate of formula X-i:

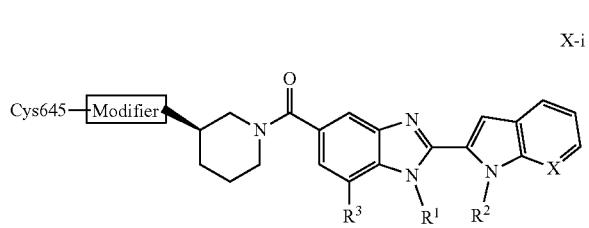

X-i wherein each of Cys645, Modifier, $R^1$, $R^2$, $R^3$, and X is as defined above and described herein.

A Modifier of the present invention is a bivalent group resulting from covalent bonding of a Warhead Group with the Cys645 of PAD4. It will be understood that the exemplary modifiers below are shown as conjugated to the sulfhydryl of Cys645 of PAD4.

TABLE X

Modifiers Conjugated to Cys645

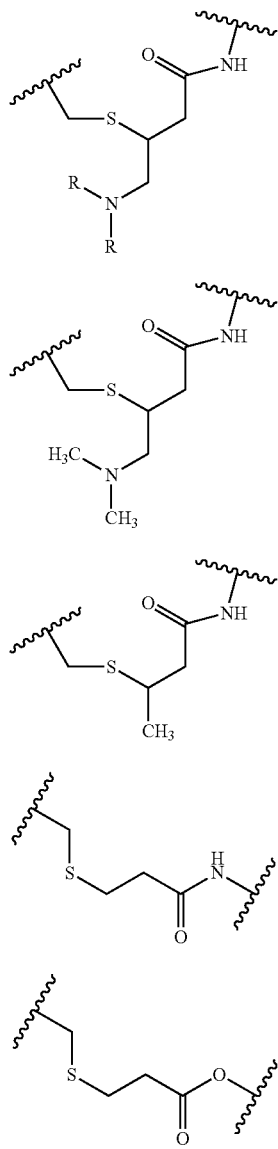

4. Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably inhibit PAD4, in a biological sample or in a patient. In certain embodiments, the amount of compound in compositions of this invention is such that is effective to measurably inhibit PAD4, in a biological sample or in a patient. In certain embodiments, a composition of this invention is formulated for administration to a patient in need of such composition. In some embodiments, a composition of this invention is formulated for oral administration to a patient.

The term "subject," as used herein, is used interchangeably with the term "patient" and means an animal, preferably a mammal. In some embodiments, a subject or patient is a human. In other embodiments, a subject (or patient) is a veterinary subject (or patient). In some embodiments, a veterinary subject (or patient) is a canine, a feline, or an equine subject.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention.

Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the inhibitor can be administered to a patient receiving these compositions.

A compound of the current invention can be administered alone or in combination with one or more other therapeutic compounds, possible combination therapy taking the form of fixed combinations or the administration of a compound of the invention and one or more other therapeutic compounds being staggered or given independently of one another, or the combined administration of fixed combinations and one or more other therapeutic compounds. A compound of the current invention can besides or in addition be administered especially for tumor therapy in combination with chemotherapy, radiotherapy, immunotherapy, phototherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of the current invention, an additional therapeutic agent, and a pharmaceutically acceptable carrier, adjuvant, or vehicle.

The amount of both an inventive compound and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive compound can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

Compounds and compositions described herein are generally useful for the inhibition of PAD4.

The activity of a compound utilized in this invention as an inhibitor of PAD4, may be assayed in vitro, in vivo or in a cell line. In vitro assays include assays that determine the inhibition of PAD4. Detailed conditions for assaying a compound utilized in this invention as an inhibitor of PAD4 are set forth in the Examples below. In some embodiments, a provided compound inhibits PAD4 selectively as compared to PAD2.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

Provided compounds are inhibitors of PAD4 and are therefore useful for treating one or more disorders associated with activity of PAD4. Thus, in certain embodiments, the present invention provides a method for treating a PAD4-mediated disorder comprising the step of administering to a patient in need thereof a compound of the present invention, or pharmaceutically acceptable composition thereof.

In one embodiment, a PAD4-mediated disorder is a disease, condition, or disorder mediated by inappropriate PAD4 activity. In some embodiments, a PAD4-mediated disorder is selected from the group consisting of rheumatoid arthritis, vasculitis, systemic lupus erythematosus, ulcerative colitis, cancer, cystic fibrosis, asthma, cutaneous lupus erythematosis, and psoriasis. In a further embodiment, the disorder mediated by inappropriate PAD4 activity is rheumatoid arthritis. In a further embodiment, the disorder mediated by inappropriate PAD4 activity is systemic lupus. In a further embodiment, the disorder mediated by inappropriate PAD4 activity is vasculitis. In a further embodiment, the disorder mediated by inappropriate PAD4 activity is cutaneous lupus erythematosis. In a further embodiment, the disorder mediated by inappropriate PAD4 activity is psoriasis.

In one embodiment there is provided a method of treatment of rheumatoid arthritis, vasculitis, systemic lupus erythematosus, ulcerative colitis, cancer, cystic fibrosis, asthma, cutaneous lupus erythematosis, or psoriasis, which method comprises administering to a human subject in need thereof, a therapeutically effective amount of a provided compound or a pharmaceutically acceptable salt thereof.

In one embodiment there is provided a method of treatment of rheumatoid arthritis, which method comprises administering to a human subject in need thereof, a therapeutically effective amount of a provided compound, or a pharmaceutically acceptable salt thereof. In one embodiment there is provided a method of treatment of systemic lupus, which method comprises administering to a human subject in need thereof, a therapeutically effective amount of a provided compound, or a pharmaceutically acceptable salt thereof. In one embodiment there is provided a method of treatment of vasculitis, which method comprises administering to a human subject in need thereof, a therapeutically effective amount of a provided compound, or a pharmaceutically acceptable salt thereof. In one embodiment there is provided a method of treatment of cutaneous lupus erythematosis, which method comprises administering to a human subject in need thereof, a therapeutically effective amount of a provided compound, or a pharmaceutically acceptable salt thereof. In one embodiment there is provided a method of treatment of psoriasis, which method comprises administering to a human subject in need thereof, a therapeutically effective amount of a provided compound, or a pharmaceutically acceptable salt thereof.

In some embodiments, a PAD4-mediated disorder is selected from the group consisting of acid-induced lung injury, acne (PAPA), acute lymphocytic leukemia, acute, respiratory distress syndrome, Addison's disease, adrenal hyperplasia, adrenocortical insufficiency, ageing, AIDS, alcoholic hepatitis, alcoholic hepatitis, alcoholic liver disease, allergen induced asthma, allergic bronchopulmonary, aspergillosis, allergic conjunctivitis, alopecia, Alzheimer's disease, amyloidosis, amyotropic lateral sclerosis, and weight loss, angina pectoris, angioedema, anhidrotic ecodermal dysplasia-ID, ankylosing spondylitis, anterior segment, inflammation, antiphospholipid syndrome, aphthous stomatitis, appendicitis, arthritis, asthma, atherosclerosis, atopic dermatitis, autoimmune diseases, autoimmune hepatitis, bee sting-induced inflammation, behcet's disease, Behcet's syndrome, Bells Palsey, berylliosis, Blau syndrome, bone pain, bronchiolitis, burns, bursitis, cancer, cardiac hypertrophy, carpal tunnel syndrome, catabolic disorders, cataracts, cerebral aneurysm, chemical irritant-induced inflammation, chorioretinitis, chronic heart failure, chronic lung disease of prematurity, chronic lymphocytic leukemia, chronic obstructive pulmonary disease, colitis, complex regional pain syndrome, connective tissue disease, corneal ulcer, crohn's disease, cryopyrin-associated periodic syndromes, cyrptococcosis, cystic fibrosis, deficiency of the interleukin-1-receptor antagonist (DIRA), dermatitis, dermatitis endotoxemia, dermatomyositis, diffuse intrinsic pontine glioma, endometriosis, endotoxemia, epicondylitis, erythroblastopenia, familial amyloidotic polyneuropathy, familial cold urticarial, familial mediterranean fever, fetal growth retardation, glaucoma, glomerular disease, glomerular nephritis, gout, gouty arthritis, graft-versus-host disease, gut diseases, head injury, headache, hearing loss, heart disease, hemolytic anemia, Henoch-Scholein purpura, hepatitis, hereditary periodic fever syndrome, herpes zoster and simplex, HIV-1, Hodgkin's disease, Huntington's disease, hyaline membrane disease, hyperammonemia, hypercalcemia, hypercholesterolemia, hyperimmunoglobulinemia D with recurrent fever (HIDS), hypoplastic and other anemias, hypoplastic anemia, idiopathic thrombocytopenic purpura, incontinentia pigmenti, infectious mononucleosis, inflammatory bowel disease, inflammatory lung disease, inflammatory neuropathy, inflammatory pain, insect bite-induced inflammation, iritis, irritant-induced inflammation, ischemia/reperfusion, juvenile rheumatoid arthritis, keratitis, kidney disease, kidney injury caused by parasitic infections, kidney injury caused by parasitic infections, kidney transplant rejection prophylaxis, leptospiriosis, leukemia, Loeffler's syndrome, lung injury, lung injury, lupus, lupus, lupus nephritis, lymphoma, meningitis, mesothelioma, mixed connective tissue disease, Muckle-Wells syndrome (urticaria deafness amyloidosis), multiple sclerosis, muscle wasting, muscular dystrophy, myasthenia gravis, myocarditis, mycosis fungiodes, mycosis fungoides, myelodysplastic syndrome, myositis, nasal sinusitis, necrotizing enterocolitis, neonatal onset multisystem inflammatory disease (NOMID), nephrotic syndrome, neuritis, neuropathological diseases, non-allergen induced asthma, obesity, ocular allergy, optic neuritis, organ transplant, osterarthritis, otitis media, paget's disease, pain, pancreatitis, Parkinson's disease, pemphigus, pericarditis, periodic fever, periodontitis, peritoneal endometriosis, pertussis, pharyngitis and adenitis (PFAPA syndrome), plant irritant-induced inflammation, pneumonia, pneumonitis, pneumosysts infection, poison ivy/urushiol oil-induced inflammation, polyarteritis nodosa, polychondritis, polycystic kidney disease, polymyositis, psoriasis, psoriasis, psoriasis, psoriasis, psychosocial stress diseases, pulmonary disease, pulmonary hypertension, pulmonayr fibrosis, pyoderma gangrenosum, pyogenic sterile arthritis, renal disease, retinal disease, rheumatic carditis, rheumatic disease, rheumatoid arthritis, sarcoidosis, seborrhea, sepsis, severe pain, sickle cell, sickle cell anemia, silica-induced disease, Sjogren's syndrome, skin diseases, sleep apnea, solid tumors, spinal cord injury, Stevens-Johnson syndrome, stroke, subarachnoid hemorrhage, sunburn, temporal arteritis, tenosynovitis, thrombocytopenia, thyroiditis, tissue transplant, TNF receptor associated periodic syndrome (TRAPS), toxoplasmosis, transplant, traumatic brain injury, tuberculosis, type 1 diabetes, type 2 diabetes, ulcerative colitis, urticarial, uveitis, and Wegener's granulomatosis.

In one embodiment, the invention provides a provided compound, or a pharmaceutically acceptable salt thereof, for use in therapy. In another embodiment, the invention provides a provided compound, or a pharmaceutically acceptable salt thereof, for use in the treatment of a disorder mediated by inappropriate PAD4 activity. In another embodiment, the invention provides a provided compound, or a pharmaceutically acceptable salt thereof, for use in the treatment of rheumatoid arthritis, vasculitis, systemic lupus erythematosus, ulcerative colitis, cancer, cystic fibrosis, asthma, cutaneous lupus erythematosis, or psoriasis. In another embodiment, the invention provides a provided compound, or a pharmaceutically acceptable salt thereof, for use in the treatment of rheumatoid arthritis. In another embodiment, the invention provides a provided compound, or a pharmaceutically acceptable salt thereof, for use in the treatment of systemic lupus. In another embodiment, the invention provides a provided compound, or a pharmaceutically acceptable salt thereof, for use in the treatment of vasculitis. In another embodiment, the invention provides a provided compound, or a pharmaceutically acceptable salt thereof, for use in the treatment of cutaneous lupus erythematosis. In another embodiment, the invention provides a provided compound, or a pharmaceutically acceptable salt thereof, for use in the treatment of psoriasis. In another embodiment, the invention provides the use of a provided compound, or a pharmaceutically acceptable salt thereof, in the manufacture of a medicament for use in the treatment of a disorder mediated by inappropriate PAD4 activity. In another embodiment, the invention provides the use of a provided compound, or a pharmaceutically acceptable salt thereof, in the manufacture of a medicament for use in the treatment of rheumatoid arthritis, vasculitis, systemic lupus erythematosus, ulcerative colitis, cancer, cystic fibrosis, asthma, cutaneous lupus erythematosis, or psoriasis. In another embodiment, the invention provides the use of a provided compound, or a pharmaceutically acceptable salt thereof, in the manufacture of a medicament for use in the treatment of rheumatoid arthritis. In another embodiment, the invention provides the use of a provided compound, or a pharmaceutically acceptable salt thereof, in the manufacture of a medicament for use in the treatment of systemic lupus. In another embodiment, the invention provides the use of a provided compound, or a pharmaceutically acceptable salt thereof, in the manufacture of a medicament for use in the treatment of vasculitis. In another embodiment, the invention provides the use of a provided compound, or a pharmaceutically acceptable salt thereof, in the manufacture of a medicament for use in the treatment of cutaneous lupus erythematosis. In another embodiment, the invention provides the use of a provided compound, or a pharmaceutically acceptable salt thereof, in the manufacture of a medicament for use in the treatment of psoriasis. In a further embodiment, the invention provides a pharmaceutical composition for the treatment or prophylaxis of a disorder mediated by inappropriate PAD4 activity comprising a provided compound, or a pharmaceutically acceptable salt thereof. In a further embodiment, the invention provides a pharmaceutical composition for the treatment or prophylaxis of rheumatoid arthritis, vasculitis, systemic lupus erythematosus, ulcerative colitis, cancer, cystic fibrosis, asthma, cutaneous lupus erythematosis, or psoriasis, comprising a provided compound, or a pharmaceutically acceptable salt thereof. In a further embodiment, the invention provides a pharmaceutical composition for the treatment or prophylaxis of rheumatoid arthritis comprising a provided compound, or a pharmaceutically acceptable salt thereof. In a further embodiment, the invention provides a pharmaceutical composition for the treatment or prophylaxis of systemic lupus comprising a provided compound, or a pharmaceutically acceptable salt thereof. In a further embodiment, the invention provides a pharmaceutical composition for the treatment or prophylaxis of vasculitis comprising a provided compound, or a pharmaceutically acceptable salt thereof. In a further embodiment, the invention provides a pharmaceutical composition for the treatment or prophylaxis of cutaneous lupus erythematosis comprising a provided compound, or a pharmaceutically acceptable salt thereof. In a further embodiment, the invention provides a pharmaceutical composition for the treatment or prophylaxis of psoriasis comprising a provided compound, or a pharmaceutically acceptable salt thereof All features of each of the aspects of the invention apply to all other aspects mutatis mutandis.

In order that the invention described herein may be more fully understood, the following examples are set forth. It should be understood that these examples are for illustrative purposes only and are not to be construed as limiting this invention in any manner.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

List of Common Abbreviations Used in the Experimental Section.

AcOH: acetic acid
(Boc)$_2$O: di-tert-butyl dicarbonate
Chiral HPLC: chiral high performance liquid chromatography
DCM: dichloromethane
Dess Martin Periodinane: 1,1,1-Tris(acetyloxy)-1,1-dihydro-1,2-benziodoxol-3-(1H)-one
DIAD: diisopropyl azodicarboxylate
DIPEA: N,N-diisopropylethylamine
DMAP: 4-dimethylaminopyridine
DMF: N,N-dimethylformamide
DMSO: dimethyl sulfoxide
EtOAc: ethyl acetate
EtOH: ethanol
HATU: N-[(Dimethylamino)-1H-1,2,3-triazolo-[4,5-b]pyridin-1-ylmethylene]-N-methylmethanaminium hexafluorophosphate N-oxide
H-Cube: continuous flow hydrogenation reactor
HPLC: high performance liquid chromatography
HCl: hydrochloric acid
Kieselguhr: diatomaceous earth
LCMS: Liquid chromatography-mass spectrometry
M: molar
Me: methyl
MeCN: acetonitrile
MeI: methyl iodide
min: minutes
mL: millilitres
MeOH: methanol
MsCl: methanesulfonyl chloride
NaHMDS: sodium bis(trimethylsilyl)amide
NMR: Nuclear Magnetic Resonance
° C.: degrees Celsius
Pd/C: palladium on carbon
Pd(OH)$_2$/C: palladium hydroxide on carbon
prep HPLC: preparative high performance liquid chromatography
STAB: sodium triacetoxyborohydride
TBAF: tetrabutylammonium fluoride
TBDMSCl: tert-Butyldimethylsilyl chloride
TBTU: O-(Benzotriazol-1-yl)-N,N,N',N'-tetramethyluronium tetrafluoroborate
TEA: triethylamine
TFA: trifluoracetic acid
THF: tetrahydrofuran
T$_{ret}$: retention time Preparative HPLC Methods
Basic HPLC Preparative Method
Column: XBridge™ Prep. C18 10 um OBD™, 30×100 mm
Mobile Phase: 5-95% Acetonitrile (0.2% ammonium hydroxide) in Water (0.2% ammonium hydroxide) over 14 minutes
Flow Rate: 40 mL/min
UV Detection: 215 and 254 nm Acidic HPLC Preparative Method
Column: Sunfire™ Prep. C18 10 um OBD™, 30×100 mm
Mobile Phase: 5-95% Acetonitrile (0.1% formic acid) in Water (0.1% formic acid) over 14 minutes
Flow Rate: 40 mL/min
UV Detection: 215 and 254 nm
Analytical LCMS Methods:
Method A
MET/u-HPLC (MSQ1 low pH 7 min method)
Column: Phenomenex Kinetex-XB C18, 2.1 mm×100 mm, 1.7 µm
Flow rate: 0.6 ml/min
Mobile Phase: A, Formic acid (aqueous) 0.1% and B, Formic acid (MeCN) 0.1%
Injection Vol: 3 µL
Temp.: 40° C.
Detection: 215 nm (nominal)
Gradient Time (minutes)-% B
0.00-5
5.30-100
5.80-100
5.82-5
Method B
MET/CR/1600 (MS10 high pH 7 min method)
Column: Phenomenex Gemini C18, 2.0 mm×100 mm, 3 µm
Flow rate: 0.5 mL/min
Mobile phase: A, 2 mM ammonium bicarbonate in HPLC grade water pH10
B HPLC grade MeCN
Injection volume: 3 µL
Temperature: 50° C.
Detection: 215 nm
Gradient time: (minutes)-% B
0.0-5
5.50-100
5.90-100
5.92-5
9.00-5
Method C
METCR 1416 (low pH Shimadzu 7 min method)
Column: Waters Atlantis dC18, 2.1 mm×100 mm, 3 µm column
Flow rate: 0.6 mL/min
Mobile Phase: A, Formic acid (aqueous) 0.1% and B, Formic acid (acetonitrile) 0.1%
Injection Vol: 3 µL
Temp.: 40° C.
Detection: 215 nm (nominal)
Gradient Time (minutes)-% B
0.00-5
5.00-100
5.40-100
5.42-5
Method D
METCR 1410 (low pH Shimadzu 2 min method)
Column: Kinetex Core-Shell C18, 2.1 mm×50 mm, 5 µm column
Flow rate: 1.2 mL/min
Mobile Phase: A, Formic acid (aqueous) 0.1% and B, Formic acid (acetonitrile) 0.1%
Injection Vol: 3 µL
Temp.: 40° C.
Detection: 215 nm (nominal)
Gradient Time (minutes)-% B
0.00-5
1.20-100
1.30-100
1.31-5

Method H
MET/u-HPLC (high pH MS16 7 min method)
Column: Waters UPLC CSH C18, 2.1 mm×100 mm 5 μm column
Flow rate: 0.6 mL/min
Mobile Phase: A, 2 mM Ammonium bicarbonate modified to pH 10 with Ammonium hydroxide (aqueous) and B, acetonitrile
Injection Vol: 3 μL
Temp.: 40° C.
Detection: 215 nm (nominal)
Gradient Time (minutes)-% B
0.00-5
5.30-100
5.80-100
5.82-5

Method J
MET/CR/0990 (high pH 3 min method)
Column: Phenomenex Gemini C18, 2.0 mm×100 mm, 3 μm
Flow rate: 1 mL/min
Mobile phase: A, 2 mM ammonium bicarbonate in HPLC grade water pH10
B HPLC grade MeCN
Injection volume: 3 μL
Temperature: 60° C.
Detection: 215 nm
Gradient time: (minutes)-% B
0.0-1
1.80-100
2.10-100
2.30-1

Analytical and Preparative Chiral HPLC Methods:
Method E:
Chiral HPLC preparative method
Column: Lux C1 (21.2 mm×250 mm, 5 μm)
Flow rate: 50 mL/min
Mobile Phase: 40:60 MeOH:CO2 (0.1% v/v NH3)
Injection Vol: 500 μL (2.5 mg)
Temp.: 40° C.
Detection: 220 nm Method F:
Chiral purity analysis method
Column: Lux C1 (4.6 mm×250 mm, 5 um)
Flow Rate: 4 mL/min
Injection Vol: 1.0 μL
Temp.: 40 C
UV Detection: 210-400 nm
Isocratic Conditions 40:60 MeOH:CO2 (0.1% v/v NH3)

Certain compounds of the present invention were prepared according to Scheme 1, steps 1 to 9, below.

Example 1. Synthesis of trans-rac-2-[1-(cyclopropylmethyl)-1H-pyrrolo[2,3-b]pyridin-2-yl]-N-[(3R,4R)-4-[(2E)-4-(dimethylamino)but-2-enamido]pyrrolidin-3-yl]-1-methyl-1H-1,3-benzodiazole-5-carboxamide EV-AE3989-001 (EOAI3442248, I-9)

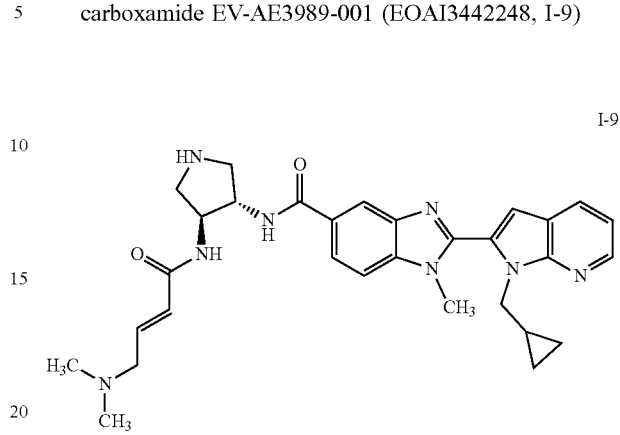

I-9

Scheme 1 Step 1

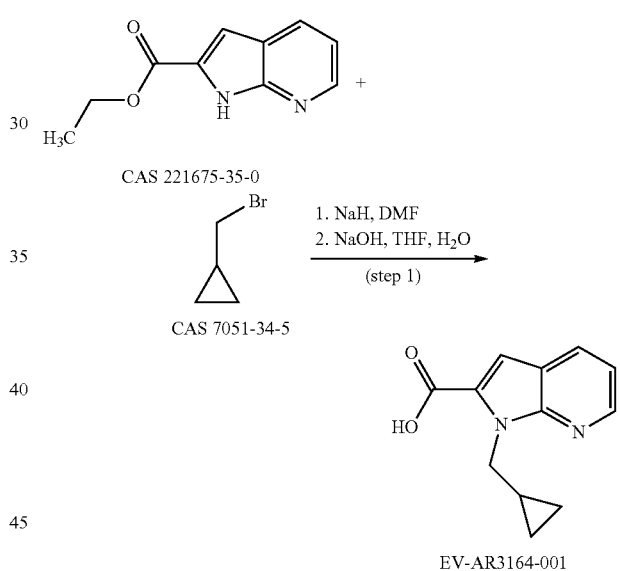

1-(Cyclopropylmethyl)-1H-pyrrolo[2,3-b]pyridine-2-carboxylic acid EV-AR3164-001—Step 1

To a stirred solution of ethyl 1H-pyrrolo[2,3-b]pyridine-2-carboxylate (CAS 221675-35-0, 4.40 g, 23.1 mmol) in DMF (50 ml) was added sodium hydride (60%, 1.05 g, 26.3 mmol). The mixture was stirred under nitrogen at room temperature for 45 minutes and (bromomethyl)cyclopropane (CAS 7051-34-5, 2.70 ml, 27.8 mmol) was added. The mixture was stirred at room temperature for 2.5 h and the solvent was removed in vacuo. The residue was suspended in THF (40 ml) and 5M aqueous sodium hydroxide (22 ml, 110 mmol) was added. The mixture was stirred at 50° C. for 3.5 h. Additional THF (20 ml) and 5M aqueous sodium hydroxide (22 ml, 110 mmol) were added and the reaction was stirred at 50° C. for 16 h. The reaction crude was concentrated in vacuo and water (10 ml) and 5M aqueous hydrochloric acid (100 ml) were added. The solid was filtered off, washed with water (2×100 ml) and dried to obtain 3.46 g (69.2%) of 1-(cyclopropylmethyl)-1H-pyrrolo[2,3-b]pyridine-2-carboxylic acid EV-AR3164-001 as a white powder. LCMS (method D): retention time 1.03 min, M/z=217 (M+1).

Scheme 1 Step 2

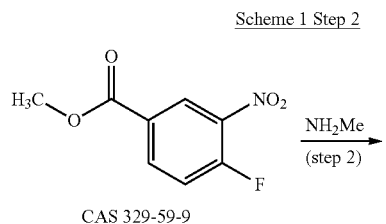

CAS 329-59-9

EV-AR3152-001

Methyl 4-(methylamino)-3-nitrobenzoate EV-AR3152-001—Step 2

To a stirred solution of methyl 4-fluoro-3-nitrobenzoate (CAS 329-59-9, 5.00 g, 25.1 mmol) in DMF (50 ml) was added methanamine hydrochloride (1:1) (2.00 g, 29.6 mmol) and potassium carbonate (4.50 g, 32.6 mmol). The mixture was stirred at room temperature under nitrogen for 18 h. The reaction crude was concentrated in vacuo and the residue was partitioned between in EtOAc (350 ml) and 1N aqueous hydrochloric acid (250 ml). The organic layer was washed further with 1N aqueous hydrochloric acid (150 ml) and saturated aqueous sodium chloride (100 ml). The organic layer was dried over magnesium sulfate, filtered and concentrated in vacuo to obtain 5.30 g (quantitative) of methyl 4-(methylamino)-3-nitrobenzoate EV-AR3152-001 as a yellow powder. LCMS (method D): retention time 1.07 min, M/z=211 (M+1).

Scheme 1 Step 3

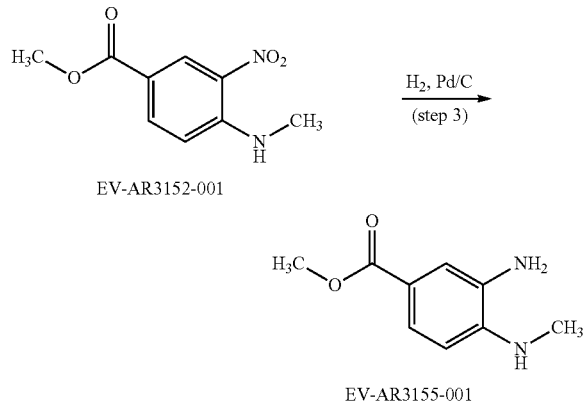

EV-AR3152-001

EV-AR3155-001

Methyl 3-amino-4-(methylamino)benzoate EV-AR3155-001—Step 3

To a stirred solution of methyl 4-(methylamino)-3-nitrobenzoate (EV-AR3152-001, 5.30 g, 25.2 mmol) in ethanol (100 ml) under nitrogen was added 10% Pd/C (1.30 g, 0.05 mmol). The reaction was then placed under a hydrogen atmosphere and stirred at room temperature for 4 h. The reaction mixture was diluted with methanol (100 ml) and Kieselguhr was added. The mixture was stirred at room temperature for 10 minutes and filtered under vacuum. The filter was washed with methanol (3×50 ml) and the filtrate was concentrated in vacuo to obtain 4.39 g (96.6%) of methyl 3-amino-4-(methylamino)benzoate EV-AR3155-001 as a brown powder. LCMS (method D): retention time 0.75 min, M/z=181 (M+1).

Scheme 1 Step 4

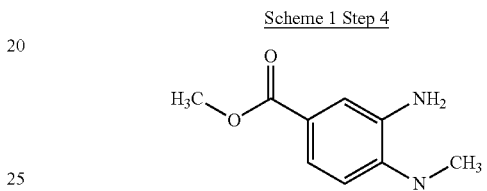

EV-AR3155-001

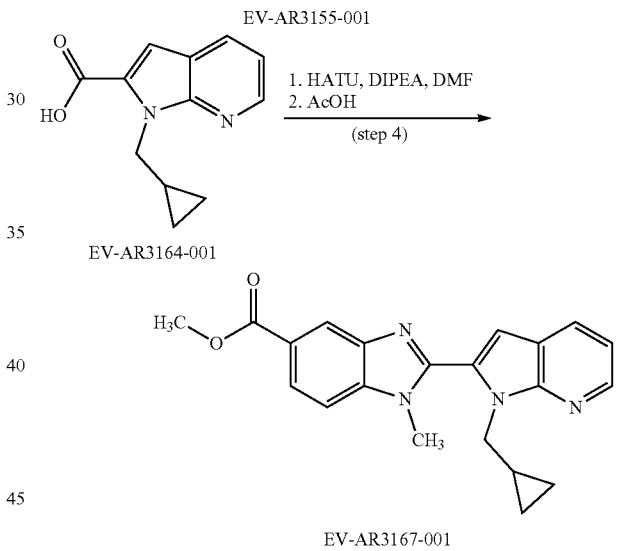

EV-AR3164-001

EV-AR3167-001

Methyl 2-[1-(cyclopropylmethyl)-1H-pyrrolo[2,3-b]pyridin-2-yl]-1-methyl-1H-1,3-benzodiazole-5-carboxylate EV-AR3167-001—Step 4

To a solution of 1-(cyclopropylmethyl)-1H-pyrrolo[2,3-b]pyridine-2-carboxylic acid (EV-AR3164-001, 2.20 g, 10.2 mmol) in dry DMF (40 ml) was added HATU (4.95 g, 12.8 mmol) and DIPEA (2.25 ml, 12.8 mmol). The mixture was stirred at room temperature for 1 h then methyl 3-amino-4-(methylamino)benzoate (EV-AR3155-001, 2.02 g, 11.2 mmol) was added. The mixture was stirred at room temperature for 16 h. The solvent was removed in vacuo and the residue was dissolved in acetic acid (40 ml) and stirred at 80° C. for 2 h, then 85° C. for 30 minutes then 90° C. for 1 h. The solvent was removed in vacuo and the crude material was purified by flash column chromatography (12-100% EtOAc/heptane) to obtain 3.08 g (83.2%) of methyl 2-[1-(cyclopropylmethyl)-1H-pyrrolo[2,3-b]pyridin-2-yl]-1- methyl-1H-1,3-benzodiazole-5-carboxylate EV-AR3167-001 as a pink powder. LCMS (method D): retention time 1.20 min, M/z=361 (M+1).

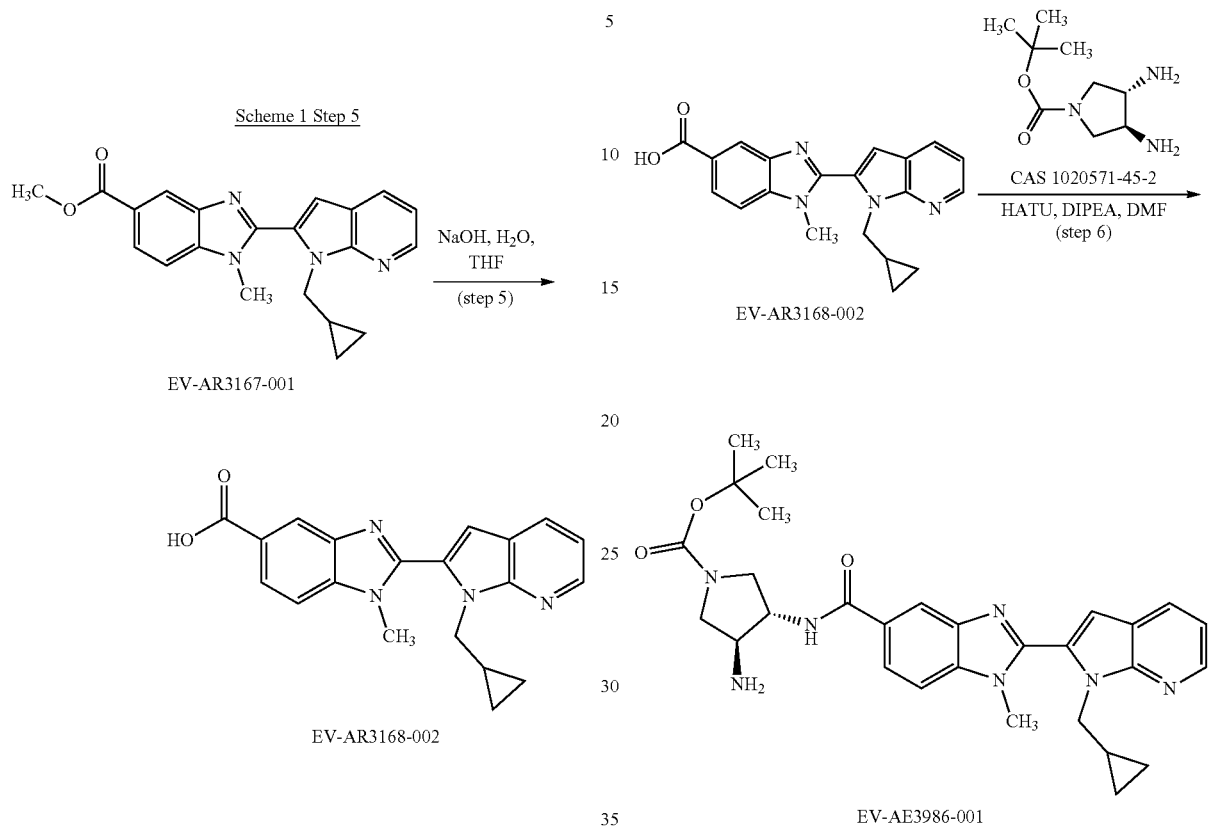

2-[1-(cyclopropylmethyl)-1H-pyrrolo[2,3-b]pyridin-2-yl]-1-methyl-1H-1,3-benzodiazole-5-carboxylic Acid EV-AR3168-002—Step 5

To a suspension of methyl 2-[1-(cyclopropylmethyl)-1H-pyrrolo[2,3-b]pyridin-2-yl]-1-methyl-1H-1,3-benzodiazole-5-carboxylate (EV-AR3167-001, 3.08 g, 8.46 mmol) in methanol (60 ml) was added 2M aqueous sodium hydroxide (30 ml, 60.0 mmol). The mixture was then stirred at 50° C. for 2 h. The reaction was allowed to cool to room temperature and the solvent was removed in vacuo. Water (50 ml) was added followed by 2M aqueous HCl until pH 3 was achieved. The mixture was stirred for 15 minutes and filtered through a sinter. The solid was washed with water (2×50 ml) and air-dried for 64 h to afford 1.81 g (61.2%) of 2-[1-(cyclopropylmethyl)-1H-pyrrolo[2,3-b]pyridin-2-yl]-1-methyl-1H-1,3-benzodiazole-5-carboxylic acid EV-AR3168-001 as a beige solid. LCMS (method D): retention time 1.05 min, M/z=347 (M+1). The filtrate was further acidified by addition of 2M aqueous HCl until a precipitate started to form. The mixture was allowed to stand for 1 h and filtered through a sinter. The solid was washed with water (2×20 ml) and air-dried under vacuum for 3 h to obtain 460 mg of (15.7%) 2-[1-(cyclopropylmethyl)-1H-pyrrolo[2,3-b]pyridin-2-yl]-1-methyl-1H-1,3-benzodiazole-5-carboxylic acid EV-AR3168-002 as an off white powder LCMS (method D): retention time 1.06 min, M/z=347 (M+1).

Trans-rac-tert-butyl (3R,4R)-3-amino-4-{2-[1-(cyclopropylmethyl)-1H-pyrrolo[2,3-b]pyridin-2-yl]-1-methyl-1H-1,3-benzodiazole-5-amido}pyrrolidine-1-carboxylate—EV-AE3986-001—Step 6

A solution of 2-[1-(cyclopropylmethyl)-1H-pyrrolo[2,3-b]pyridin-2-yl]-1-methyl-1H-1,3-benzodiazole-5-carboxylic acid (EV-AQ1914-001, 100 mg, 0.29 mmol) and HATU (121 mg, 0.32 mmol) in dry DMF (2 ml) was treated with DIPEA (55 μL, 0.32 mmol) at room temperature. The mixture was stirred for 1 h then trans-rac-tert-butyl (3R,4R)-3,4-diaminopyrrolidine-1-carboxylate (CAS 1020571-45-2, 58 mg, 0.29 mmol) was added and the reaction mixture stirred at room temperature for 1 h. The reaction mixture was diluted with EtOAc (10 ml), washed with water (5 ml) then saturated aqueous sodium chloride (3 ml). The organic layer was dried over sodium sulfate, filtered and concentrated in vacuo. The residue was purified by column chromatography (1-9% MeOH/DCM) to obtain 40 mg (25%) of trans-rac-tert-butyl (3R,4R)-3-amino-4-{2-[1-(cyclopropylmethyl)-1H-pyrrolo[2,3-b]pyridin-2-yl]-1-methyl-1H-1,3-benzodiazole-5-amido}pyrrolidine-1-carboxylate EV-AE3986-001 as a colourless crystalline solid. LCMS (method D): retention time 0.98 min, M/z=530 (M+1).

Scheme 1 Step 7

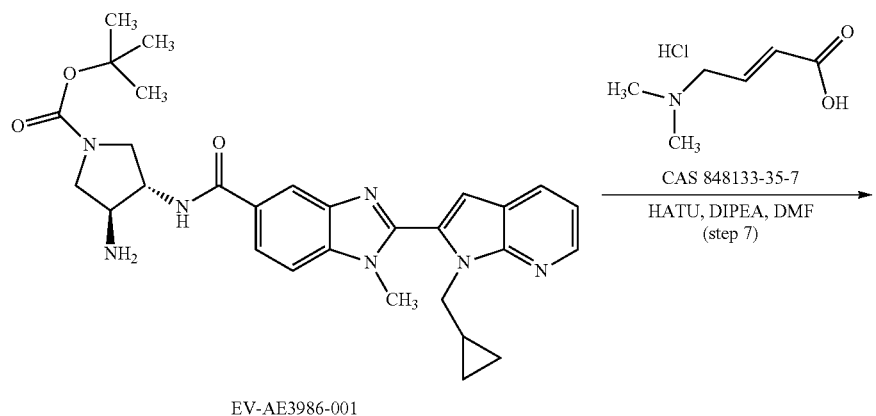

EV-AE3986-001

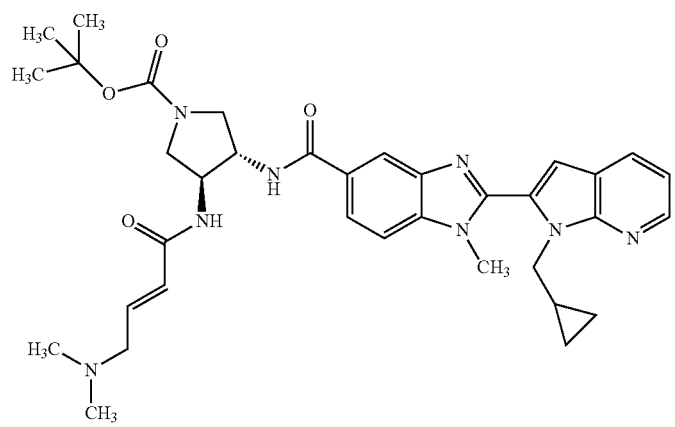

EV-AE3988-001

Trans-rac-formic acid; tert-butyl (3R,4R)-3-{2-[1-(cyclopropylmethyl)-1H-pyrrolo[2,3-b]pyridin-2-yl]-1-methyl-1H-1,3-benzodiazole-5-amido}-4-[(2E)-4-(dimethylamino)but-2-enamido]pyrrolidine-1-carboxylate—EV-AE3988-001—Step 7

A solution of trans-rac-tert-butyl (3R,4R)-3-amino-4-{2-[1-(cyclopropylmethyl)-1H-pyrrolo[2,3-b]pyridin-2-yl]-1-methyl-1H-1,3-benzodiazole-5-amido}pyrrolidine-1-carboxylate (EV-AE3986-001, 40 mg, 0.08 mmol), (2E)-4-(dimethylamino)but-2-enoic acid hydrochloride (15 mg, 0.091 mmol) and HATU (34 mg, 0.091 mmol) in dry DMF (1 ml) was treated with DIPEA (29 μl, 0.16 mmol) at room temperature and the mixture was stirred for 20 minutes. The reaction mixture was diluted with EtOAc (10 ml) and washed with water (5 ml). The aqueous layer was re-extracted with EtOAc (5 ml). The EtOAc layers were combined, washed with saturated aqueous sodium chloride (5 ml), dried over sodium sulfate, filtered and concentrated in vacuo. The residue was purified by prep HPLC (acidic method) to obtain 18 mg (34.7%) of trans-rac-formic acid; tert-butyl (3R,4R)-3-{2-[1-(cyclopropylmethyl)-1H-pyrrolo[2,3-b]pyridin-2-yl]-1-methyl-1H-1,3-benzodiazole-5-amido}-4-[(2E)-4-(dimethylamino)but-2-enamido]pyrrolidine-1-carboxylate EV-AE3988-001 as a colourless crystalline solid. LCMS (method D): retention time 1.00 min, M/z=641 (M+1).

Scheme 1 Step 8

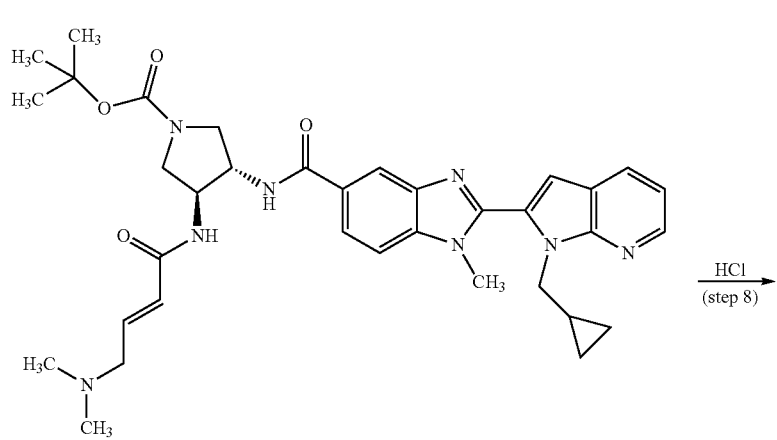

EV-AE3988-001

I-9

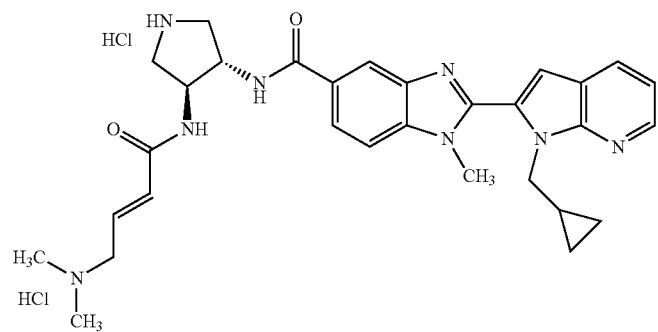

EV-AE3989-001

Trans-rac-2-[1-(cyclopropylmethyl)-1H-pyrrolo[2,3-b]pyridin-2-yl]-N-[(3R,4R)-4-[(2E)-4-(dimethylamino)but-2-enamido]pyrrolidin-3-yl]-1-methyl-1H-1,3-benzodiazole-5-carboxamide Dihydrochloride—EV-AE3989-001—Step 8

To trans-rac-formic acid; tert-butyl (3R,4R)-3-{2-[1-(cyclopropylmethyl)-1H-pyrrolo[2,3-b]pyridin-2-yl]-1-methyl-1H-1,3-benzodiazole-5-amido}-4-[(2E)-4-(dimethylamino)but-2-enamido]pyrrolidine-1-carboxylate (EV-AE3988-001, 17 mg, 0.03 mmol) was added 2M HCl in ether (0.13 ml, 0.25 mmol) and the mixture was left standing at room temperature for 1 h. Another portion of 2M HCl in ether (0.13 ml) was added and swirled around the reaction vial, then allowed to stand for 30 mins. The reaction mixture was concentrated to dryness and dried in vacuo to obtain 15 mg (97%) of trans-rac-2-[1-(cyclopropylmethyl)-1H-pyrrolo[2,3-b]pyridin-2-yl]-N-[(3R,4R)-4-[(2E)-4-(dimethylamino)but-2-enamido]pyrrolidin-3-yl]-1-methyl-1H-1,3-benzodiazole-5-carboxamide dihydrochloride EV-AE3989-001 as an off-white crystalline solid. LCMS (method C): retention time 2.80 min, M/z=541 (M+1).

Example 2. Chiral HPLC to Obtain trans-tert-butyl (3S,4S)-3-{2-[1-(cyclopropylmethyl)-1H-pyrrolo[2,3-b]pyridin-2-yl]-1-methyl-1H-1,3-benzodiazole-5-amido}-4-[(2E)-4-(dimethylamino)but-2-enamido]pyrrolidine-1-carboxylate and trans-tert-butyl (3R,4R)-3-{2-[1-(cyclopropylmethyl)-1H-pyrrolo[2,3-b]pyridin-2-yl]-1-methyl-1H-1,3-benzodiazole-5-amido}-4-[(2E)-4-(dimethylamino)but-2-enamido]pyrrolidine-1-carboxylate—EV-AU3235-001 and EV-AU3235-002—Step 9

Scheme 1 Step 9

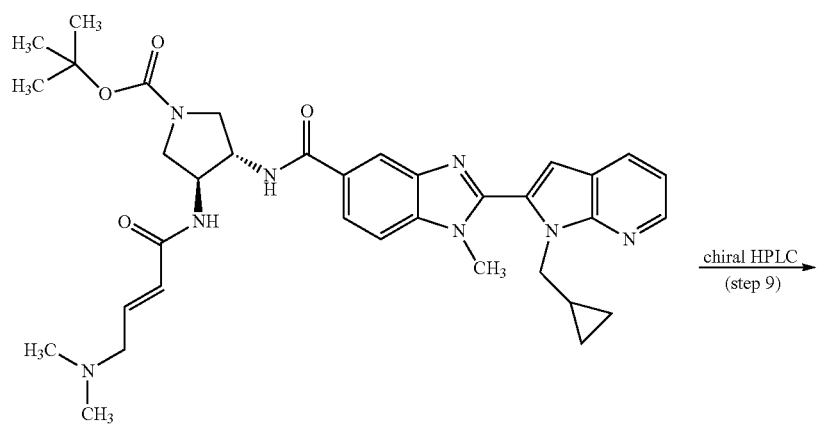

EV-AE3988-001

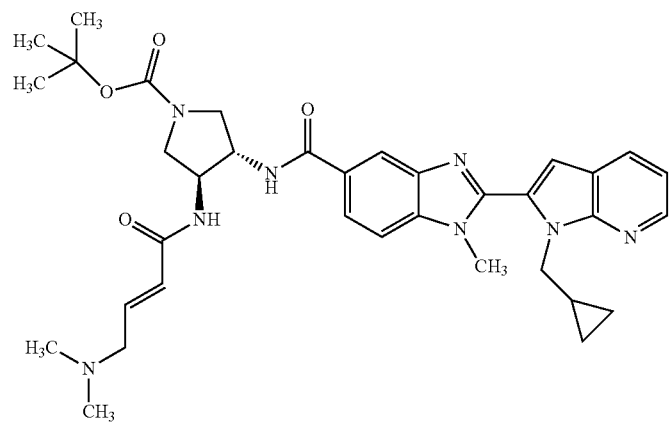

EV-AU3235-001 and

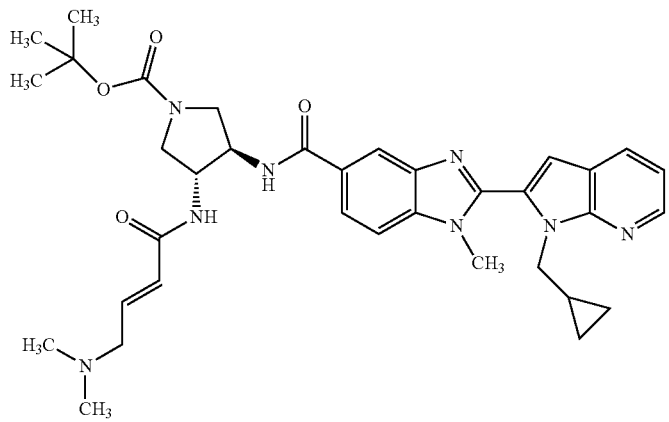

EV-AU3235-002

115 mg of trans-rac-tert-butyl (3R,4R)-3-{2-[1-(cyclopropylmethyl)-1H-pyrrolo[2,3-b]pyridin-2-yl]-1-methyl-1H-1,3-benzodiazole-5-amido}-4-[(2E)-4-(dimethylamino)but-2-enamido]pyrrolidine-1-carboxylate was purified by chiral HPLC (method E) to obtain 35 mg of trans-tert-butyl (3S,4S)-3-{2-[1-(cyclopropylmethyl)-1H-pyrrolo[2,3-b]pyridin-2-yl]-1-methyl-1H-1,3-benzodiazole-5-amido}-4-[(2E)-4-(dimethylamino)but-2-enamido]pyrrolidine-1-carboxylate EV-AU3235-001 (absolute stereochemistry arbitrarily assigned) and 39 mg of trans-tert-butyl (3R,4R)-3-{2-[1-(cyclopropylmethyl)-1H-pyrrolo[2,3-b]pyridin-2-yl]-1-methyl-1H-1,3-benzodiazole-5-amido}-4-[(2E)-4-(dimethylamino)but-2-enamido]pyrrolidine-1-carboxylate EV-AU3235-002 (absolute stereochemistry arbitrarily assigned).

EV-AU3235-001 Chiral purity (UV, 254 nm): 100%, retention time: 1.89 min (method F)

EV-AU3235-002 Chiral purity (UV, 254 nm): 99%, retention time: 2.27 min (method F)

Example 3. Synthesis of 2-[1-(Cyclopropylmethyl)-1H-pyrrolo[2,3-b]pyridin-2-yl]-N-[(3S,4S)-4-[(2E)-4-(dimethylamino)but-2-enamido]pyrrolidin-3-yl]-1-methyl-1H-1,3-benzodiazole-5-carboxamide trihydrochloride—I-5, EV-AU3253-001—Step 8

Scheme 1 Step 8

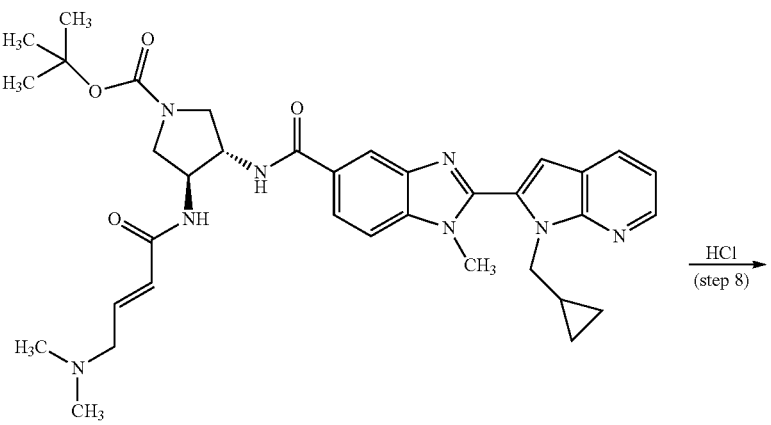

EV-AU3235-001

-continued

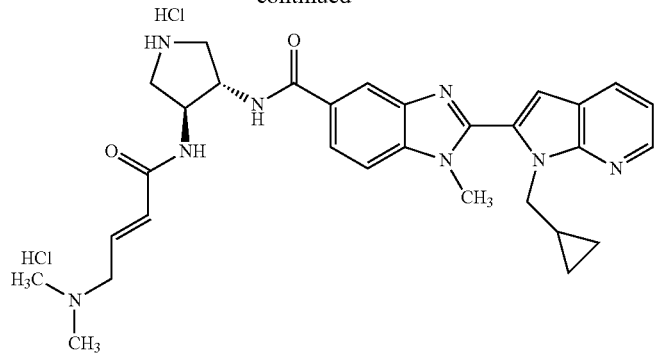

EV-AU3253-001

Tert-butyl (3S,4S)-3-{2-[1-(cyclopropylmethyl)-1H-pyrrolo[2,3-b]pyridin-2-yl]-1-methyl-1H-1,3-benzodiazole-5-amido}-4-[(2E)-4-(dimethylamino)but-2-enamido]pyrrolidine-1-carboxylate (EV-AU3253-001, 35 mg, 0.054 mmol) was treated as in step 8, Scheme 1 to obtain 35 mg (99%) of 2-[1-(cyclopropylmethyl)-1H-pyrrolo[2,3-b]pyridin-2-yl]-N-[(3S,4S)-4-[(2E)-4-(dimethylamino)but-2-enamido]pyrrolidin-3-yl]-1-methyl-1H-1,3-benzodiazole-5-carboxamide 1-5, EV-AU3253-001, as a white powder. LCMS (method A): retention time 1.43 min, M/z=541 (M+1).

Example 4. Synthesis of 2-[1-(Cyclopropylmethyl)-1H-pyrrolo[2,3-b]pyridin-2-yl]-N-[(3R,4R)-4-[(2E)-4-(dimethylamino)but-2-enamido]pyrrolidin-3-yl]-1-methyl-1H-1,3-benzodiazole-5-carboxamide trihydrochloride—I-4, EV-AU3254-001—Step 8

Scheme 1 Step 8

I-4

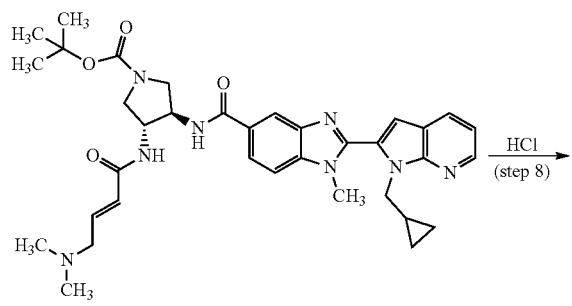

EV-AU3235-002

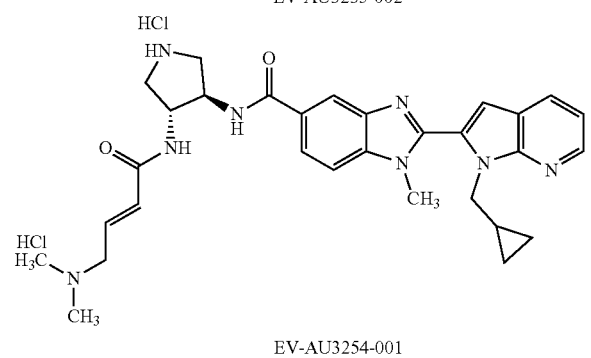

EV-AU3254-001

Tert-butyl (3R,4R)-3-{2-[1-(cyclopropylmethyl)-1H-pyrrolo[2,3-b]pyridin-2-yl]-1-methyl-1H-1,3-benzodiazole-5-amido}-4-[(2E)-4-(dimethylamino)but-2-enamido]pyrrolidine-1-carboxylate (EV-AU3254-001, 39 mg, 0.06 mmol) was treated as in step 8, Scheme 1 to obtain 39 mg (98%) of 2-[1-(cyclopropylmethyl)-1H-pyrrolo[2,3-b]pyridin-2-yl]-N-[(3R,4R)-4-[(2E)-4-(dimethylamino)but-2-enamido]pyrrolidin-3-yl]-1-methyl-1H-1,3-benzodiazole-5-carboxamide trihydrochloride 1-4, EV-AU3254-001, as an off-white powder. LCMS (method A): retention time 1.44 min, M/z=541 (M+1).

Special Cases for Scheme 1 (Schemes 1.1-1.9)

Example 5. Synthesis of Rac-2-[1-(cyclopropylmethyl)-1H-indol-2-yl]-N-[(3R,4R)-4-[(2E)-4-(dimethylamino)but-2-enamido]pyrrolidin-3-yl]-7-methoxy-1-methyl-1H-1,3-benzodiazole-5-carboxamide, I-2

Rac-2-[1-(cyclopropylmethyl)-1H-indol-2-yl]-N-[(3R,4R)-4-[(2E)-4-(dimethylamino)but-2-enamido]pyrrolidin-3-yl]-7-methoxy-1-methyl-1H-1,3-benzodiazole-5-carboxamide EV-AU9306-001 (EOAI3449033, I-2) was synthesised according to the procedures described in Scheme 1 via synthesis of methyl 3-amino-5-methoxy-4-(methylamino)benzoate EV-AR0068-002 as described in Scheme 1.1:

Scheme 1.1

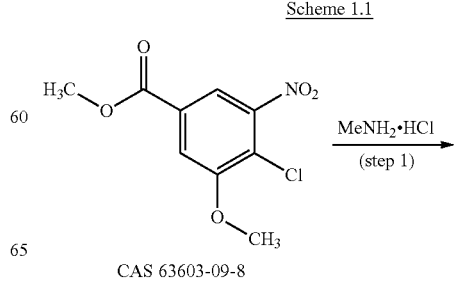

CAS 63603-09-8

-continued

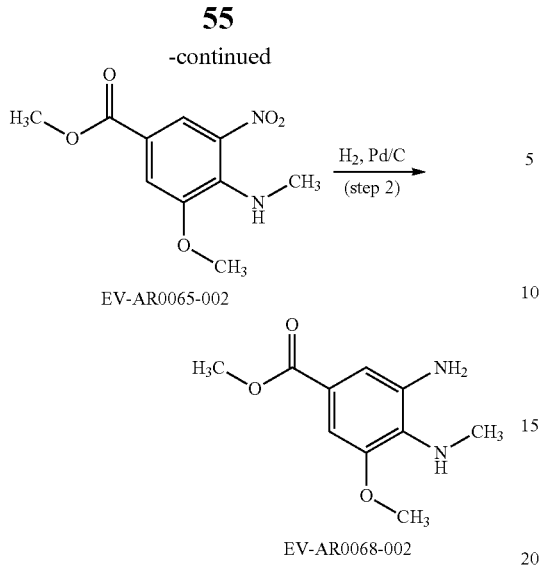

EV-AR0065-002

EV-AR0068-002

Methyl 3-methoxy-4-(methylamino)-5-nitrobenzoate EV-AR0065-002—Step 1

To a stirred solution of methyl 4-chloro-3-methoxy-5-nitrobenzoate (CAS 63603-09-8, 2.00 g, 8.14 mmol) in DMF (10 ml) was added $K_2CO_3$ (99%, 1.37 g, 9.81 mmol). To this solution was added methanamine hydrochloride (1:1) (0.62 g, 9.18 mmol) and the mixture was stirred in a sealed tube under nitrogen at 80° C. for 16 h. The reaction crude was concentrated in vacuo and partitioned between DCM (100 ml) and water (10 ml). The organic layer was washed further with water (2×10 ml) and saturated aqueous sodium chloride (10 ml). The organic layer was dried over sodium sulfate, filtered and concentrated in vacuo to afford an orange powder which was purified by flash column chromatography (15-40% EtOAc/heptane) to obtain 1.49 g (76%) of methyl 3-methoxy-4-(methylamino)-5-nitrobenzoate EV-AR0065-002 as an orange powder. LCMS (method D): retention time 1.13 min, M/z=241 (M+1).

Methyl 3-amino-5-methoxy-4-(methylamino)benzoate EV-AR0068-002—Step 2

To a stirred solution of methyl 3-methoxy-4-(methylamino)-5-nitrobenzoate (EV-AR0065-002, 1.49 g, 6.20 mmol) in ethanol (100 ml) under nitrogen was added 10% Pd/C (0.18 g, 0.17 mmol) and the resulting mixture was stirred at room temperature under an atmosphere of hydrogen for 16 h. The reaction mixture was filtered through Kieselguhr and the filter was washed through with methanol (150 ml). The filtrate was concentrated in vacuo to afford 1.21 g (89%) of methyl 3-amino-5-methoxy-4-(methylamino)benzoate EV-AR0068-002 as a pale purple powder. LCMS (method D): retention time 0.63 min, M/z=211 (M+1).

Example 6. Synthesis of Rac-(3R,4S)-4-{2-[1-(cyclopropylmethyl)-1H-pyrrolo[2,3-b]pyridin-2-yl]-1-methyl-1H-1,3-benzodiazole-5-amido}pyrrolidin-3-yl prop-2-enoate, I-11

Rac-(3R,4S)-4-{2-[1-(cyclopropylmethyl)-1H-pyrrolo[2,3-b]pyridin-2-yl]-1-methyl-1H-1,3-benzodiazole-5-amido}pyrrolidin-3-yl prop-2-enoate EV-AE3981-002 (EOAI3441779, I-11) was synthesised according to the procedures described in Scheme 1.2, steps 1 to 3, from 2-[1-(cyclopropylmethyl)-1H-pyrrolo[2,3-b]pyridin-2-yl]-1-methyl-1H-1,3-benzodiazole-5-carboxylic acid EV-AR3168-002 synthesised as described in Scheme 1:

Cis-rac-tert-butyl (3R,4S)-3-{2-[1-(cyclopropylmethyl)-1H-pyrrolo[2,3-b]pyridin-2-yl]-1-methyl-1H-1,3-benzodiazole-5-amido}-4-hydroxypyrrolidine-1-carboxylate EV-AE3975-001—Step 1

Scheme 1.2 Step 1

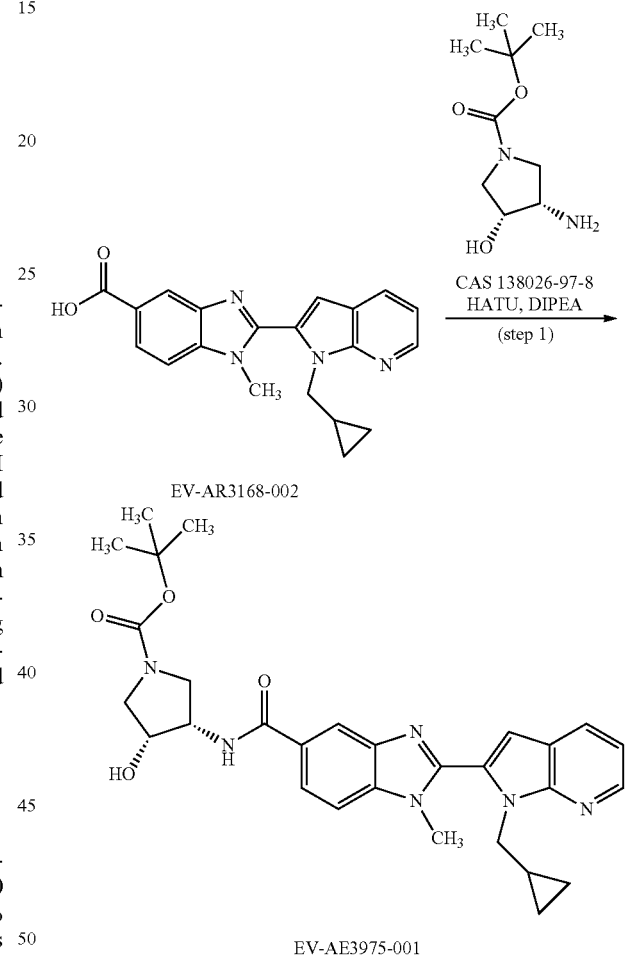

To a stirred solution of 2-[1-(cyclopropylmethyl)-1H-pyrrolo[2,3-b]pyridin-2-yl]-1-methyl-1H-1,3-benzodiazole-5-carboxylic acid (EV-AR3168-002, 100 mg, 0.29 mmol) and HATU (131 mg, 0.35 mmol) in DMF (3 ml) was added DIPEA (60 µl, 0.35 mmol). The resulting mixture was stirred at room temperature for 1 h then cis-rac-tert-butyl(3S,4R)-3-amino-4-hydroxypyrrolidine-1-carboxylate (CAS 138026-97-8, 70 mg, 0.35 mmol) was added and the reaction was continued for 2 h. The reaction was diluted with EtOAc (5 ml) and washed with water (5 ml). The organic layer was dried over sodium sulfate, filtered and concentrated in vacuo. The crude material was purified by flash column chromatography (0-5% MeOH/DCM) to afford 135 mg (84%) of cis-rac-tert-butyl 3-{2-[1-(cyclopropylmethyl)-1H-pyrrolo[2,3-b]pyridin-2-yl]-1-methyl-1H-1,3-benzodiazole-5-amido}-4-hydroxypyrrolidine-1-carboxylate EV-AE3975-001 as a tan powder. LCMS (method D); retention time 1.14 min, M/z=531 (M+1).

Cis-rac-tert-butyl 3-{2-[1-(cyclopropylmethyl)-1H-pyrrolo[2,3-b]pyridin-2-yl]-1-methyl-1H-1,3-benzodiazole-5-amido}-4-(prop-2-enoyloxy)pyrrolidine-1-carboxylate EV-AE3979-001—Step 2

Scheme 1.2 Step 2

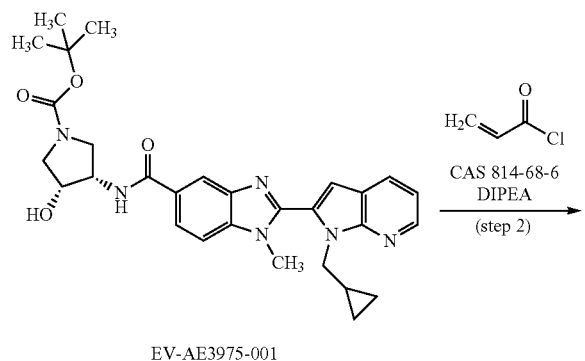

EV-AE3975-001

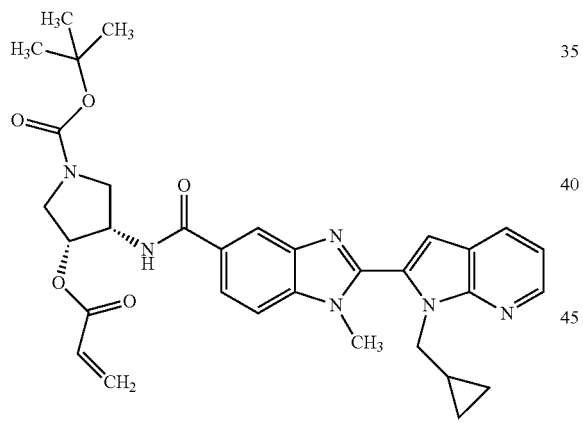

EV-AE3979-001

To a stirred solution of cis-rac-tert-butyl 3-{2-[1-(cyclopropylmethyl)-1H-pyrrolo[2,3-b]pyridin-2-yl]-1-methyl-1H-1,3-benzodiazole-5-amido}-4-hydroxypyrrolidine-1-carboxylate (EV-AE3975-001, 50 mg, 0.094 mmol) in DCM (1 ml) was added prop-2-enoyl chloride (CAS 814-68-6, 0.011 ml, 0.14 mmol) and DIPEA (0.025 ml, 0.14 mmol). The mixture was stirred at room temperature for 1 h. The reaction mixture was diluted with DCM (5 ml) and washed with water (2 ml) and brine (2 ml). The organic layer was dried over sodium sulfate, filtered and concentrated in vacuo. The crude material was purified by flash column chromatography (0-3% MeOH/DCM) to obtain 32 mg (58%) of cis-rac-tert-butyl 3-{2-[1-(cyclopropylmethyl)-1H-pyrrolo[2,3-b]pyridin-2-yl]-1-methyl-1H-1,3-benzodiazole-5-amido}-4-(prop-2-enoyloxy)pyrrolidine-1-carboxylate EV-AE3979-001 as a colourless oil. LCMS (method D): retention time 1.31 min, M/z=585 (M+1).

Cis-rac-(3R,4S)-4-{2-[1-(cyclopropylmethyl)-1H-pyrrolo[2,3-b]pyridin-2-yl]-1-methyl-1H-1,3-benzodiazole-5-amido}pyrrolidin-3-yl prop-2-enoate Hydrochloride EV-AE3981-002—Step 3

Scheme 1.2 Step 3

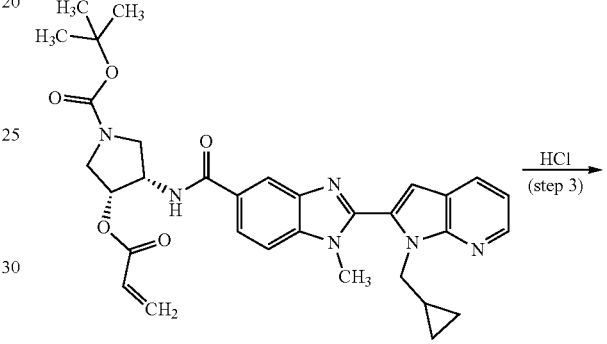

EV-AE3979-001

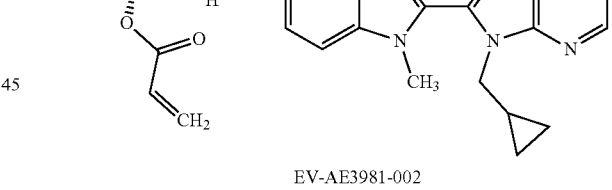

EV-AE3981-002

2M HCl in ether (0.23 ml, 0.57 mmol) was added to cis-rac-tert-butyl 3-{2-[1-(cyclopropylmethyl)-1H-pyrrolo[2,3-b]pyridin-2-yl]-1-methyl-1H-1,3-benzodiazole-5-amido}-4-(prop-2-enoyloxy)pyrrolidine1carboxylate (EV-AE3979-001, 30 mg, 0.057 mmol) and the resulting mixture was allowed to stand at room temperature for 2 h. The solvent was removed in vacuo and the solid azeotroped with DCM (1 ml). The solvent was removed in vacuo and the solid was dried to obtain 25 mg (83%) of cis-rac-(3R,4S)-4-{2-[1-(cyclopropylmethyl)-1H-pyrrolo[2,3-b]pyridin-2-yl]-1-methyl-1H-1,3-benzodiazole-5-amido}pyrrolidin-3-yl prop-2-enoate hydrochloride EV-AE3981-002 as an off white powder. LCMS (method A): retention time 1.96 min, M/z=485 (M+1).

Example 7. Synthesis of Cis-rac-2-[1-(cyclopropyl-methyl)-1H-pyrrolo[2,3-b]pyridin-2-yl]-N-[(3R,4R)-4-[(2E)-4-(dimethylamino)but-2-enamido]pyrroli-din-3-yl]-N,1-dimethyl-1H-1,3-benzodiazole-5-carboxamide, I-1

Cis-rac-2-[1-(cyclopropylmethyl)-1H-pyrrolo[2,3-b]pyridin-2-yl]-N-[(3R,4R)-4-[(2E)-4-(dimethylamino)but-2-enamido]pyrrolidin-3-yl]-N,1-dimethyl-1H-1,3-benzodiazole-5-carboxamide EV-AU3282-001 (EOAI3449646, I-1) was synthesised according to the procedures described in Scheme 1.3, steps 1 to 8, from tert-butyl 3-{2-[1-(cyclopropylmethyl)-1H-pyrrolo[2,3-b]pyridin-2-yl]-1-methyl-1H-1,3-benzodiazole-5-amido}-4-hydroxypyrrolidine-1-carboxylate EV-AU3248-001 synthesised as described in Scheme 1.2:

Cis-rac-tert-butyl (3R,4S)-3-[(tert-butyldimethylsi-lyl)oxy]-4-{2-[1-(cyclopropylmethyl)-1H-pyrrolo[2,3-b]pyridin-2-yl]-1-methyl-1H-1,3-benzodiazole-5-amido}pyrrolidine-1-carboxylate EV-AU3250-001—Step 1

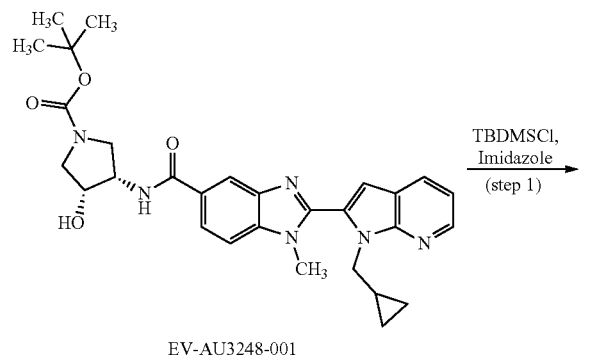

EV-AU3248-001

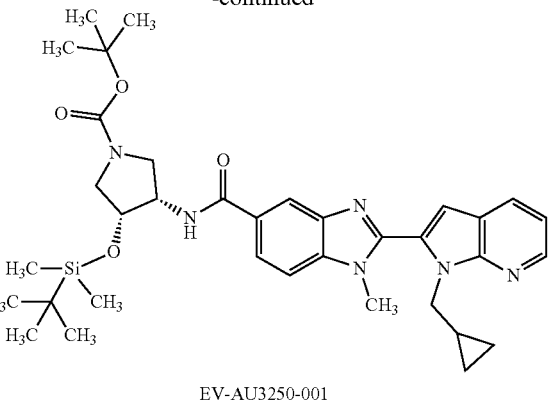

EV-AU3250-001

To a stirred solution of cis-rac-tert-butyl (3R,4S)-3-{2-[1-(cyclopropylmethyl)-1H-pyrrolo[2,3-b]pyridin-2-yl]-1-methyl-1H-1,3-benzodiazole-5-amido}-4-hydroxypyrrolidine-1-carboxylate (EV-AU3248-001, 820 mg, 1.55 mmol) in DMF (7.5 ml) was added imidazole (158 mg, 2.32 mmol) and TBDMSCl (280 mg, 1.85 mmol). The reaction was stirred at room temperature for 16 h. The reaction was diluted with water (20 ml) and extracted with EtOAc (3×10 ml). The combined organics were washed with water (2×20 ml), dried over sodium sulfate, filtered and concentrated in vacuo. The crude material was purified by flash column chromatography (50-100% EtOAc/heptanes) to obtain 638 mg (61%) of cis-rac-tert-butyl (3R,4S)-3-[(tert-butyldimethylsilyl)oxy]-4-{2-[1-(cyclopropylmethyl)-1H-pyrrolo[2,3-b]pyridin-2-yl]-1-methyl-1H-1,3-benzodiazole-5-amido}pyrrolidine-1-carboxylate EV-AU3250-001 as a colourless powder. LCMS (method D): retention time 1.55 min, M/z=645 (M+1).

Cis-rac-tert-butyl (3R,4S)-3-[(tert-butyldimethylsi-lyl)oxy]-4-{N-methyl2-[1-(cyclopropylmethyl)-1H-pyrrolo[2,3-b]pyridin-2-yl]-1-methyl-1H-1,3-benzo-diazole-5-amido}pyrrolidine-1-carboxylate EV-AU3257-001—Step 2

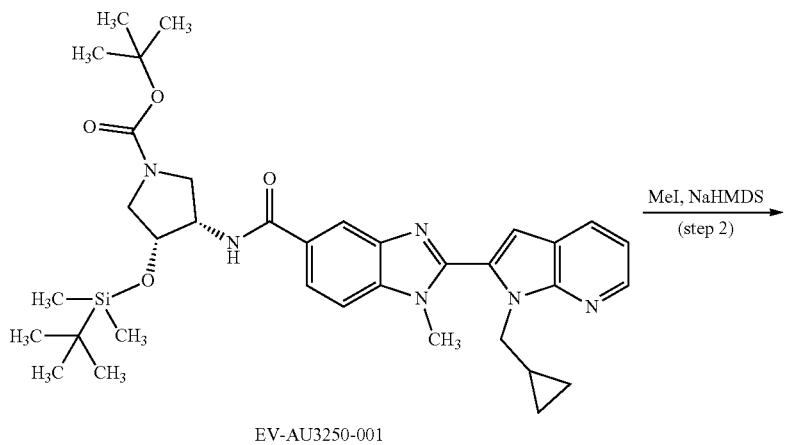

EV-AU3250-001

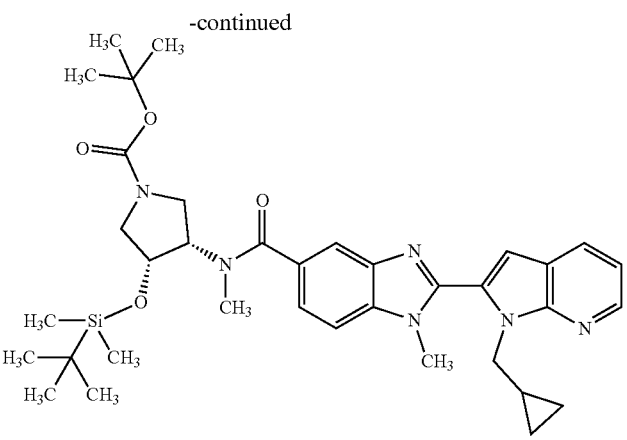

EV-AU3257-001

To a stirred solution of cis-rac-tert-butyl (3R,4S)-3-[(tert-butyldimethylsilyl)oxy]-4-{2-[1-(cyclopropylmethyl)-1H-pyrrolo[2,3-b]pyridin-2-yl]-1-methyl-1H-1,3-benzodiazole-5-amido}pyrrolidine-1-carboxylate (EV-AU3250-001, 630 mg, 0.98 mmol) in THF (12 ml) at −78° C. was added 2M NaHMDS in THF (1.47 ml) and the reaction was left to stir for 10 minutes. Iodomethane (0.36 ml, 5.86 mmol) was then added and the reaction was allowed to warm to room temperature while stirring for 3 h. The reaction mixture was diluted with diethyl ether (20 ml), washed with aq saturated sodium bicarbonate (10 ml) and then saturated aqueous sodium chloride (10 ml). The organic extract was then dried with sodium sulfate, filtered and concentrated under vacuum. The crude material was purified by flash column chromatography (40-100% EtOAc/heptanes) to obtain 470 mg (67%) of cis-rac-tert-butyl (3R,4S)-3-[(tert-butyldimethylsilyl)oxy]-4-{N-methyl2-[1-(cyclopropylmethyl)-1H-pyrrolo[2,3-b]pyridin-2-yl]-1-methyl-1H-1,3-benzodiazole-5-amido}pyrrolidine-1-carboxylate EV-AU3257-001 as a colourless powder. LCMS (method D): retention time 1.60 min, M/z=659 (M+1).

Cis-rac-tert-butyl (3R,4S)-3-hydroxy-4-{N-methyl2-[1-(cyclopropylmethyl)-1H-pyrrolo[2,3-b]pyridin-2-yl]-1-methyl-1H-1,3-benzodiazole-5-amido}pyrrolidine-1-carboxylate EV-AU3260-001—Step 3

Scheme 1.3 Step 3

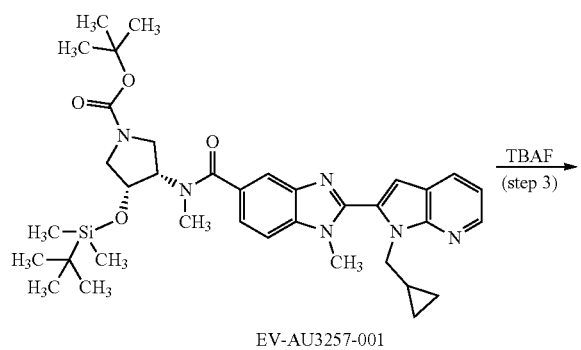

EV-AU3257-001

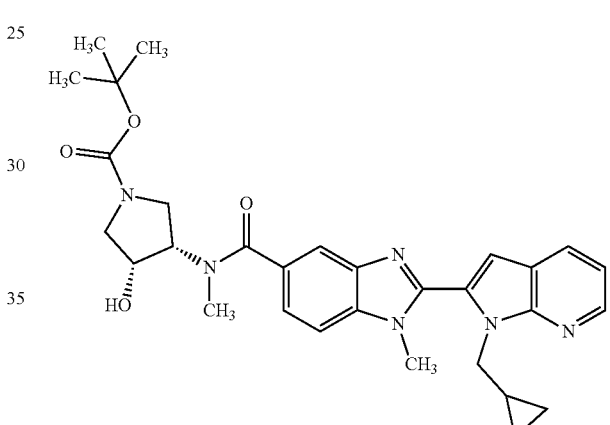

EV-AU3260-001

To a stirred solution of cis-rac-tert-butyl (3R,4S)-3-[(tert-butyldimethylsilyl)oxy]-4-{N-methyl2-[1-(cyclopropylmethyl)-1H-pyrrolo[2,3-b]pyridin-2-yl]-1-methyl-1H-1,3-benzodiazole-5-amido}pyrrolidine-1-carboxylate (EV-AU3257-001, 420 mg, 0.64 mmol) in THF (7 ml) at 0° C. was added 1M TBAF in THF (1.27 ml). The reaction was allowed to warm to room temperature and stirred for 1 h. The reaction mixture was diluted with EtOAc (10 ml), washed with water (3×10 ml) and saturated aqueous sodium chloride (10 ml). The organic extract was dried over sodium sulphate, filtered and concentrated under vacuo. The crude material was purified by flash column chromatography (0-10% MeOH/EtOAc) to obtain 379 mg (98%) of cis-rac-tert-butyl (3R,4S)-3-hydroxy-4-{N-methyl2-[1-(cyclopropylmethyl)-1H-pyrrolo[2,3-b]pyridin-2-yl]-1-methyl-1H-1,3-benzodiazole-5-amido}pyrrolidine-1-carboxylate EV-AU3260-001 as a colourless powder. LCMS (method D): retention time 1.18 min, M/z=545 (M+1).

Cis-rac-tert-butyl (3R,4S)-3-(methanesulfonyloxy)-4-{N-methyl2-[1-(cyclopropylmethyl)-1H-pyrrolo[2,3-b]pyridin-2-yl]-1-methyl-1H-1,3-benzodiazole-5-amido}pyrrolidine-1-carboxylate EV-AU3262-001—Step 4

Trans-rac-tert-butyl (3R,4R)-3-azido-4-{N-methyl2-[1-(cyclopropylmethyl)-1H-pyrrolo[2,3-b]pyridin-2-yl]-1-methyl-1H-1,3-benzodiazole-5-amido}pyrrolidine-1-carboxylate EV-AU3263-001—Step 5

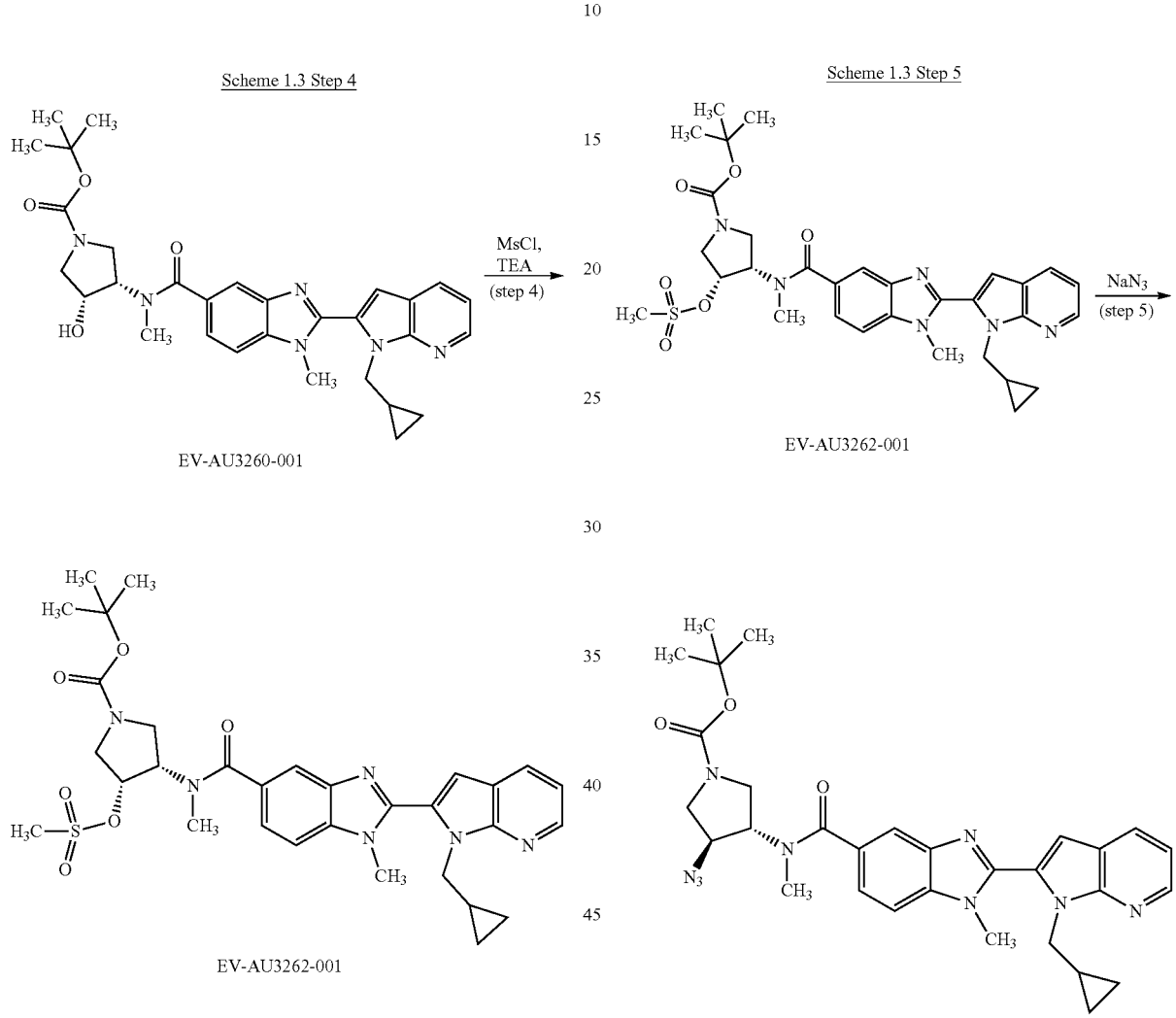

To a stirred solution of rac-tert-butyl (3R,4S)-3-hydroxy-4-{N-methyl2-[1-(cyclopropylmethyl)-1H-pyrrolo[2,3-b]pyridin-2-yl]-1-methyl-1H-1,3-benzodiazole-5-amido}pyrrolidine-1-carboxylate (EV-AU3260-001, 379 mg, 0.7 mmol) in DCM (10 ml) at 0° C. was added Et₃N (145 μl, 1.04 mmol) and MsCl (65 μl, 0.84 mmol). The reaction was allowed to reach room temperature while stirring for 2 h. The reaction mixture was washed with water (5 ml) and the organic layer was dried over sodium sulphate, filtered and concentrated under vacuum to obtain 410 mg (95%) of cis-rac-tert-butyl (3R,4S)-3-(methanesulfonyloxy)-4-{N-methyl2-[1-(cyclopropylmethyl)-1H-pyrrolo[2,3-b]pyridin-2-yl]-1-methyl-1H-1,3-benzodiazole-5-amido}pyrrolidine-1-carboxylate EV-AU3262-001 as a colourless powder. LCMS (method D): retention time 1.24 min, M/z=623 (M+1).

To a stirred solution of cis-rac-tert-butyl (3R,4S)-3-(methanesulfonyloxy)-4-{N-methyl2-[1-(cyclopropylmethyl)-1H-pyrrolo[2,3-b]pyridin-2-yl]-1-methyl-1H-1,3-benzodiazole-5-amido}pyrrolidine-1-carboxylate (EV-AU3262-001, 410 mg, 0.66 mmol) in DMSO (2 ml) was added sodium azide (128 mg, 1.98 mmol) and the reaction was stirred at 90° C. for 14 h. The reaction was then cooled to room temperature and diluted with EtOAc (10 ml). The solution was washed with water (3×10 ml), saturated aqueous sodium chloride (2×10 ml) and the organic extract was dried over sodium sulphate, filtered and concentrated in vacuo. The crude was purified by flash column chromatography (eluting with 50-100% EtOAc/heptanes) to obtain 272 mg (72%) of trans-rac-tert-butyl (3R,4R)-3-azido-4-{N- methyl2-[1-(cyclopropylmethyl)-1H-pyrrolo[2,3-b]pyridin-2-yl]-1-methyl-1H-1,3-benzodiazole-5-amido}pyrrolidine-1-carboxylate EV-AU3263-001 as a colourless powder. LCMS (method D): retention time 1.32 min, M/z=570 (M+1).

Trans-rac-tert-butyl (3R,4R)-3-amino-4-{N-methyl2-[1-(cyclopropylmethyl)-1H-pyrrolo[2,3-b]pyridin-2-yl]-1-methyl-1H-1,3-benzodiazole-5-amido}pyrrolidine-1-carboxylate EV-AU3267-001—Step 6

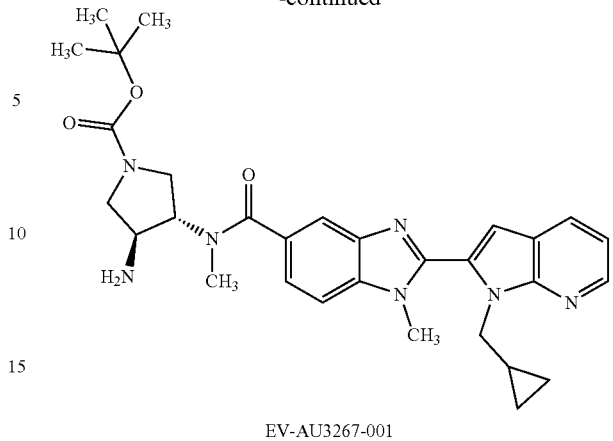

EV-AU3267-001

A solution of trans-rac-tert-butyl (3R,4R)-3-azido-4-{N-methyl2-[1-(cyclopropylmethyl)-1H-pyrrolo[2,3-b]pyridin-2-yl]-1-methyl-1H-1,3-benzodiazole-5-amido}pyrrolidine-1-carboxylate (EV-AU3263-001, 272 mg, 0.48 mmol) in EtOAc (8 ml) was stirred under a hydrogen atmosphere at room temperature for 12 h. The reaction mixture was filtered through a filter paper, the filter was washed with MeOH and the filtrate concentrated in vacuo to obtain 230 mg (80%) of trans-rac-tert-butyl (3R,4R)-3-amino-4-{N-methyl2-[1-(cyclopropylmethyl)-1H-pyrrolo[2,3-b]pyridin-2-yl]-1-methyl-1H-1,3-benzodiazole-5-amido}pyrrolidine-1-carboxylate EV-AU3267-001 as an off white powder. LCMS (method D): retention time 1.07 min, M/z=544 (M+1).

Trans-rac-tert-butyl (3R,4R)-3-[(2E)-4-(dimethylamino)but-2-enamido]-4-{N-methyl2-[1-(cyclopropylmethyl)-1H-pyrrolo[2,3-b]pyridin-2-yl]-1-methyl-1H-1,3-benzodiazole-5-amido}pyrrolidine-1-carboxylate EV-AU3279-001—Step 7

Scheme 1.3 Step 6

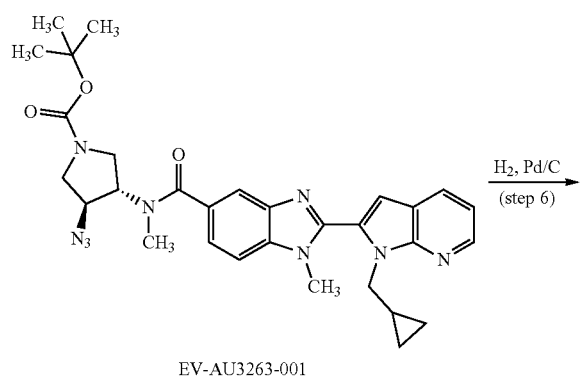

EV-AU3263-001

Scheme 1.3 Step 7

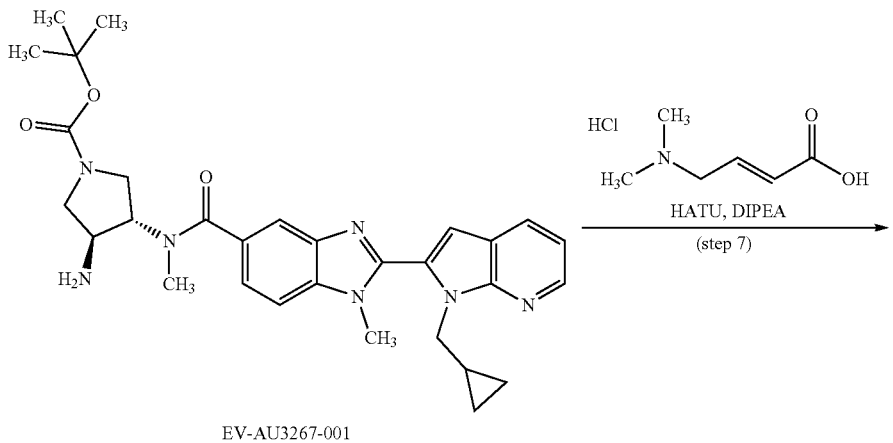

EV-AU3267-001

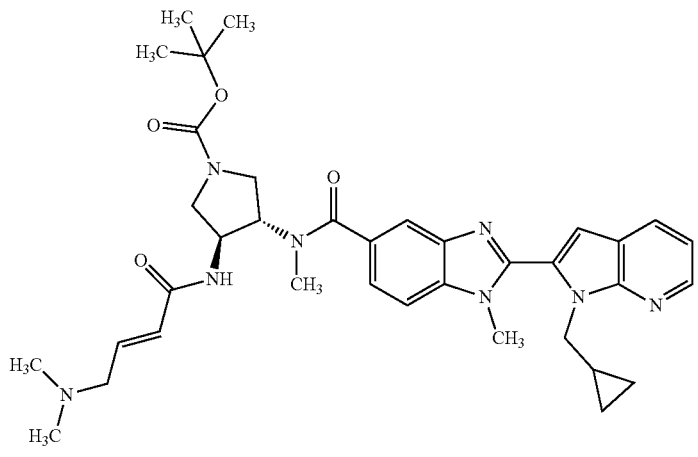

EV-AU3279-001

To a stirred solution of trans-rac-tert-butyl (3R,4R)-3-amino-4-{N-methyl2-[1-(cyclopropylmethyl)-1H-pyrrolo[2,3-b]pyridin-2-yl]-1-methyl-1H-1,3-benzodiazole-5-amido}pyrrolidine-1-carboxylate (EV-AU3267-001, 70 mg, 0.13 mmol) and (2E)-4-(dimethylamino)but-2-enoic acid hydrochloride (26 mg, 0.15 mmol) in DMF (1 ml) was added HATU (59 mg, 0.15 mmol) and DIPEA (49 µl, 0.28 mmol) and the reaction was stirred at room temperature for 2 h. The solvent was then removed under vacuum and the crude was purified by preparative HPLC (acidic method) to give 20 mg (24%) of trans-rac-tert-butyl (3R,4R)-3-[(2E)-4-(dimethylamino)but-2-enamido]-4-{N-methyl2-[1-(cyclopropylmethyl)-1H-pyrrolo[2,3-b]pyridin-2-yl]-1-methyl-1H-1,3-benzodiazole-5-amido}pyrrolidine-1-carboxylate EV-AU3279-001 as an off white solid. LCMS (method D); retention time 1.14 min, M/z=655 (M+1).

Trans-rac-2-[1-(cyclopropylmethyl)-1H-pyrrolo[2,3-b]pyridin-2-yl]-N-[(3R,4R)-4-[(2E)-4-(dimethylamino)but-2-enamido]pyrrolidin-3-yl]-N,1-dimethyl-1H-1,3-benzodiazole-5-carboxamide Hydrochloride, I-1 (EV-AU3282-001)—Step 8

Scheme 1.3 Step 8

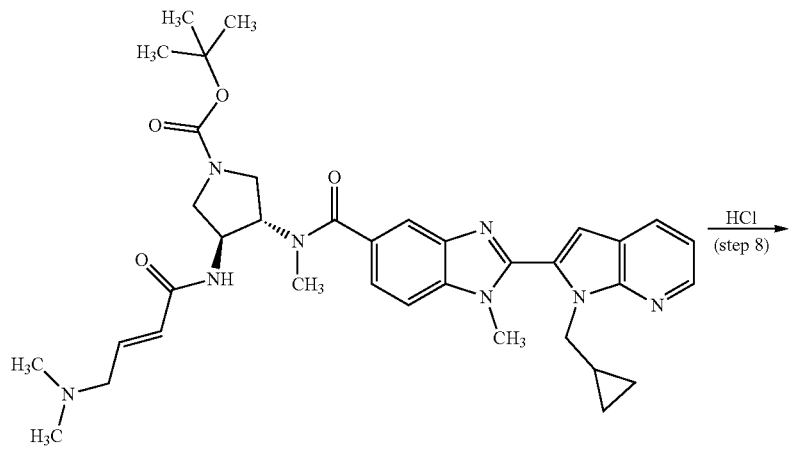

EV-AU3279-001

-continued

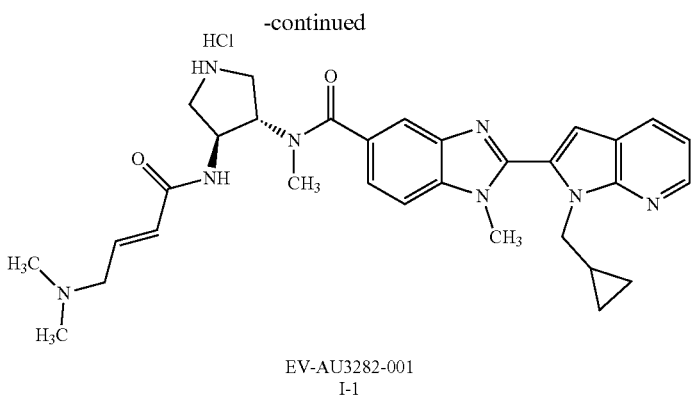

EV-AU3282-001
I-1

2M HCl in diethyl ether (0.76 ml) was added to trans-rac-tert-butyl (3R,4R)-3-[(2E)-4-(dimethylamino)but-2-enamido]-4-{N-methyl2-[1-(cyclopropylmethyl)-1H-pyrrolo[2,3-b]pyridin-2-yl]-1-methyl-1H-1,3-benzodiazole-5-amido}pyrrolidine-1-carboxylate (EV-AU3279-001, 20 mg, 0.03 mmol) and the resulting mixture was stirred at room temperature for 2 h. The reaction mixture was concentrated in vacuo to obtain 17 mg (78%) of rac-2-[1-(cyclopropylmethyl)-1H-pyrrolo[2,3-b]pyridin-2-yl]-N-[(3R,4R)-4-[(2E)-4-(dimethylamino)but-2-enamido]pyrrolidin-3-yl]-N,1-dimethyl-1H-1,3-benzodiazole-5-carboxamide hydrochloride I-1 (EV-AU3282-001) as an off white solid. LCMS (method A); retention time 1.43 min, M/z=555 (M+1).

Example 8. Synthesis of Cis-rac-(2E)-N-[(3R,4S)-3-amino-1-{2-[1-(cyclopropylmethyl)-1H-pyrrolo[2,3-b]pyridin-2-yl]-1-methyl-1H-1,3-benzodiazole-5-carbonyl}piperidin-4-yl]-4-(dimethylamino)but-2-enamide, I-3

Cis-rac-(2E)-N-[(3R,4S)-3-amino-1-{2-[1-(cyclopropylmethyl)-1H-pyrrolo[2,3-b]pyridin-2-yl]-1-methyl-1H-1,3-benzodiazole-5-carbonyl}piperidin-4-yl]-4-(dimethylamino)but-2-enamide EV-AU3261-001 (EOAI3449030, I-3) was synthesised according to the procedures described in Scheme 1.4, steps 1 to 10, using intermediate methyl 2-[1-(cyclopropylmethyl)-1H-pyrrolo[2,3-b]pyridin-2-yl]-1-methyl-1H-1,3-benzodiazole-5-carboxylate EV-AR6658-001 synthesised as described in Scheme 1:

Trans-rac-tert-butyl (3R,4R)-3-{[(benzyloxy)carbonyl]amino}-4-hydroxypiperidine-1-carboxylate EV-AU3233-001—Step 1

Scheme 1.4 Step 1

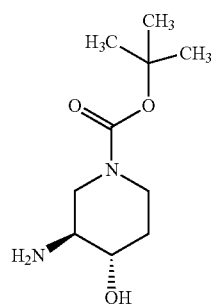

+

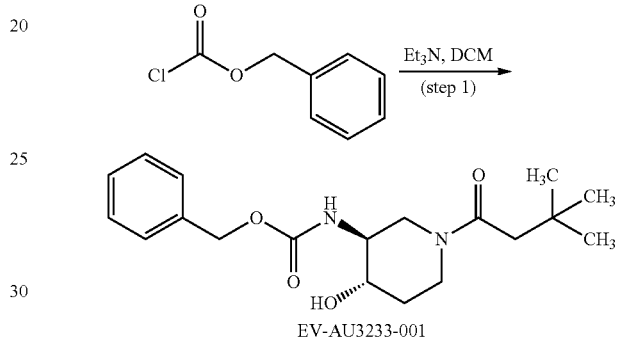

EV-AU3233-001

To a solution of trans-rac-tert-butyl (3R,4R)-3-amino-4-hydroxypiperidine-1-carboxylate (250 mg, 1.16 mmol) in DCM (5 ml) at 0° C. was added triethylamine (484 μl, 3.47 mmol) and benzyl chloroformate (198 μl, 1.39 mmol). The reaction mixture was left to stir at 0° C. for 15 minutes. The solution was allowed to warm to room temperature and stirred for a further 12 h. The reaction was quenched with water (10 ml) and extracted with DCM (3×10 ml). The combined organic fractions were dried with sodium sulfate, filtered and concentrated under vacuum. The crude product was purified by column chromatography (20-80% EtOAc/heptanes) to obtain 0.21 g (52%) of trans-rac-tert-butyl (3R,4R)-3-{[(benzyloxy)carbonyl]amino}-4-hydroxypiperidine-1-carboxylate EV-AU3233-001 as a colourless viscous oil. LCMS (method D): retention time 1.12 min, M/z=373 (M+Na).

Trans-rac-benzyl N-[(3R,4R)-4-hydroxypiperidin-3-yl]carbamate Hydrochloride EV-AU3238-001—Step 2

Scheme 1.4 Step 2

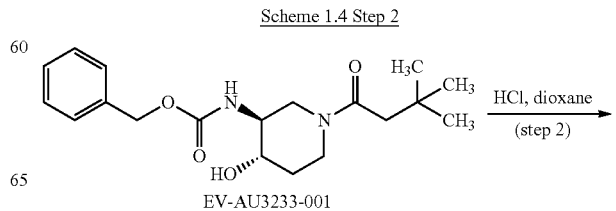

EV-AU3233-001

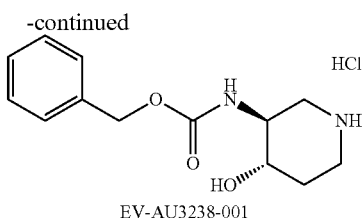

EV-AU3238-001

Trans-rac-tert-butyl (3R,4R)-3-{[(benzyloxy)carbonyl]amino}-4-hydroxypiperidine-1-carboxylate (EV-AU3233-001 and EV-AU3236-001 combined, 390 mg, 1.11 mmol) was dissolved in 4M HCl in dioxane (5.56 ml) and stirred at room temperature for 1 h. The solvent was removed under vacuum to obtain 0.27 g (86%) of trans-rac-benzyl N-[(3R,4R)-4-hydroxypiperidin-3-yl]carbamate hydrochloride EV-AU3238-001 as a white solid. LCMS (method D): retention time 0.64 min, M/z=251 (M+1).

Trans-rac-benzyl N-[(3R,4R)-1-{2-[1-(cyclopropylmethyl)-1H-pyrrolo[2,3-b]pyridin-2-yl]-1-methyl-1H-1,3-benzodiazole-5-carbonyl}-4-hydroxypiperidin-3-yl]carbamate EV-AU3240-001—Step 3

To a solution of methyl 2-[1-(cyclopropylmethyl)-1H-pyrrolo[2,3-b]pyridin-2-yl]-1-methyl-1H-1,3-benzodiazole-5-carboxylate (EV-AR6658-001, 330 mg, 0.95 mmol) in DMF (5 ml) was added DIPEA (0.55 ml, 3.33 mmol) and HATU (435 mg, 1.14 mmol) and the reaction was stirred under nitrogen at room temperature for 1 h. Benzyl N-[(3R,4R)-4-hydroxypiperidin-3-yl]carbamate hydrochloride (273 mg, 0.95 mmol) was added and the reaction was stirred for a further 2 h at room temperature. The reaction was quenched with water (5 ml) and extracted with ethyl acetate (5 ml×3). The combined organic extracts were washed with water (5 ml) and saturated aqueous sodium chloride (2×5 ml), dried with sodium sulfate, filtered and concentrated under vacuum. The crude was purified by column chromatography (50-100% EtOAc/heptanes, followed by 0-20% MeOH/EtOAc) to obtain 0.48 g (70%) of trans-rac-benzyl N-[(3R,4R)-1-{2-[1-(cyclopropylmethyl)-1H-pyrrolo[2,3-b]pyridin-2-yl]-1-methyl-1H-1,3-benzodiazole-5-carbonyl}-4-hydroxypiperidin-3-yl]carbamate EV-AU3240-001 as a colourless viscous oil. LCMS (method D): retention time 1.11 min, M/z=579 (M+1).

Scheme 1.4 Step 3

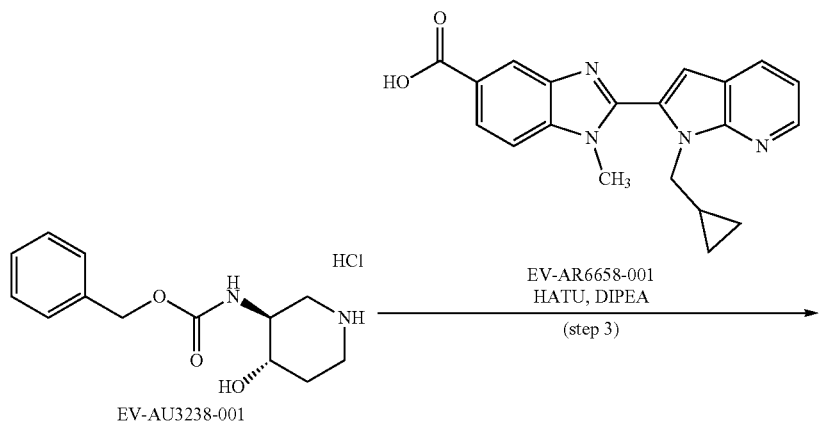

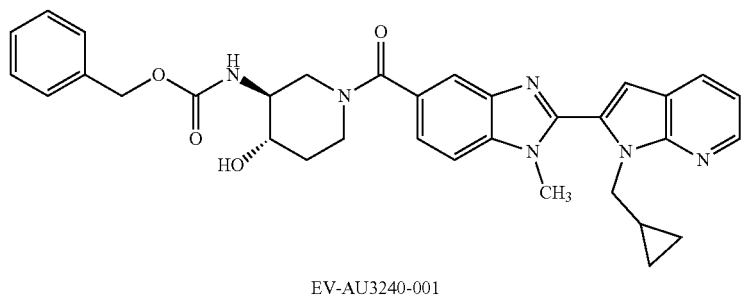

EV-AU3240-001

Trans-rac-(3R,4R)-3-amino-1-{2-[1-(cyclopropylmethyl)-1H-pyrrolo[2,3-b]pyridin-2-yl]-1-methyl-1H-1,3-benzodiazole-5-carbonyl}piperidin-4-ol EV-AU3242-001—Step 4

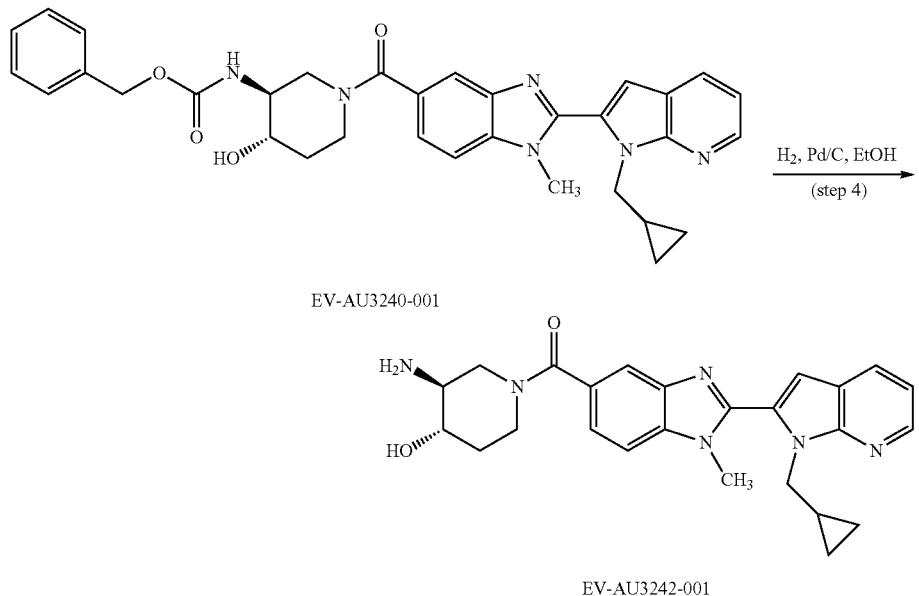

EV-AU3240-001

EV-AU3242-001

A solution of trans-rac-benzyl N-[(3R,4R)-1-{2-[1-(cyclopropylmethyl)-1H-pyrrolo[2,3-b]pyridin-2-yl]-1-methyl-1H-1,3-benzodiazole-5-carbonyl}-4-hydroxypiperidin-3-yl] carbamate (EV-AU3240-001, 480 mg, 0.83 mmol) in ethanol (10 ml) was stirred at room temperature for 12 h under a hydrogen atmosphere in the presence of Pd/C (5%, 176.55 mg, 0.08 mmol). The reaction was filtered through a Kieselguhr pad, the filter was washed with MeOH and concentrated under vacuum to obtain 0.38 g (90%) of trans-rac-(3R,4R)-3-amino-1-{2-[1-(cyclopropylmethyl)-1H-pyrrolo[2,3-b]pyridin-2-yl]-1-methyl-1H-1,3-benzodiazole-5-carbonyl}piperidin-4-ol EV-AU3242-001 as a white solid. LCMS (method D): retention time 0.90 min, M/z=445 (M+1).

Trans-rac-tert-butyl N-[(3R,4R)-1-{2-[1-(cyclopropylmethyl)-1H-pyrrolo[2,3-b]pyridin-2-yl]-1-methyl-1H-1,3-benzodiazole-5-carbonyl}-4-hydroxypiperidin-3-yl]carbamate EV-AU3245-001—Step 5

Scheme 1.4 Step 5

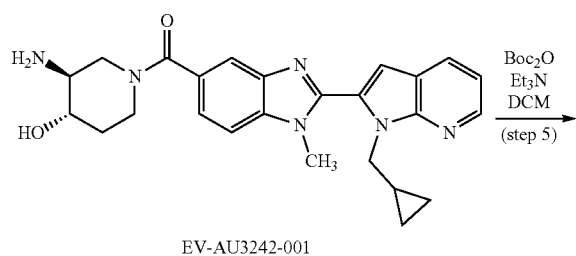

EV-AU3242-001

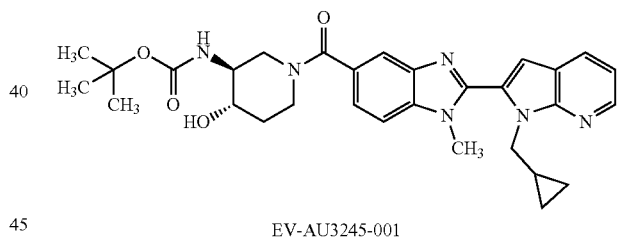

EV-AU3245-001

To a solution of trans-rac-(3R,4R)-3-amino-1-{2-[1-(cyclopropylmethyl)-1H-pyrrolo[2,3-b]pyridin-2-yl]-1-methyl-1H-1,3-benzodiazole-5-carbonyl}piperidin-4-ol (EV-AU3242-001, 87%, 380 mg, 0.74 mmol) in DCM (5 ml) was added triethylamine (114 µl, 0.82 mmol) and di-tert-butyl dicarbonate (178 mg, 0.82 mmol) and the reaction was stirred at room temperature for 1 h. The reaction was quenched with saturated aqueous sodium bicarbonate and extracted with DCM (10 ml). The aqueous layer was washed with DCM (10 ml) and the combined organic extracts were dried over sodium sulfate, filtered and concentrated under vacuum to obtain 0.27 g (63%) of trans-rac-tert-butyl N-[(3R,4R)-1-{2-[1-(cyclopropylmethyl)-1H-pyrrolo[2,3-b]pyridin-2-yl]-1-methyl-1H-1,3-benzodiazole-5-carbonyl}-4-hydroxypiperidin-3-yl]carbamate EV-AU3245-001 as a white solid. LCMS (method D): retention time 1.09 min, M/z=545 (M+1).

Trans-rac-tert-butyl N-[(3R,4R)-1-{2-[1-(cyclopropylmethyl)-1H-pyrrolo[2,3-b]pyridin-2-yl]-1-methyl-1H-1,3-benzodiazole-5-carbonyl}-4-(methanesulfonyloxy)piperidin-3-yl]carbamate EV-AU3251-001—Step 6

Scheme 1.4 Step 6

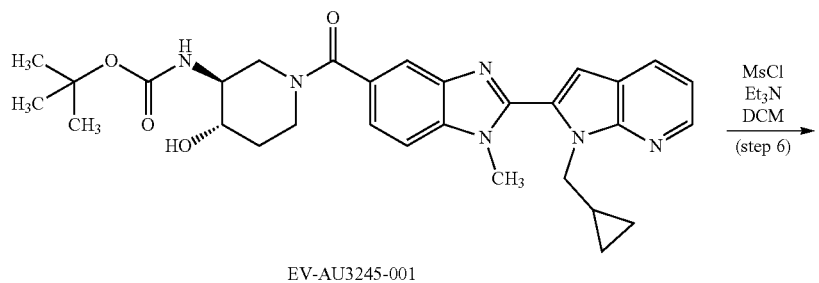

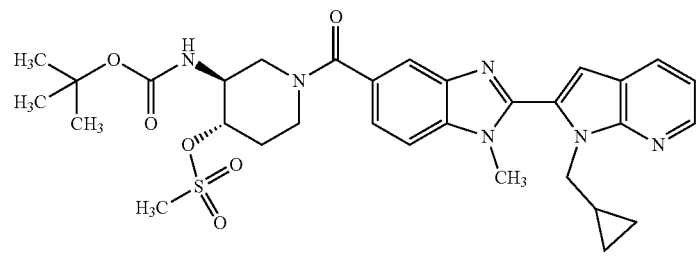

EV-AU3251-001

To a solution of trans-rac-tert-butyl N-[(3R,4R)-1-{2-[1-(cyclopropylmethyl)-1H-pyrrolo[2,3-b]pyridin-2-yl]-1-methyl-1H-1,3-benzodiazole-5-carbonyl}-4-hydroxypiperidin-3-yl]carbamate (EV-AU3245-001, 269 mg, 0.49 mmol) in DCM (8 ml) at 0° C. was added triethylamine (103 µl, 0.74 mmol) and mesyl chloride (46 µl, 0.59 mmol). The reaction was stirred and allowed to reach room temperature over 2 h. The reaction mixture was washed with water (5 ml) and the organic layer was dried over sodium sulfate, filtered and concentrated under vacuum to obtain 0.31 g (81%) of trans-rac-tert-butyl N-[(3R,4R)-1-{2-[1-(cyclopropylmethyl)-1H-pyrrolo[2,3-b]pyridin-2-yl]-1-methyl-1H-1,3-benzodiazole-5-carbonyl}-4-(methanesulfonyloxy)piperidin-3-yl]carbamate EV-AU3251-001 as a colourless viscous oil. LCMS (method D): retention time 1.18 min, M/z=623 (M+1).

Cis-rac-tert-butyl N-[(3R,4S)-4-azido-1-{2-[1-(cyclopropylmethyl)-1H-pyrrolo[2,3-b]pyridin-2-yl]-1-methyl-1H-1,3-benzodiazole-5-carbonyl}piperidin-3-yl]carbamate EV-AU3252-001—Step 7

Scheme 1.4 Step 7

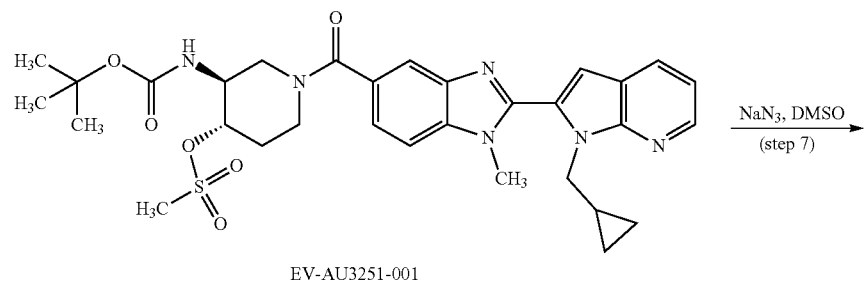

EV-AU3251-001

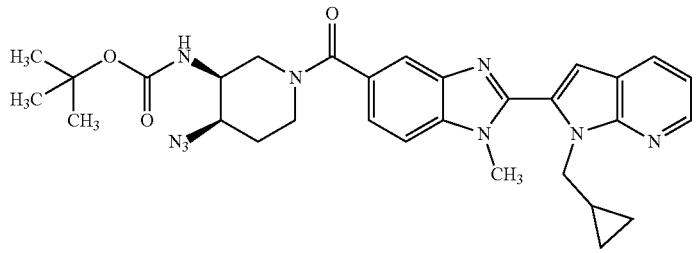

EV-AU3252-001

To a solution of trans-rac-tert-butyl N-[(3R,4R)-1-{2-[1-(cyclopropylmethyl)-1H-pyrrolo[2,3-b]pyridin-2-yl]-1-methyl-1H-1,3-benzodiazole-5-carbonyl}-4-(methanesulfonyloxy)piperidin-3-yl]carbamate (EV-AU3251-001, 313 mg, 0.5 mmol) in DMSO (1.5 ml) was added sodium azide (98 mg, 1.51 mmol) and the reaction was left to stir at 90° C. for 14 h. The reaction was cooled to room temperature and diluted with EtOAc (10 ml). The organic layer was washed with water (3×10 ml) and saturated aqueous sodium chloride (2×10 ml). The organic extract was dried over sodium sulfate, filtered and concentrated under vacuum. The crude was purified by column chromatography (50-100% EtOAc/heptanes) to obtain 0.12 g (43%) of cis-rac-tert-butyl N-[(3R,4S)-4-azido-1-{2-[1-(cyclopropylmethyl)-1H-pyrrolo[2,3-b]pyridin-2-yl]-1-methyl-1H-1,3-benzodiazole-5-carbonyl}piperidin-3-yl]carbamate EV-AU3252-001 as a white solid. LCMS (method D); retention time 1.25 min, M/z=570 (M+1).

Cis-rac-tert-butyl N-[(3R,4S)-4-amino-1-{2-[1-(cyclopropylmethyl)-1H-pyrrolo[2,3-b]pyridin-2-yl]-1-methyl-1H-1,3-benzodiazole-5-carbonyl}piperidin-3-yl]carbamate EV-AU3256-001—Step 8

Scheme 1.4 Step 8

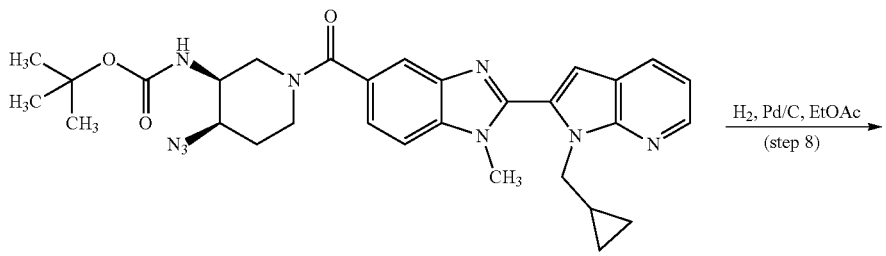

EV-AU3252-001

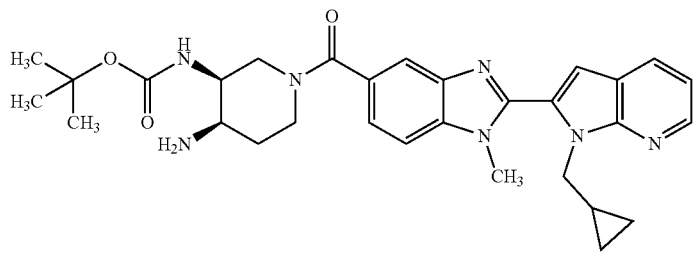

EV-AU3256-001

A solution of cis-rac-tert-butyl N-[(3R,4S)-4-azido-1-{2-[1-(cyclopropylmethyl)-1H-pyrrolo[2,3-b]pyridin-2-yl]-1-methyl-1H-1,3-benzodiazole-5-carbonyl}piperidin-3-yl]carbamate (EV-AU3252-001, 125 mg, 0.22 mmol) in EtOAc (4 ml) was treated with Pd/C (5% w/w, 47 mg, 0.02 mmol) and stirred under one atmosphere of hydrogen for 12 h. The crude mixture was filtered through glass fibre filter paper, the filter was washed with MeOH and the filtrate concentrated to obtain 0.10 g (85%) of cis-rac-tert-butyl N-[(3R,4S)-4-amino-1-{2-[1-(cyclopropylmethyl)-1H-pyrrolo[2,3-b]pyridin-2-yl]-1-methyl-1H-1,3-benzodiazole-5-carbonyl}piperidin-3-yl]carbamate EV-AU3256-001 as an off white solid. LCMS (method D): retention time 0.98 min, M/z=544 (M+1).

Cis-rac-tert-butyl N-[(3R,4S)-1-{2-[1-(cyclopropylmethyl)-1H-pyrrolo[2,3-b]pyridin-2-yl]-1-methyl-1H-1,3-benzodiazole-5-carbonyl}-4-[(2E)-4-(dimethylamino)but-2-enamido]piperidin-3-yl]carbamate EV-AU3258-001—Step 9

Scheme 1.4 Step 9

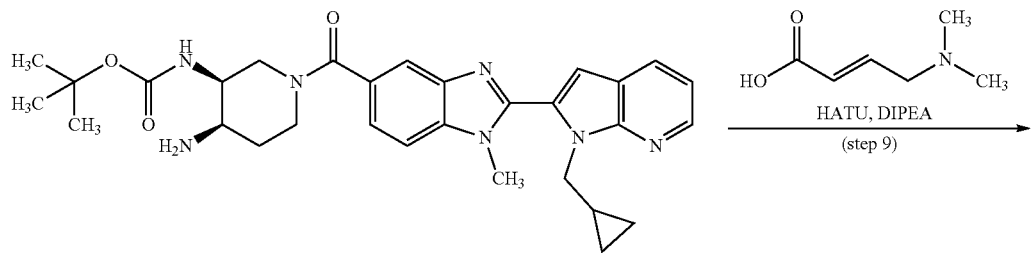

EV-AU3256-001

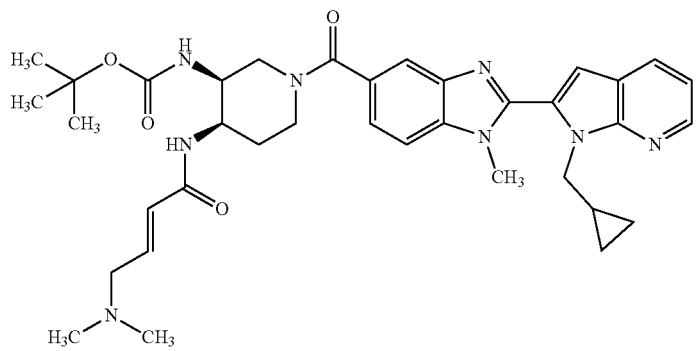

EV-AU3258-001

To a solution of (2E)-4-(dimethylamino)but-2-enoic acid hydrochloride (18 mg, 0.11 mmol) and cis-rac-tert-butyl N-[(3R,4S)-4-amino-1-{2-[1-(cyclopropylmethyl)-1H-pyrrolo[2,3-b]pyridin-2-yl]-1-methyl-1H-1,3-benzodiazole-5-carbonyl}piperidin-3-yl]carbamate (EV-AU3256-001, 50 mg, 0.09 mmol) in DMF (1 ml) were added HATU (42 mg, 0.11 mmol) and DIPEA (35 µl, 0.2 mmol) and the reaction was stirred at room temperature for 2 h. The solvent was removed under vacuum and the crude purified by preparative HPLC (acidic method) to obtain 25 mg (37%) of cis-rac-tert-butyl N-[(3R,4S)-1-{2-[1-(cyclopropylmethyl)-1H-pyrrolo[2,3-b]pyridin-2-yl]-1-methyl-1H-1,3-benzodiazole-5-carbonyl}-4-[(2E)-4-(dimethylamino)but-2-enamido]piperidin-3-yl]carbamate EV-AU3258-001 as an off white solid. LCMS (method D): retention time 2.12 min, M/z=655 (M+1).

Cis-rac-(2E)-N-[(3R,4S)-3-amino-1-{2-[1-(cyclopropylmethyl)-1H-pyrrolo[2,3-b]pyridin-2-yl]-1-methyl-1H-1,3-benzodiazole-5-carbonyl}piperidin-4-yl]-4-(dimethylamino)but-2-enamide, I-3 (EV-AU3261-001)—Step 10

Cis-rac-tert-butyl N-[(3R,4S)-1-{2-[1-(cyclopropylmethyl)-1H-pyrrolo[2,3-b]pyridin-2-yl]-1-methyl-1H-1,3-benzodiazole-5-carbonyl}-4-[(2E)-4-(dimethylamino)but-2-enamido]piperidin-3-yl]carbamate (EV-AU3258-001, 25 mg, 0.04 mmol) was dissolved in 2M HCl in diethyl ether (1.93 ml) and left to stir at room temperature for 2 h. The solvent was removed under vacuum to obtain 18 mg (75%) of cis-rac-(2E)-N-[(3R,4S)-3-amino-1-{2-[1-(cyclopropylmethyl)-1H-pyrrolo[2,3-b]pyridin-2-yl]-1-methyl-1H-1,3-benzodiazole-5-carbonyl}piperidin-4-yl]-4-(dimethylamino)but-2-enamide I-3 (EV-AU3261-001) as an off white solid. LCMS (method A): retention time 1.48 min, M/z=555 (M+1).

Example 9. Synthesis of Cis-rac-2-[1-(cyclopropylmethyl)-1H-pyrrolo[2,3-b]pyridin-2-yl]-N-[(3R,5S)-5-[(2E)-4-(dimethylamino)but-2-enamido]piperidin-3-yl]-1-methyl-1H-1,3-benzodiazole-5-carboxamide, I-8

Cis-rac-2-[1-(cyclopropylmethyl)-1H-pyrrolo[2,3-b]pyridin-2-yl]-N-[(3R,5S)-5-[(2E)-4-(dimethylamino)but-2-enamido]piperidin-3-yl]-1-methyl-1H-1,3-benzodiazole-5-carboxamide EV-AE3994-001 (EOAI3447033, I-8) was synthesised according to the procedures described in Scheme 1.5, steps 1 to 3, from 2-[1-(cyclopropylmethyl)-

Scheme 1.4 Step 10

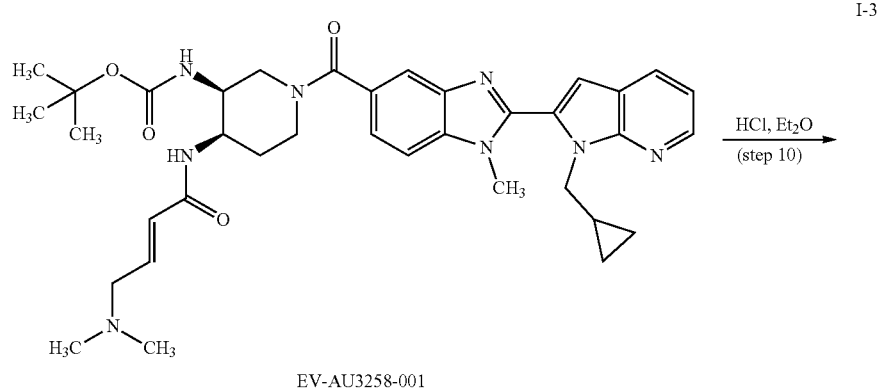

EV-AU3258-001

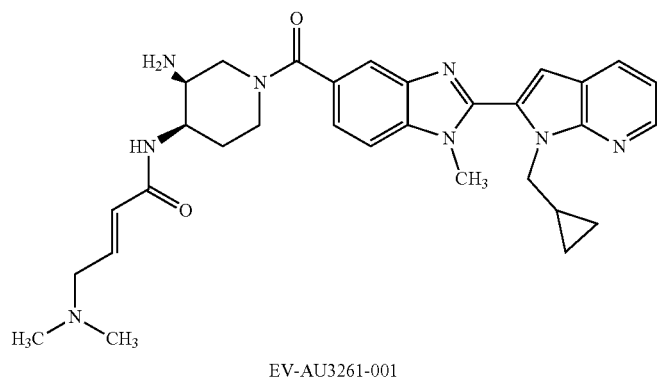

EV-AU3261-001

1H-pyrrolo[2,3-b]pyridin-2-yl]-1-methyl-1H-1,3-benzodiazole-5-carboxylic acid EV-AR6658-001 synthesised as described in Scheme 1:

Cis-rac-tert-butyl (3R,5S)-3-amino-5-{2-[1-(cyclopropylmethyl)-1H-pyrrolo[2,3-b]pyridin-2-yl]-1-methyl-1H-1,3-benzodiazole-5-amido}piperidine-1-carboxylate EV-AE3991-001—Step 1

Scheme 1.5 Step 1

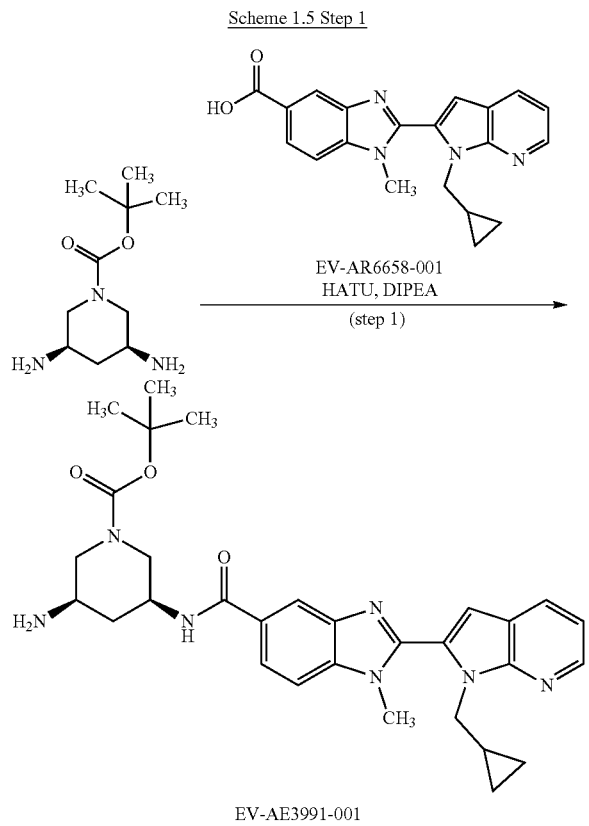

To a solution of 2-[1-(cyclopropylmethyl)-1H-pyrrolo[2,3-b]pyridin-2-yl]-1-methyl-1H-1,3-benzodiazole-5-carboxylic acid (EV-AR6658-001, prepared as in Scheme 1, 100 mg, 0.14 mmol) in DMF (1 ml) was added DIPEA (167 μl, 1.01 mmol) and HATU (132 mg, 0.35 mmol) and the reaction was left to stir under nitrogen at room temperature for 20 minutes. Cis-rac-tert-butyl (3R,5S)-3,5-diaminopiperidine-1-carboxylate (EV-AU3202-001 prepared as described in *J. Org. Chem.*, 2013, 78(23), p 12236-12242), 155 mg, 0.72 mmol) in DMF (1 ml) was added and the reaction was stirred for a further 2 h at room temperature. The reaction was quenched with water (5 ml) and extracted with ethyl acetate (5 ml×3). The combined organic extracts were washed with saturated aqueous sodium chloride (5 ml), dried over sodium sulfate, filtered and concentrated under vacuum. The crude was purified by preparative HPLC (acidic method) to obtain 22 mg (14%) of cis-rac-tert-butyl (3R,5S)-3-amino-5-{2-[1-(cyclopropylmethyl)-1H-pyrrolo[2,3-b]pyridin-2-yl]-1-methyl-1H-1,3-benzodiazole-5-amido}piperidine-1-carboxylate EV-AE3991-001 as a white solid. LCMS (method D): retention time 1.00 min, M/z=544 (M+1).

Cis-rac-tert-butyl (3R,5S)-3-{2-[1-(cyclopropylmethyl)-1H-pyrrolo[2,3-b]pyridin-2-yl]-1-methyl-1H-1,3-benzodiazole-5-amido}-5-[(2E)-4-(dimethylamino)but-2-enamido]piperidine-1-carboxylate EV-AE3993-001—Step 2

Scheme 1.5 Step 2

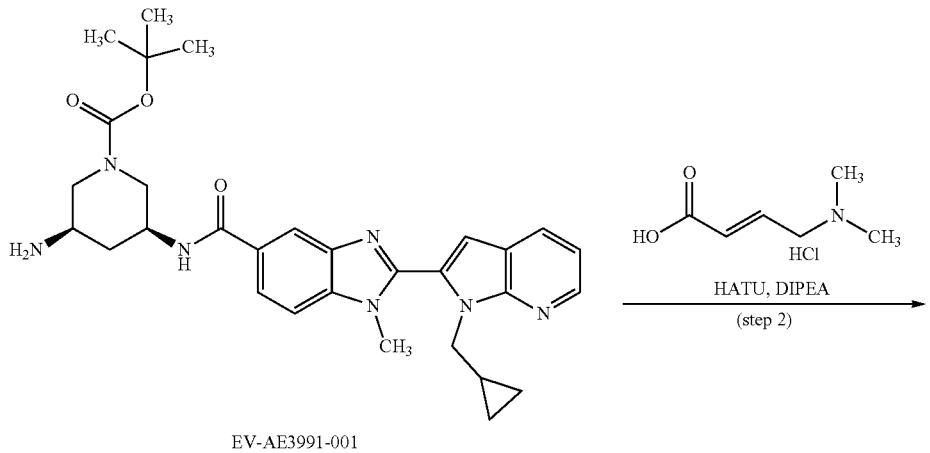

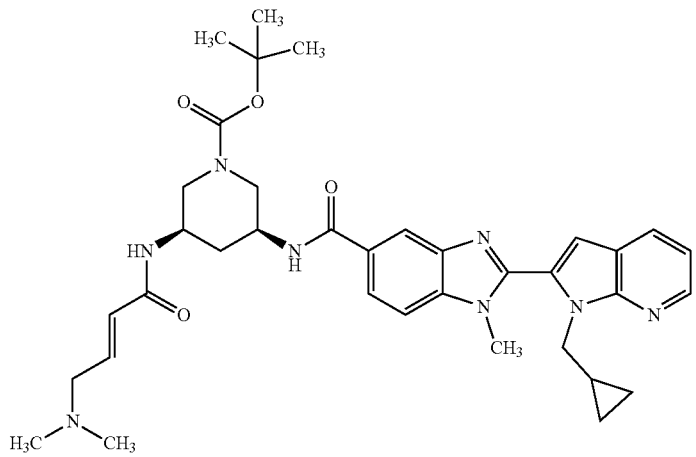

EV-AE3993-001

A solution of cis-rac-tert-butyl (3R,5S)-3-amino-5-{2-[1-(cyclopropylmethyl)-1H-pyrrolo[2,3-b]pyridin-2-yl]-1-methyl-1H-1,3-benzodiazole-5-amido}piperidine-1-carboxylate (EV-AE3991-001, 22 mg, 0.04 mmol), (2E)-4-(dimethylamino)but-2-enoic acid hydrochloride (8 mg, 0.049 mmol) and HATU (18 mg, 0.049 mmol) in dry DMF (0.5 ml) was treated with DIPEA (16 μl, 0.089 mmol) at room temperature. The mixture was stirred for 20 minutes at room temperature. The reaction mixture was diluted with EtOAc (5 ml) and washed with water (2 ml). The aqueous layer was re-extracted with EtOAc (5 ml). The EtOAc layers were combined, washed with saturated aqueous sodium chloride (5 ml), dried over sodium sulfate, filtered and concentrated in vacuo. The crude product was purified by preparative HPLC (acidic method) to obtain 6 mg (22%) of cis-rac-tert-butyl (3R,5S)-3-{2-[1-(cyclopropylmethyl)-1H-pyrrolo[2,3-b]pyridin-2-yl]-1-methyl-1H-1,3-benzodiazole-5-amido}-5-[(2E)-4-(dimethylamino)but-2-enamido]piperidine-1-carboxylate EV-AE3993-001 as a colourless crystalline solid. LCMS (method D): retention time 1.03 min, M/z=655 (M+1).

Cis-rac-2-[1-(cyclopropylmethyl)-1H-pyrrolo[2,3-b]pyridin-2-yl]-N-[(3R,5S)-5-[(2E)-4-(dimethylamino)but-2-enamido]piperidin-3-yl]-1-methyl-1H-1,3-benzodiazole-5-carboxamide Dihydrochloride, I-8 (EV-AE3994-001)—Step 3

Scheme 1.5 Step 3

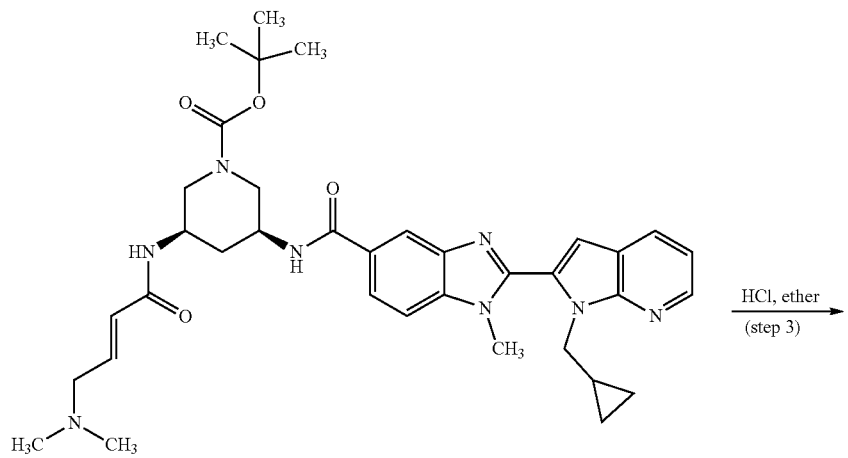

EV-AE3993-001

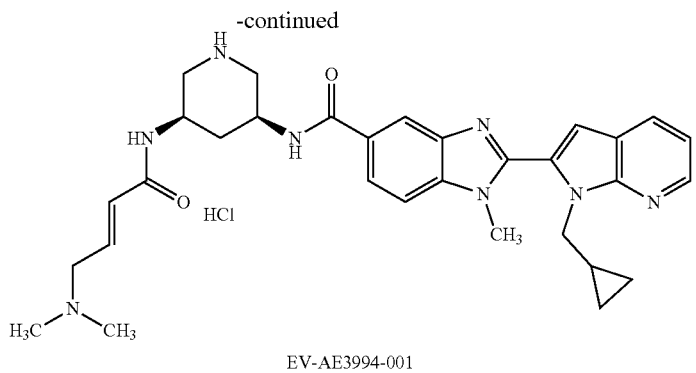

EV-AE3994-001

To cis-rac-tert-butyl (3R,5S)-3-{2-[1-(cyclopropylmethyl)-1H-pyrrolo[2,3-b]pyridin-2-yl]-1-methyl-1H-1,3-benzodiazole-5-amido}-5-[(2E)-4-(dimethylamino)but-2-enamido]piperidine-1-carboxylate (EV-AE3993-001, 6 mg, 0.009 mmol) was added 2M HCl in ether (0.05 ml, 0.092 mmol). The suspension mixture was allowed to stand at room temperature for 1 h. Another portion of 2M HCl in ether (0.05 ml) was added, the reaction mixture was stirred briefly then allowed to stand for 30 mins. The reaction mixture was concentrated to dryness to obtain 5 mg (92%) of rac-2-[1-(cyclopropylmethyl)-1H-pyrrolo[2,3-b]pyridin-2-yl]-N-[(3R,5S)-5-[(2E)-4-(dimethylamino)but-2-enamido]piperidin-3-yl]-1-methyl-1H-1,3-benzodiazole-5-carboxamide dihydrochloride I-8 (EV-AE3994-001) as a white powder. LCMS (method C): retention time 2.90 min, M/z=555 (M+1).

Example 10. Synthesis of Cis-rac-(2E)-N-[(3R,5S)-5-amino-1-{2-[1-(cyclopropylmethyl)-1H-pyrrolo[2,3-b]pyridin-2-yl]-1-methyl-1H-1,3-benzodiazole-5-carbonyl}piperidin-3-yl]-4-(dimethylamino)but-2-enamide, I-10

Cis-rac-(2E)-N-[(3R,5S)-5-amino-1-{2-[1-(cyclopropylmethyl)-1H-pyrrolo[2,3-b]pyridin-2-yl]-1-methyl-1H-1,3-benzodiazole-5-carbonyl}piperidin-3-yl]-4-(dimethylamino)but-2-enamide EV-AU3215-001 (EOAI3442261, 1-10) was synthesised according to the procedures described in Scheme 1.6, steps 1 to 5, from 2-[1-(cyclopropylmethyl)-1H-pyrrolo[2,3-b]pyridin-2-yl]-1-methyl-1H-1,3-benzodiazole-5-carboxylic acid (synthesised as described in Scheme 1).

6,7-dibenzyl 3-{2-[1-(cyclopropylmethyl)-1H-pyrrolo[2,3-b]pyridin-2-yl]-1-methyl-1H-1,3-benzodiazole-5-carbonyl}-3,6,7-triazabicyclo[3.2.1]octane-6,7-dicarboxylate EV-AT0494-001—Step 1

Scheme 1.6 Step 1

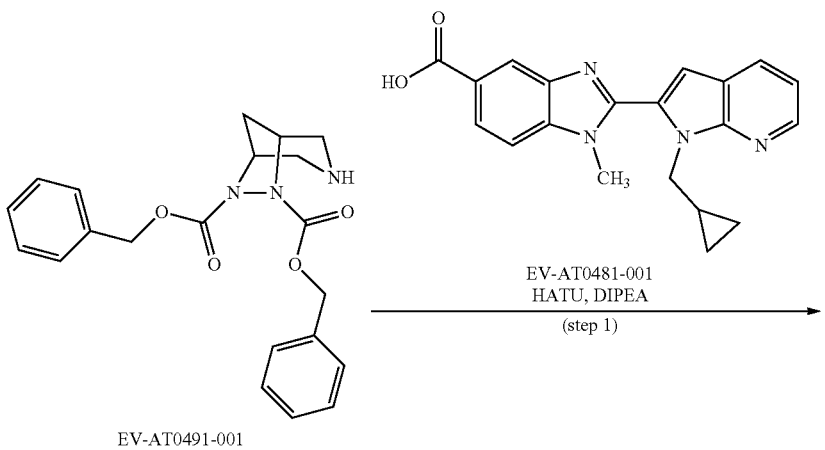

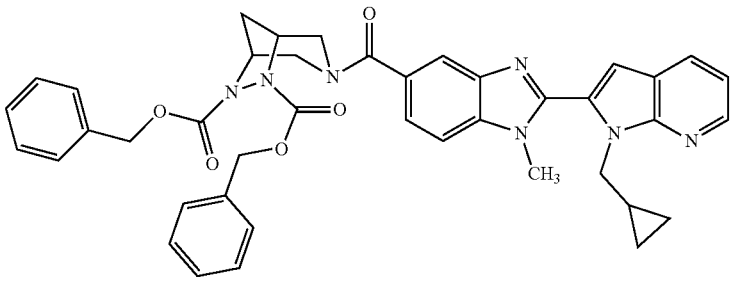

EV-AT0494-001

To a solution of 2-[1-(cyclopropylmethyl)-1H-pyrrolo[2,3-b]pyridin-2-yl]-1-methyl-1H-1,3-benzodiazole-5-carboxylic acid (EV-AT0481-001, 410 mg, 1.18 mmol) in DMF (8 ml) was added DIPEA (235 µl, 1.42 mmol) and HATU (540 mg, 1.42 mmol) and the reaction was stirred under nitrogen at room temperature for 1 h. 6,7-Dibenzyl 3,6,7-triazabicyclo[3.2.1]octane-6,7-dicarboxylate (EV-AT0491-001 prepared as described in *J. Org. Chem.*, 2013, 78(23), p 12236-12242, 497 mg, 1.3 mmol) in DMF (2 ml) was added and the reaction was stirred for a further 2 h. The mixture was quenched with saturated aqueous ammonium chloride (5 ml) and extracted with ethyl acetate (5 ml×3). The combined organic extracts were washed with water (5 ml), saturated aqueous sodium chloride (5 ml), dried over sodium sulfate, filtered and concentrated under vacuum. The crude product was purified via column chromatography (80:100 EtOAc/heptanes, then 0:5% MeOH/EtOAc) to obtain 0.82 g (96%) of 6,7-dibenzyl 3-{2-[1-(cyclopropylmethyl)-1H-pyrrolo[2,3-b]pyridin-2-yl]-1-methyl-1H-1,3-benzodiazole-5-carbonyl}-3,6,7-triazabicyclo[3.2.1]octane-6,7-dicarboxylate EV-AT0494-001 as an orange solid. LCMS (method D): retention time 1.28 min, M/z=710 (M+1).

Cis-rac-(3R,5S)-1-{2-[1-(cyclopropylmethyl)-1H-pyrrolo[2,3-b]pyridin-2-yl]-1-methyl-1H-1,3-benzodiazole-5-carbonyl}piperidine-3,5-diamine EV-AT0497-001—Step 2

Scheme 1.6 Step 2

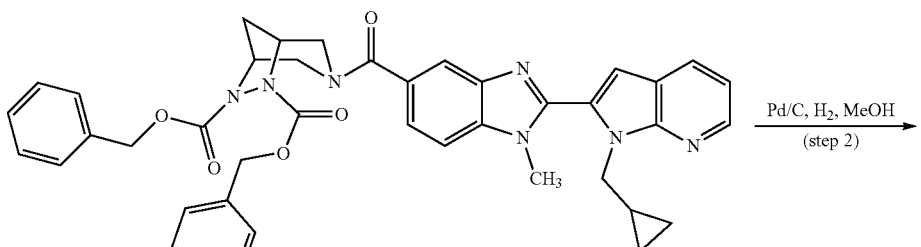

EV-AT0494-001

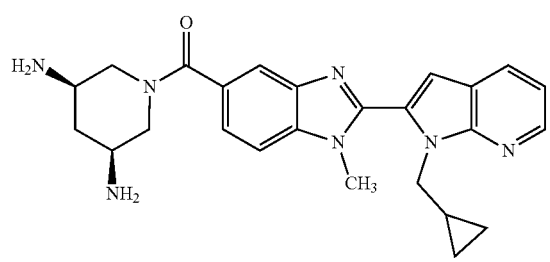

EV-AT0497-001

A 0.05M solution of 6,7-dibenzyl 3-{2-[1-(cyclopropylmethyl)-1H-pyrrolo[2,3-b]pyridin-2-yl]-1-methyl-1H-1,3-benzodiazole-5-carbonyl}-3,6,7-triazabicyclo[3.2.1]octane-6,7-dicarboxylate (EV-AT0494-001, 22 ml) in EtOH was subjected to H-Cube conditions (1 ml/min, 1 bar, 80° C., full hydrogen mode) over a Pd/C (10%) catalyst cartridge. The solvent was removed under vacuum to obtain 0.41 g (82%) of cis-rac-(3R,5S)-1-{2-[1-(cyclopropylmethyl)-1H-pyrrolo[2,3-b]pyridin-2-yl]-1-methyl-1H-1,3-benzodiazole-5-carbonyl}piperidine-3,5-diamine EV-AT0497-001 as an orange oil. LCMS (method D); retention time 0.76 min, M/z=444 (M+1).

Formic Acid; cis-tert-butyl N-(5-amino-1-{2-[1-(cyclopropylmethyl)-1H-pyrrolo[2,3-b]pyridin-2-yl]-1-methyl-1H-1,3-benzodiazole-5-carbonyl}piperidin-3-yl)carbamate EV-AT0498-001—Step 3

Scheme 1.6 Step 3

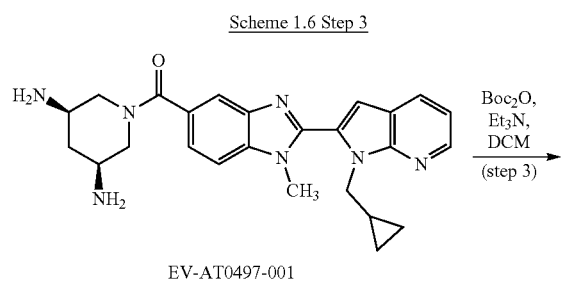

EV-AT0497-001

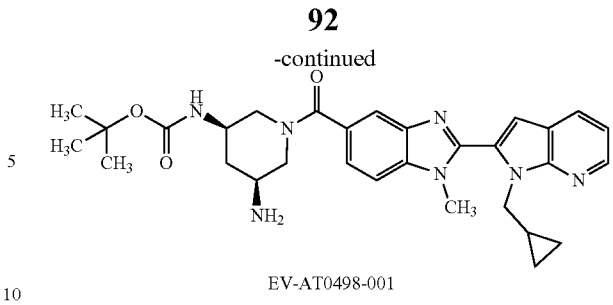

EV-AT0498-001

To a solution of cis-rac-(3R,5S)-1-{2-[1-(cyclopropylmethyl)-1H-pyrrolo[2,3-b]pyridin-2-yl]-1-methyl-1H-1,3-benzodiazole-5-carbonyl}piperidine-3,5-diamine (EV-AT0497-001, 415 mg, 0.94 mmol) in DCM (7.5 ml) was added triethylamine (144 µl, 1.03 mmol) and di-tert-butyl dicarbonate (184 mg, 0.84 mmol) and the reaction was stirred at room temperature for 1 h. The reaction was quenched with saturated aqueous sodium bicarbonate (10 ml) and extracted with DCM (10 ml). The aqueous layer was washed with DCM (10 ml), the combined organic extracts were dried over sodium sulfate, filtered and concentrated under vacuum. The crude was purified by reverse phase column chromatography (10-90% MeCN in water, with both solvents containing 0.1% formic acid) to obtain 0.17 g (30%) of formic acid; cis-tert-butyl N-(5-amino-1-{2-[1-(cyclopropylmethyl)-1H-pyrrolo[2,3-b]pyridin-2-yl]-1-methyl-1H-1,3-benzodiazole-5-carbonyl}piperidin-3-yl)carbamate EV-AT0498-001 as an off-white solid. LCMS (method A): retention time 2.17 min, M/z=544 (M+1).

Cis-tert-butyl N-(1-{2-[1-(cyclopropylmethyl)-1H-pyrrolo[2,3-b]pyridin-2-yl]-1-methyl-1H-1,3-benzodiazole-5-carbonyl}-5-[(2E)-4-(dimethylamino)but-2-enamido]piperidin-3-yl)carbamate EV-AU3206-001—Step 4

Scheme 1.6 Step 4

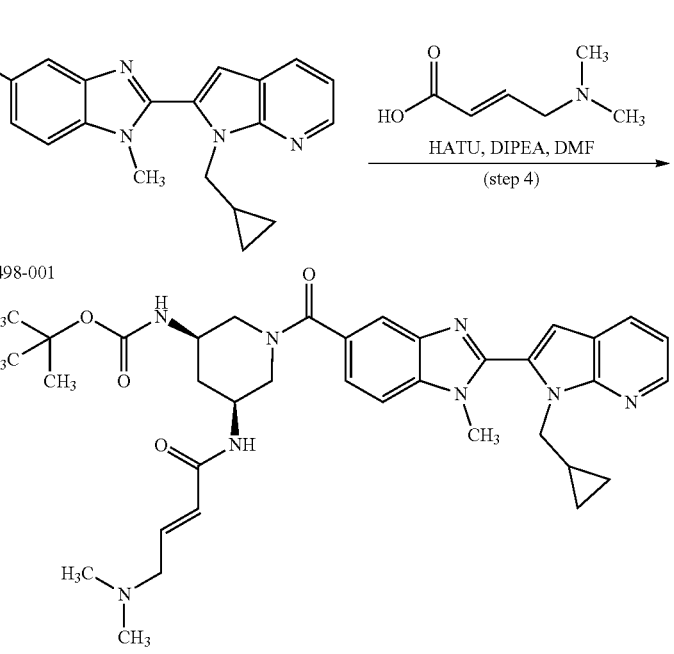

EV-AU3206-001

To a solution of (2E)-4-(dimethylamino)but-2-enoic acid hydrochloride (20 mg, 0.12 mmol) in DMF (0.5 ml) was added HATU (55 mg, 0.14 mmol) and DIPEA (60 µl, 0.36 mmol) and the solution was stirred at room temperature for 1 h. Formic acid; cis-tert-butyl N-(5-amino-1-{2-[1-(cyclopropylmethyl)-1H-pyrrolo[2,3-b]pyridin-2-yl]-1-methyl-1H-1,3-benzodiazole-5-carbonyl}piperidin-3-yl)carbamate (EV-AT0498-001, 52.52 mg, 0.1 mmol) in DMF (0.5 ml) was added and the reaction was stirred for a further 3 h. The solvent was removed under vacuum and the crude was purified by preparative HPLC (acidic method) to obtain 14 mg (18%) of formic acid; cis-tert-butyl N-(5-amino-1-{2-[1-(cyclopropylmethyl)-1H-pyrrolo[2,3-b]pyridin-2-yl]-1-methyl-1H-1,3-benzodiazole-5-carbonyl}piperidin-3-yl)carbamate EV-AU3206-001 as a white solid. LCMS (method A): retention time 2.24 min, M/z=655 (M+1).

Cis-rac-(2E)-N-[(3R,5S)-5-amino-1-{2-[1-(cyclopropylmethyl)-1H-pyrrolo[2,3-b]pyridin-2-yl]-1-methyl-1H-1,3-benzodiazole-5-carbonyl}piperidin-3-yl]-4-(dimethylamino)but-2-enamide, I-10 (EV-AU3215-001)—Step 5

HCl in diethyl ether (1.08 ml) and stirred at room temperature for 2 h. The reaction mixture was concentrated under vacuum to obtain 19 mg (91%) of cis-rac-(2E)-N-[(3R,5S)-5-amino-1-{2-[1-(cyclopropylmethyl)-1H-pyrrolo[2,3-b]pyridin-2-yl]-1-methyl-1H-1,3-benzodiazole-5-carbonyl}piperidin-3-yl]-4-(dimethylamino)but-2-enamide I-10, (EV-AU3215-001) as an off white solid. LCMS (method A): retention time 1.33 min, M/z=555 (M+1).

Example 11. Synthesis of (2E)-N-[2-(1-{2-[1-(Cyclopropylmethyl)-1H-pyrrolo[2,3-b]pyridin-2-yl]-1-methyl-1H-1,3-benzodiazol-5-yl}-N-[2-(1H-imidazol-5-yl)ethyl]formamido)ethyl]-4-(dimethylamino)but-2-enamide, I-7

(2E)-N-[2-(1-{2-[1-(Cyclopropylmethyl)-1H-pyrrolo[2,3-b]pyridin-2-yl]-1-methyl-1H-1,3-benzodiazol-5-yl}-N-[2-(1H-imidazol-5-yl)ethyl]formamido)ethyl]-4-(dimethylamino)but-2-enamide EV-AE3995-001 (EOAI3447034, I-7) was synthesised according to the procedures described in

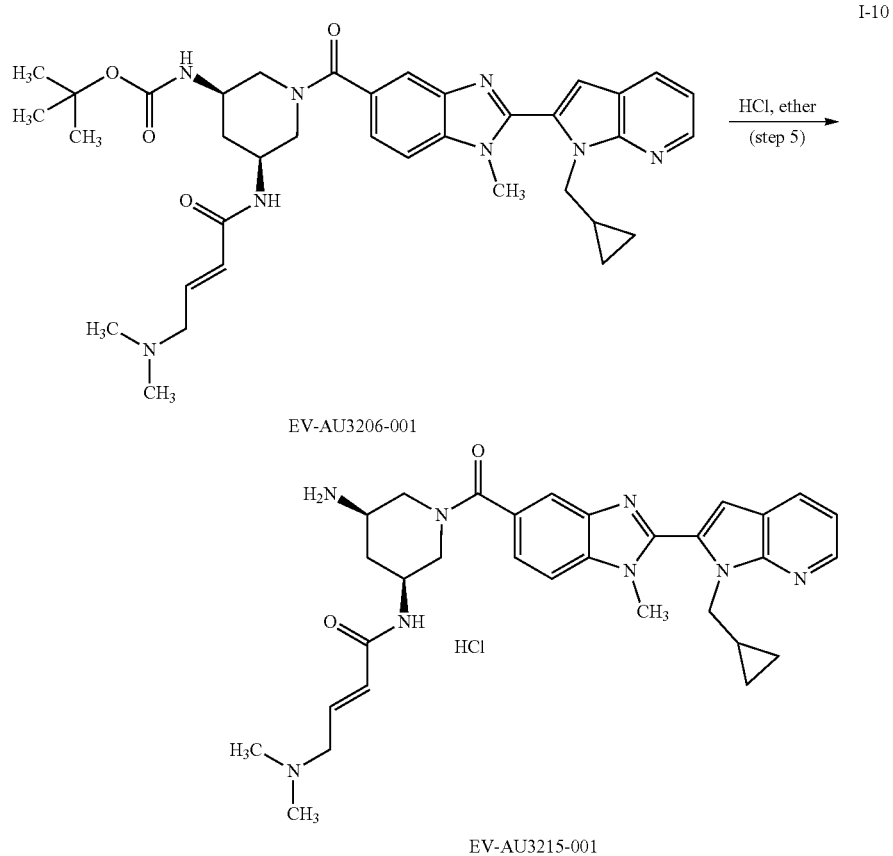

Formic acid; cis-tert-butyl N-(5-amino-1-{2-[1-(cyclopropylmethyl)-1H-pyrrolo[2,3-b]pyridin-2-yl]-1-methyl-1H-1,3-benzodiazole-5-carbonyl}piperidin-3-yl)carbamate (EV-AU3206-001, 14 mg, 0.02 mmol) was dissolved in 2M Scheme 1.7, steps 1 to 4, from 2-[1-(cyclopropylmethyl)-1H-pyrrolo[2,3-b]pyridin-2-yl]-1-methyl-1H-1,3-benzodiazole-5-carboxylic acid EV-AR3168-002 synthesised as described in Scheme 1:

Tert-butyl N-(2-{[2-(1H-imidazol-5-yl)ethyl]amino}ethyl)carbamate EV-AU3211-001—Step 1

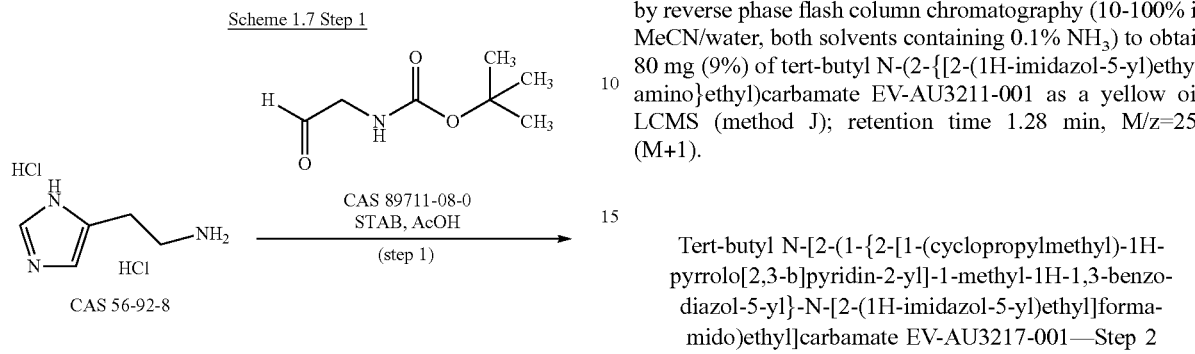

imidazol-5-yl)ethan-1-amine dihydrochloride (CAS 56-92-8, 500 mg, 2.72 mmol) in MeOH (15 ml) was added acetic acid (0.16 ml, 2.72 mmol) followed by portion wise addition of sodium triacetoxyborohydride (2.0 g, 9.42 mmol). The reaction was stirred at room temperature for 16 h. The solvent was removed in vacuo and the residue was purified by reverse phase flash column chromatography (10-100% in MeCN/water, both solvents containing 0.1% $NH_3$) to obtain 80 mg (9%) of tert-butyl N-(2-{[2-(1H-imidazol-5-yl)ethyl]amino}ethyl)carbamate EV-AU3211-001 as a yellow oil. LCMS (method J); retention time 1.28 min, M/z=255 (M+1).

Tert-butyl N-[2-(1-{2-[1-(cyclopropylmethyl)-1H-pyrrolo[2,3-b]pyridin-2-yl]-1-methyl-1H-1,3-benzodiazol-5-yl}-N-[2-(1H-imidazol-5-yl)ethyl]formamido)ethyl]carbamate EV-AU3217-001—Step 2

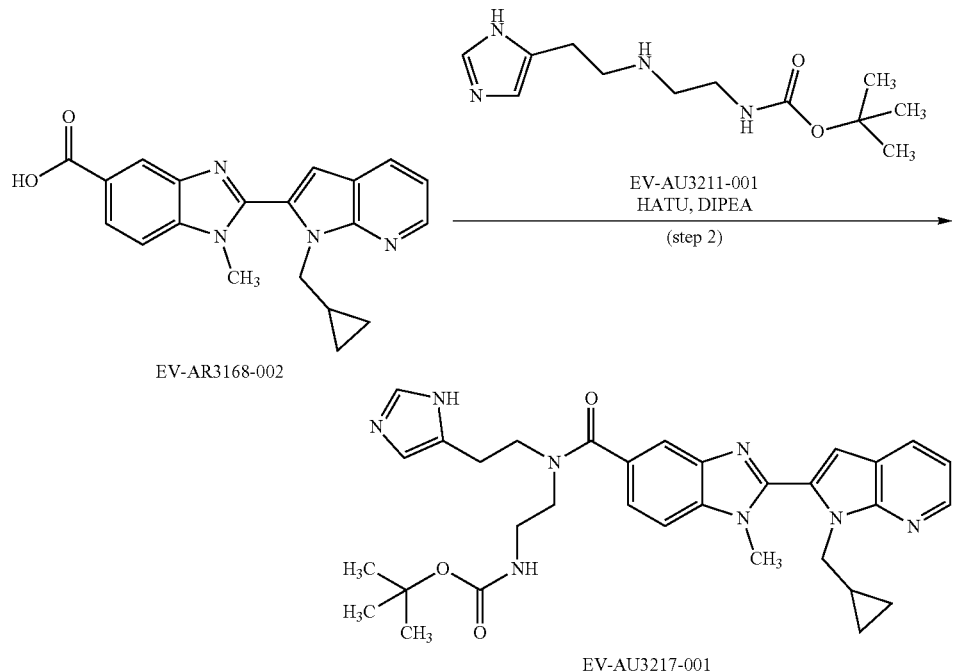

-continued

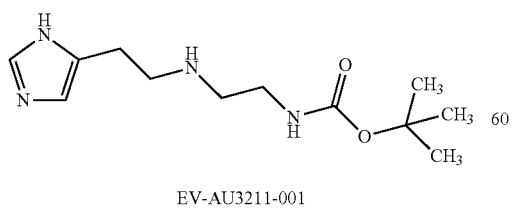

EV-AU3211-001

To a stirred solution of tert-butyl N-(2-oxoethyl)carbamate (CAS 89711-08-0, 649 mg, 4.07 mmol) and 2-(1H-

To a stirred solution of 2-[1-(cyclopropylmethyl)-1H-pyrrolo[2,3-b]pyridin-2-yl]-1-methyl-1H-1,3-benzodiazole-5-carboxylic acid (EV-AR3168-002, 109 mg, 0.31 mmol) in DMF (2 ml) was added HATU (132 mg, 0.35 mmol) and DIPEA (110 µl, 0.63 mmol) and the reaction was stirred at room temperature for 2 h. The reaction mixture was submitted directly for preparative HPLC (basic method) to obtain 25 mg (14%) of tert-butyl N-[2-(1-{2-[1-(cyclopropylmethyl)-1H-pyrrolo[2,3-b]pyridin-2-yl]-1-methyl-1H-1,3-benzodiazol-5-yl}-N-[2-(1H-imidazol-5-yl)ethyl]formamido)ethyl]carbamate EV-AU3217-001 as a colourless powder. LCMS (method D): retention time 0.99 min, M/Z=583 (M+1).

N-(2-Aminoethyl)-2-[1-(cyclopropylmethyl)-1H-pyrrolo[2,3-b]pyridin-2-yl]-N-[2-(1H-imidazol-5-yl)ethyl]-1-methyl-1H-1,3-benzodiazole-5-carboxamide Dihydrochloride EV-AE3992-001—Step 3

Scheme 1.7 Step 3

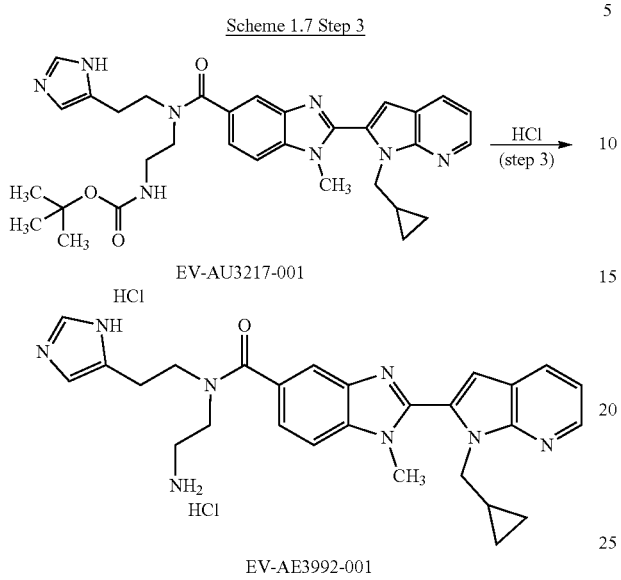

2M HCl in ether (0.22 ml, 0.43 mmol) was added to tert-butyl N-[2-(1-{2-[1-(cyclopropylmethyl)-1H-pyrrolo[2,3-b]pyridin-2-yl]-1-methyl-1H-1,3-benzodiazol-5-yl}-N-[2-(1H-imidazol-5-yl)ethyl]formamido)ethyl]carbamate (EV-AU3217-001, 25 mg, 0.043 mmol) and the resulting mixture was stirred at room temperature for 2 h. The solvent was removed in vacuo and the residue azeotroped with DCM (2 ml). The resulting solid was dried to afford 27 mg (quantitative) of N-(2-aminoethyl)-2-[1-(cyclopropylmethyl)-1H-pyrrolo[2,3-b]pyridin-2-yl]-N-[2-(1H-imidazol-5-yl)ethyl]-1-methyl-1H-1,3-benzodiazole-5-carboxamide dihydrochloride EV-AE3992-001 as a white powder. LCMS (method D): retention time 0.78 min, M/z=483 (M+1).

(2E)-N-[2-(1-{2-[1-(Cyclopropylmethyl)-1H-pyrrolo[2,3-b]pyridin-2-yl]-1-methyl-1H-1,3-benzodiazol-5-yl}-N-[2-(1H-imidazol-5-yl)ethyl]formamido)ethyl]-4-(dimethylamino)but-2-enamide, I-7 (EV-AE3995-001)—Step 4

Scheme 1.7 Step 4

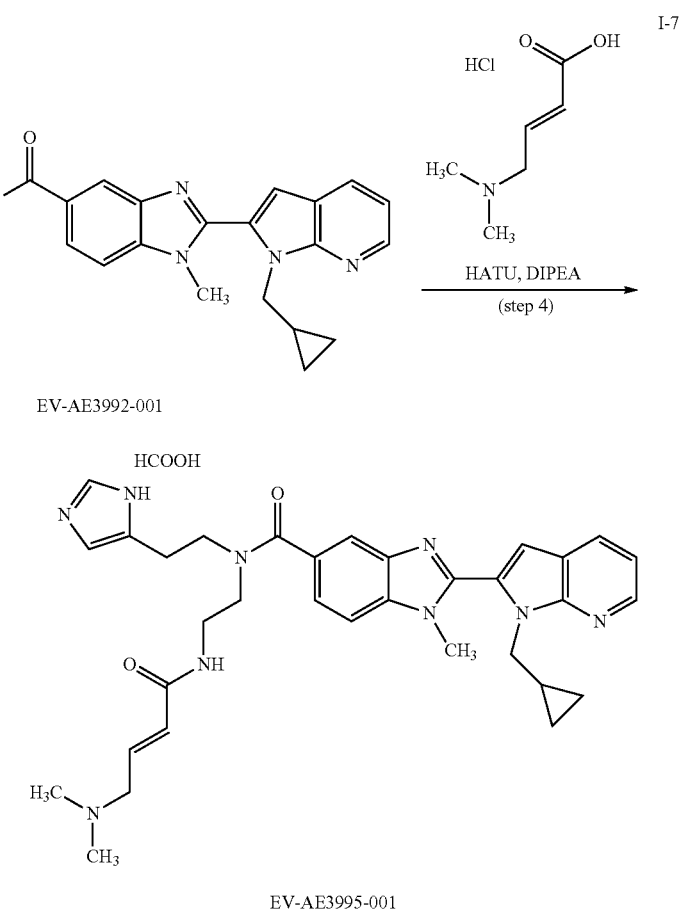

To a stirred solution of N-(2-aminoethyl)-2-[1-(cyclopropylmethyl)-1H-pyrrolo[2,3-b]pyridin-2-yl]-N-[2-(1H-imidazol-5-yl)ethyl]-1-methyl-1H-1,3-benzodiazole-5-carboxamide dihydrochloride (EV-AE3992-001, 27 mg, 0.049 mmol), HATU (22 mg, 0.058 mmol) and (2E)-4-(dimethylamino)but-2-enoic acid hydrochloride (10 mg, 0.058 mmol) in dry DMF (1 ml) was added DIPEA (30 µl, 0.17 mmol). The reaction was stirred at room temperature for 20 minutes. The solvent was removed in vacuo and the residue was submitted for preparative HPLC (acidic method) to afford 2.6 mg (8%) of (2E)-N-[2-(1-{2-[1-(cyclopropylmethyl)-1H-pyrrolo[2,3-b]pyridin-2-yl]-1-methyl-1H-1,3-benzodiazol-5-yl}-N-[2-(1H-imidazol-5-yl)ethyl]formamido)ethyl]-4-(dimethylamino)but-2-enamide formate EV-AE3995-001 as a colourless solid. LCMS (method C): retention time 2.72 min, M/z=594 (M+1).

Example 12. Synthesis of (2E)-N-[(3R)-1-{2-[1-(cyclopropylmethyl)-1H-pyrrolo[2,3-b]pyridin-2-yl]-1-methyl-1H-1,3-benzodiazole-5-carbonyl}piperidin-3-yl]-4-(dimethylamino)but-2-enamide, I-12

(2E)-N-[(3R)-1-{2-[1-(cyclopropylmethyl)-1H-pyrrolo[2,3-b]pyridin-2-yl]-1-methyl-1H-1,3-benzodiazole-5-carbonyl}piperidin-3-yl]-4-(dimethylamino)but-2-enamide EV-AQ1925-001 (EOAI3426752, I-12) was synthesised according to the procedures described in Scheme 1.8, steps 1 to 3, from 2-[1-(cyclopropylmethyl)-1H-pyrrolo[2,3-b]pyridin-2-yl]-1-methyl-1H-1,3-benzodiazole-5-carboxylic acid EV-AR3168-002 synthesised as described in Scheme 1:

Tert-butyl N-[(3R)-1-{2-[1-(cyclopropylmethyl)-1H-pyrrolo[2,3-b]pyridin-2-yl]-1-methyl-1H-1,3-benzodiazole-5-carbonyl}piperidin-3-yl]carbamate EV-AP0493-002—Step 1

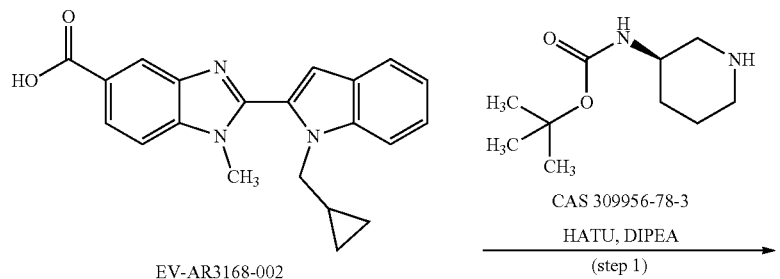

Scheme 1.8 Step 1

EV-AR3168-002

CAS 309956-78-3

HATU, DIPEA
(step 1)

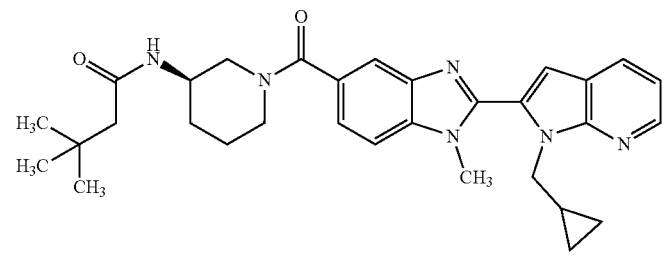

EV-AP0493-002

To a stirred solution of 2-[1-(cyclopropylmethyl)-1H-pyrrolo[2,3-b]pyridin-2-yl]-1-methyl-1H-1,3-benzodiazole-5-carboxylic acid (EV-AR3168-002, 300 mg, 0.87 mmol) and HATU (362 mg, 0.95 mmol) in dry DMF (9 ml) was added DIPEA (166 μl, 0.95 mmol). The reaction was stirred for 1 h at room temperature and tert-butyl N-[(3R)-piperidin-3-yl]carbamate (CAS 309956-78-3, 208 mg, 1.04 mmol) was added. The reaction was stirred at room temperature for 16 h and concentrated in vacuo. The residue was partitioned between DCM (30 ml) and saturated aqueous sodium bicarbonate (30 ml). The aqueous layer was extracted with DCM (20 ml) and the combined organics were washed with water (20 ml) and saturated aqueous sodium chloride (20 ml), dried over magnesium sulfate, filtered and concentrated in vacuo. The crude material was purified by flash column chromatography (1-10% MeOH/DCM) to obtain 352 mg (76%) of tert-butyl N-[(3R)-1-{2-[1-(cyclopropylmethyl)-1H-pyrrolo[2,3-b]pyridin-2-yl]-1-methyl-1H-1,3-benzodiazole-5-carbonyl}piperidin-3-yl]carbamate EV-AP0493-002 as a yellow crystalline solid. LCMS (method D): retention time 1.34 min, M/z=529 (M+1).

(3R)-1-{2-[1-(cyclopropylmethyl)-1H-pyrrolo[2,3-b]pyridin-2-yl]-1-methyl-1H-1,3-benzodiazole-5-carbonyl}piperidin-3-amine Hydrochloride EV-AP4097-001—Step 2

Scheme 1.8 Step 2

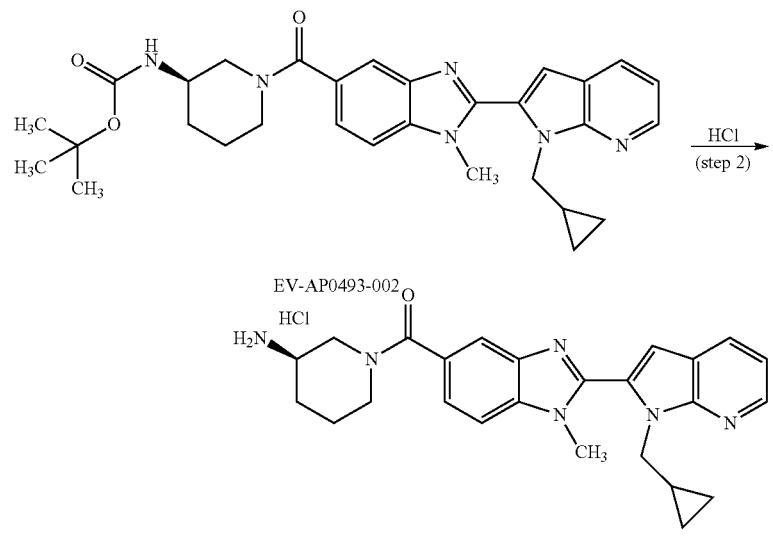

EV-AP4097-001

To a stirred solution of tert-butyl N-[(3R)-1-{2-[1-(cyclopropylmethyl)-1H-pyrrolo[2,3-b]pyridin-2-yl]-1-methyl-1H-1,3-benzodiazole-5-carbonyl}piperidin-3-yl]carbamate (EV-AP0493-002, 352 mg, 0.66 mmol) in methanol (3 ml) was added 4M HCl in dioxane (7 ml). The reaction was stirred at room temperature for 3 h. The reaction mixture was concentrated in vacuo and the resulting solid was dried to obtain 299 mg (96%) of (3R)-1-{2-[1-(cyclopropylmethyl)-1H-pyrrolo[2,3-b]pyridin-2-yl]-1-methyl-1H-1,3-benzodiazole-5-carbonyl}piperidin-3-amine hydrochloride EV-AP4097-001 as a yellow powder. LCMS (method D): retention time 1.00 min, M/z=429 (M+1).

(2E)-N-[(3R)-1-{2-[1-(cyclopropylmethyl)-1H-pyrrolo[2,3-b]pyridin-2-yl]-1-methyl-1H-1,3-benzodiazole-5-carbonyl}piperidin-3-yl]-4-(dimethylamino)but-2-enamide, I-12 (EV-AQ1925-001)—Step 3

Scheme 1.8 Step 3

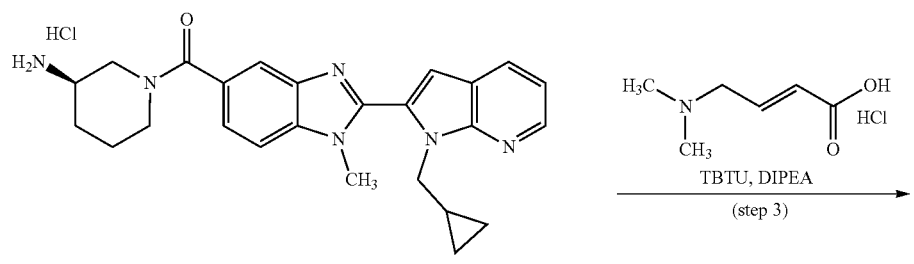

EV-AP0497-001

-continued

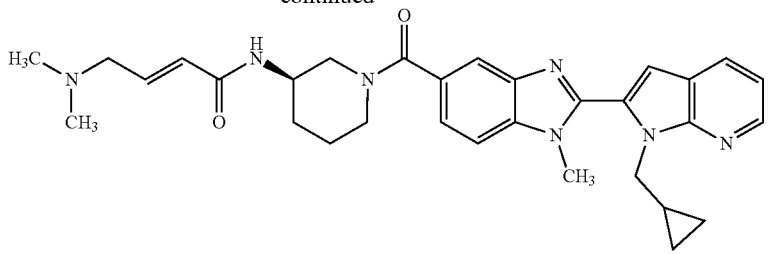

EV-AQ1925-001
I-12

To a stirred solution of (3R)-1-{2-[1-(cyclopropylmethyl)-1H-pyrrolo[2,3-b]pyridin-2-yl]-1-methyl-1H-1,3-benzodiazole-5-carbonyl}piperidin-3-amine hydrochloride (EV-AP4097-001, 50 mg, 0.11 mmol) in DMF (1 ml) was added (2E)-4-(dimethylamino)but-2-enoic acid hydrochloride (21 mg, 0.13 mmol), DIPEA (62 mg, 0.54 mmol) and TBTU (45 mg, 0.14 mmol). The mixture was stirred at room temperature for 2 h. The reaction mixture was filtered and the filtrate was submitted for preparative HPLC (basic method) to afford 25 mg (43%) of (2E)-N-[(3R)-1-{2-[1-(cyclopropylmethyl)-1H-pyrrolo[2,3-b]pyridin-2-yl]-1-methyl-1H-1,3-benzodiazole-5-carbonyl}piperidin-3-yl]-4-(dimethylamino)but-2-enamide I-12 (EV-AQ1925-001) as a white solid. LCMS (method A): retention time 1.88 min, M/z=540 (M+1).

Example 13. Synthesis of N-[(3R)-1-{2-[1-(cyclopropylmethyl)-1H-pyrrolo[2,3-b]pyridin-2-yl]-1-methyl-1H-1,3-benzodiazole-5-carbonyl}piperidin-3-yl]prop-2-enamide, I-13

N-[(3R)-1-{2-[1-(cyclopropylmethyl)-1H-pyrrolo[2,3-b]pyridin-2-yl]-1-methyl-1H-1,3-benzodiazole-5-carbonyl}piperidin-3-yl]prop-2-enamide EV-AO7886-002 (EOAI3426521, I-13) was synthesised according to the procedures described in Scheme 1.9 from 3R)-1-{2-[1-(cyclopropylmethyl)-1H-pyrrolo[2,3-b]pyridin-2-yl]-1-methyl-1H-1,3-benzodiazole-5-carbonyl}piperidin-3-amine hydrochloride EV-AP4097-001 synthesised as described in Scheme 1.8:

Scheme 1.9

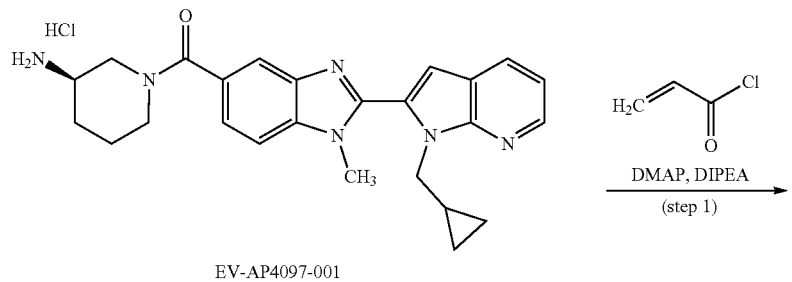

N-[(3R)-1-{2-[1-(cyclopropylmethyl)-1H-pyrrolo[2,3-b]pyridin-2-yl]-1-methyl-1H-1,3-benzodiazole-5-carbonyl}piperidin-3-yl]prop-2-enamide, I-13 (EV-AO7886-002)—Step 1

To a stirred solution of DIPEA (178 μl, 1.02 mmol), DMAP (1.2 mg, 0.01 mmol) and (3R)-1-{2-[1-(cyclopropylmethyl)-1H-pyrrolo[2,3-b]pyridin-2-yl]-1-methyl-1H-1,3-benzodiazole-5-carbonyl}piperidin-3-amine hydrochloride (EV-AP4097-001, 50 mg, 0.11 mmol) in DCM (5 ml) at 0° C. was added a solution of prop-2-enoyl chloride (26 μl, 0.32 mmol) in DCM (3 ml) dropwise. The reaction was stirred at 0° C. for 1 h. Water (1 ml) was added and the layers were separated using a hydrophobic filter. The organic phase was concentrated in vacuo and the crude material purified by preparative HPLC (acidic method) to afford 21 mg (41%) of N-[(3R)-1-{2-[1-(cyclopropylmethyl)-1H-pyrrolo[2,3-b]pyridin-2-yl]-1-methyl-1H-1,3-benzodiazole-5-carbonyl}piperidin-3-yl]prop-2-enamide I-13 (EV-AO7886-002) as a colourless crystalline solid. LCMS (method A): retention time 2.61 min, M/z=483 (M+1).

The following compounds were synthesised according to procedures described above:

| Structure | # | Mol Wt | LCMS $T_{ret}$ | M/z (+) | LCMS Method | Salt | Salt Stoichiometry |
|---|---|---|---|---|---|---|---|
| 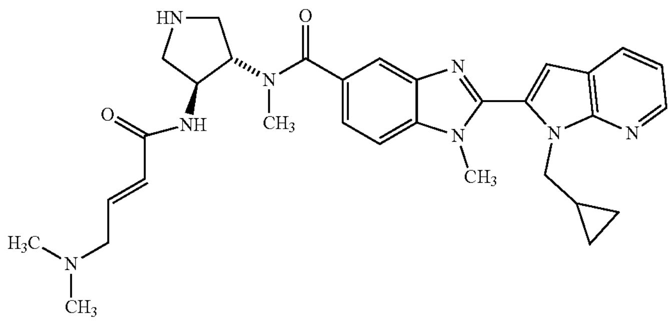 | I-1 | 554.686 | 1.43 min | 555.3 | A | HCl | 2 |
| 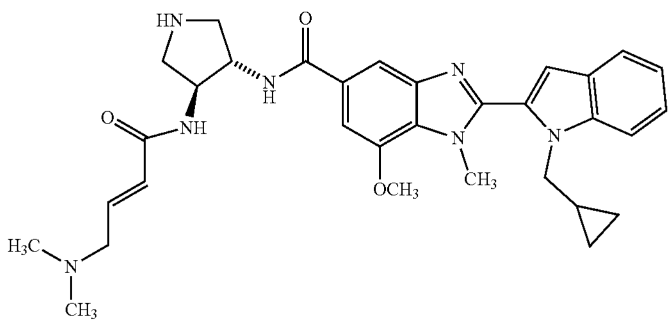 | I-2 | 569.697 | 1.98 min | 571.2 | A | HCl | 2 |
| 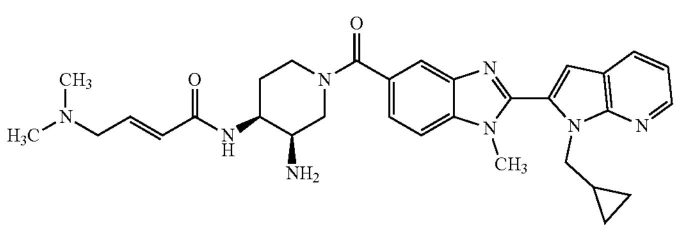 [SMILES: CN(C)C/C=C/C(=O)N[C@H]1CCN(C(=O)c2ccc3c(c2)nc(-c2cc4cccnc4n2CC2CC2)n3C)C[C@H]1N] | I-3 | 554.686 | 1.48 min | 555.3 | A | HCl | 2 |
| 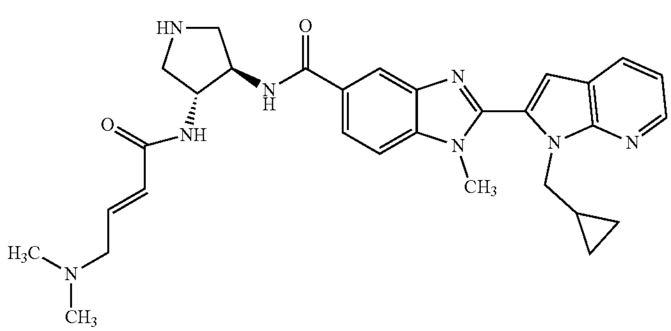 [SMILES: CN(C)C/C=C/C(=O)N[C@@H]1CNC[C@H]1NC(=O)c1ccc2c(c1)nc(-c1cc3cccnc3n1CC1CC1)n2C] | I-4 | 540.659 | 1.44 min | 541.3 | A | HCl | 2 |

-continued

| Structure | # | Mol Wt | LCMS $T_{ret}$ | M/z (+) | LCMS Method | Salt | Salt Stoichiometry |
|---|---|---|---|---|---|---|---|
| 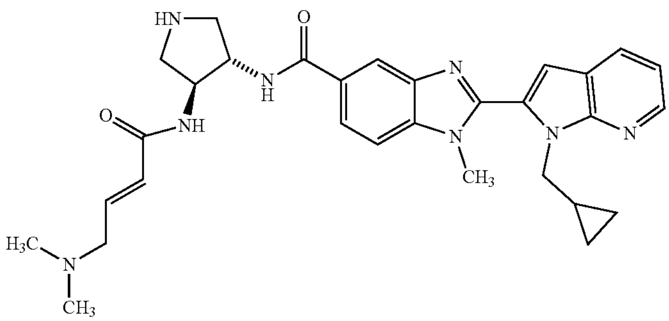 | I-5 | 540.659 | 1.43 min | 541.3 | A | HCl | 2 |
| 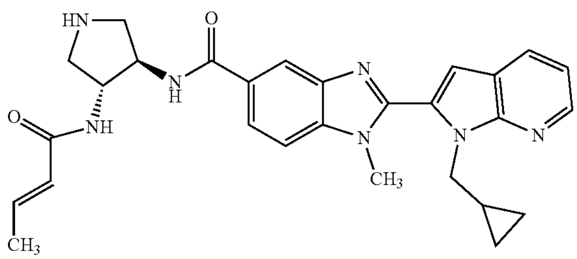 [SMILES: C/C=C/C(=O)N[C@@H]1CNC[C@H]1NC(=O)c1ccc2c(c1)nc(-c1cc3cccnc3n1CC1CC1)n2C] | I-6 | 497.591 | 3.35 min | 498.2 | C | HCl | 1 |
| 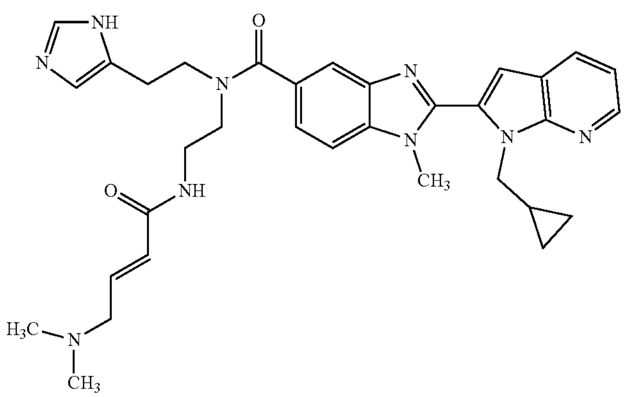 [SMILES: CN(C)C/C=C/C(=O)NCCN(CCc1cnc[nH]1)C(=O)c1ccc2c(c1)nc(-c1cc3cccnc3n1CC1CC1)n2C] | I-7 | 593.722 | 2.72 min | 594.3 | C | HCO2H | 1 |
| 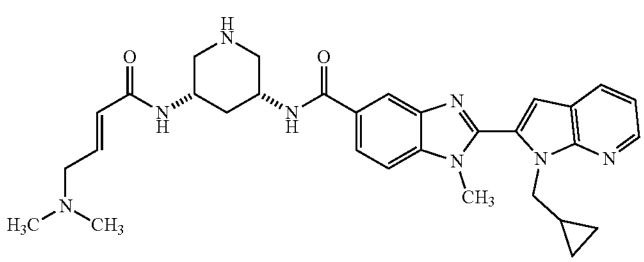 | I-8 | 554.686 | 2.90 min | 555.2 | C | HCl | 2 |
| 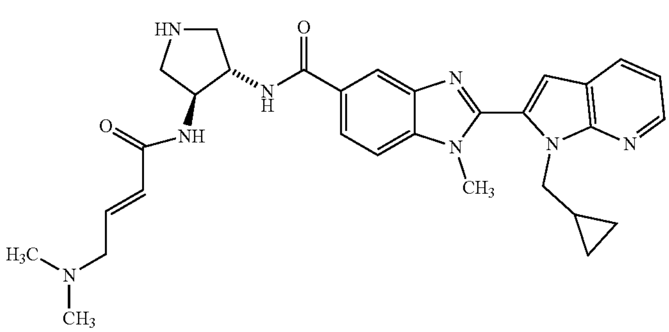 | I-9 | 540.659 | 2.80 min | 541.2 | C | HCl | 2 |

| Structure | # | Mol Wt | LCMS T_ret | M/z (+) | LCMS Method | Salt | Salt Stoichiometry |
|---|---|---|---|---|---|---|---|
| 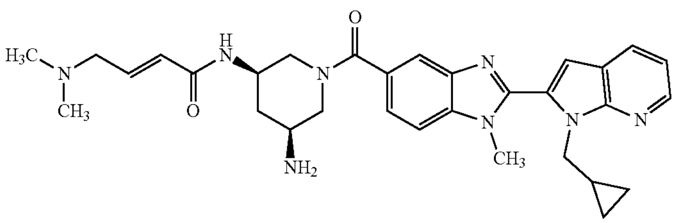 [SMILES: CN(C)C/C=C/C(=O)N[C@@H]1C[C@H](N)CN(C(=O)c2ccc3c(c2)nc(-c2cc4cccnc4n2CC2CC2)n3C)C1] | I-10 | 554.686 | 1.33 min | 555.2 | A | HCl | 2 |
| 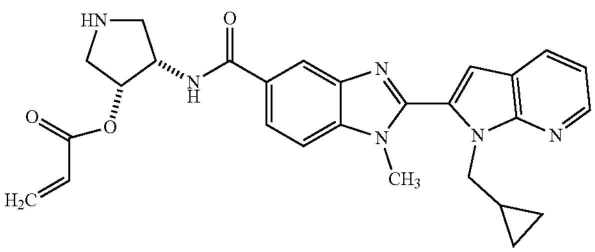 | I-11 | 484.550 | 1.96 min | 485.1 | A | HCl | 1 |
| 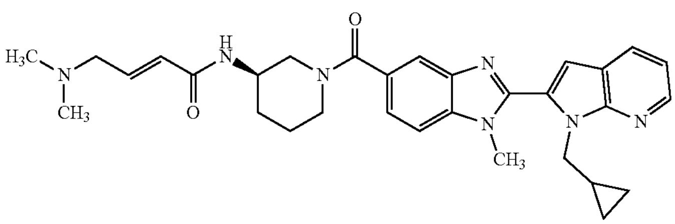 [SMILES: CN(C)C/C=C/C(=O)N[C@@H]1CCCN(C(=O)c2ccc3c(c2)nc(-c2cc4cccnc4n2CC2CC2)n3C)C1] | I-12 | 539.671 | 1.88 min | 540.3 | A | | |
| 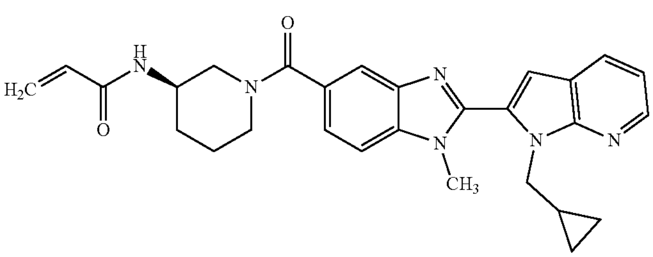 [SMILES: C=CC(=O)N[C@@H]1CCCN(C(=O)c2ccc3c(c2)nc(-c2cc4cccnc4n2CC2CC2)n3C)C1] | I-13 | 482.577 | 2.61 min | 483.3 | A | | |

Example 14. Synthesis of N-[(1S,4R,6R,7R)-7-amino-2-{2-[1-(cyclopropylmethyl)-1H-pyrrolo[2,3-b]pyridin-2-yl]-7-methoxy-1-methyl-1H-1,3-benzodiazole-5-carbonyl}-2-azabicyclo[2.2.1]heptan-6-yl]-N-methylprop-2-enamide, I-16 and N-[(1S,4R,6S,7R)-7-amino-2-{2-[1-(cyclopropylmethyl)-1H-pyrrolo[2,3-b]pyridin-2-yl]-7-methoxy-1-methyl-1H-1,3-benzodiazole-5-carbonyl}-2-azabicyclo[2.2.1]heptan-6-yl]-N-methylprop-2-enamide, I-17

N-[(1S,4R,6R,7R)-7-amino-2-{2-[1-(cyclopropylmethyl)-1H-pyrrolo[2,3-b]pyridin-2-yl]-7-methoxy-1-methyl-1H-1,3-benzodiazole-5-carbonyl}-2-azabicyclo[2.2.1]heptan-6-yl]-N-methylprop-2-enamide 1-16 (EV-AZ4416-001) (EOAI3478697) LCMS (method A): retention time 1.93 min, M/z=554.4 (M+1) and N-[(1S,4R,6S,7R)-7-amino-2-{2-[1-(cyclopropylmethyl)-1H-pyrrolo[2,3-b]pyridin-2-yl]-7-methoxy-1-methyl-1H-1,3-benzodiazole-5-carbonyl}-2-azabicyclo[2.2.1]heptan-6-yl]-N-methylprop-2-enamide 1-17 (EV-AZ4417-001) (EOAI3478698) LCMS (method A); retention time 2.10 min, M/z=554.4 (M+1) were synthesised according to procedures described in Scheme 1.10, steps 1-10, from 2-[1-(cyclopropylmethyl)-1H-pyrrolo[2,3-b]pyridin-2-yl]-7-methoxy-1-methyl-1H-1,3-benzodiazole-5-carboxylic acid EV-AV3032-001 which was synthesised according to the procedures described in Scheme 1.

Scheme 1.10 Step 1

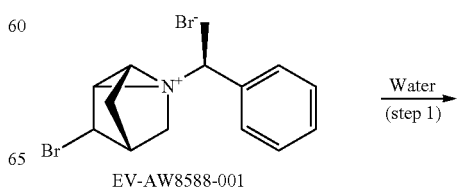

EV-AW8588-001

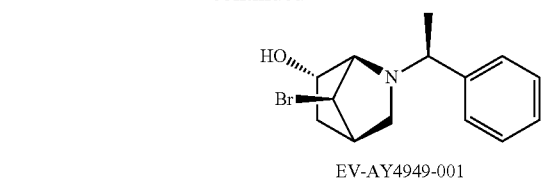

EV-AY4949-001

(1R,4R,6S,7R)-7-Bromo-2-[(1S)-1-phenylethyl]-2-azabicyclo[2.2.1]heptan-6-ol EV-AY4949-001—Step 1

A solution of (4R,6R)-3-bromo-1-[(1S)-1-phenylethyl]-1-azatricyclo[2.2.1.0]heptan-1-ium bromide (EV-AW8588-001, 8.70 g, 19.4 mmol) (synthesised as in *Adv. Synth. Catal.* 2005, 347, 1242-1246) in acetonitrile: water (1:1, 100 ml) was stirred at 65° C. for 20 h. The reaction mixture was concentrated in vacuo and the residue was purified by flash column chromatography (20-80% EtOAc/heptane) to afford 4.29 g (73%) of (1R,4R,6S,7R)-7-bromo-2-[(1S)-1-phenylethyl]-2-azabicyclo[2.2.1]heptan-6-ol EV-AY4949-001 as an off-white solid. $^1$H NMR (250 MHz, Chloroform-d) δ 7.38-7.14 (m, 5H), 4.10 (s, 2H), 3.58 (q, J=6.1 Hz, 1H), 3.36-3.23 (m, 1H), 2.65 (dt, J=9.0, 3.1 Hz, 1H), 2.58-2.46 (m, 1H), 2.28-1.91 (m, 4H), 1.32 (d, J=6.4 Hz, 3H). No LCMS data.

Scheme 1.10 Step 2

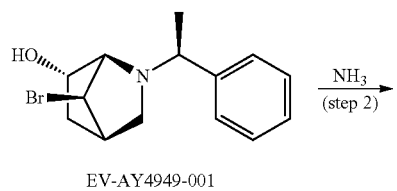

EV-AY4949-001

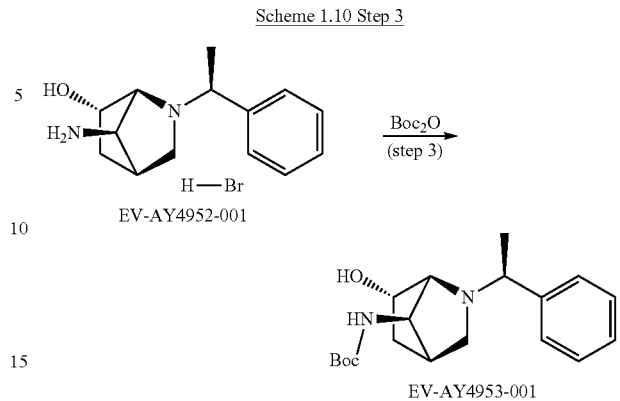

EV-AY4952-001

(1S,4R,6S,7R)-7-amino-2-[(1S)-1-phenylethyl]-2-azabicyclo[2.2.1]heptan-6-ol hydrobromide EV-AY4952-001—Step 2

(1R,4R,6S,7R)-7-bromo-2-[(1S)-1-phenylethyl]-2-azabicyclo[2.2.1]heptan-6-ol (EV-AY4949-001, 4.29 g, 14.2 mmol) was dissolved in 7N ammonia in methanol (15 ml) and the resulting mixture was heated at 65° C. for 2 h. The solvent was removed in vacuo to afford 4.62 g (quantitative) of (1S,4R,6S,7R)-7-amino-2-[(1S)-1-phenylethyl]-2-azabicyclo[2.2.1]heptan-6-ol hydrobromide EV-AY4952-001 as a yellow solid. LCMS (method D): retention time 0.20 min, M/z=233 (M+1).

Scheme 1.10 Step 3

EV-AY4952-001

EV-AY4953-001

Tert-butyl N-[(1S,4R,6S,7R)-6-hydroxy-2-[(1S)-1-phenylethyl]-2-azabicyclo[2.2.1]heptan-7-yl]carbamate EV-AY4953-001—Step 3

Di-tert-butyl dicarbonate (3.41 g, 15.6 mmol) was added to a solution of (1R,4R,6S,7R)-7-amino-2-[(1 S)-1-phenylethyl]-2-azabicyclo[2.2.1]heptan-6-ol hydrobromide (EV-AY4952-001, 4.62 g, 14.2 mmol) and triethylamine (2.97 ml, 21.28 mmol) in DCM (50 ml). The resulting mixture was stirred at room temperature for 2.5 h, washed with saturated aqueous sodium bicarbonate (35 ml), water (2×30 ml) and saturated aqueous sodium chloride (35 ml), dried over sodium sulfate and concentrated in vacuo. The resulting solid was triturated with DCM: diethyl ether (1:4, 20 ml), filtered and dried to obtain 3.24 g (65%) of tert-butyl N-[(1S,4R,6S,7R)-6-hydroxy-2-[(1S)-1-phenylethyl]-2-azabicyclo[2.2.1]heptan-7-yl]carbamate EV-AY4953-001 as an off-white solid. LCMS (method D): retention time 1.02 min, M/z=333 (M+1).

Scheme 1.10 Step 4

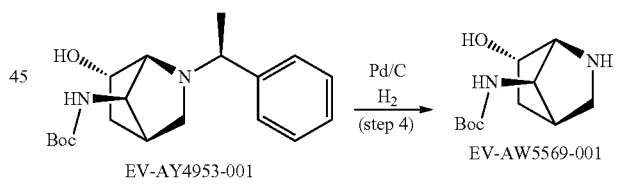

Tert-butyl N-[(1S,4R,6S,7R)-6-hydroxy-2-azabicyclo[2.2.1]heptan-7-yl]carbamate EV-AW5569-001—Step 4

A solution of tert-butyl N-[(1S,4R,6S,7R)-6-hydroxy-2-[(1S)-1-phenylethyl]-2-azabicyclo[2.2.1]heptan-7-yl]carbamate (EV-AY4953-001, 350 mg, 1.05 mmol) in ethanol (10 ml) was purged with nitrogen. Pd/C (5%, 224 mg, 0.11 mmol) was added, the reaction mixture was purged with nitrogen and stirred under a hydrogen atmosphere for 12 h. The reaction mixture was filtered through filter paper (washing with methanol). The filtrate was concentrated in vacuo to afford 170 mg (71%) of tert-butyl N-[(1S,4R,6S,7R)-6-hydroxy-2-azabicyclo[2.2.1]heptan-7-yl]carbamate EV-AW5569-001 as a white solid. $^1$H NMR (500 MHz, Chloroform-d) δ 5.84 (s, 1H), 3.99 (d, J=40.5 Hz, 2H), 3.12

(s, 1H), 2.98 (d, J=9.2 Hz, 1H), 2.53-2.41 (m, 2H), 1.98 (dd, J=13.7, 6.9 Hz, 1H), 1.75 (d, J=13.1 Hz, 1H), 1.44 (s, 9H). No LCMS data.

Tert-butyl N-[(1S,4R,6S,7R)-2-{2-[1-(cyclopropylmethyl)-1H-pyrrolo[2,3-b]pyridin-2-yl]-7-methoxy-1-methyl-1H-1,3-benzodiazole-5-carbonyl}-6-hydroxy-2-azabicyclo[2.2.1]heptan-7-yl]carbamate EV-AY5029-001—Step 5

To a solution of 2-[1-(cyclopropylmethyl)-1H-pyrrolo[2,3-b]pyridin-2-yl]-7-methoxy-1-methyl-1H-1,3-benzodiazole-5-carboxylic acid (EV-AV3032-001, 0.969 g, 2.58 mmol) in DMF (12 ml) was added HATU (1.08 g, 2.83 mmol) and DIPEA (1.12 ml, 6.44 mmol) followed by tert-butyl N-[(1S,4R,6S,7R)-6-hydroxy-2-azabicyclo[2.2.1]heptan-7-yl]carbamate (EV-AW5569-001, 98%, 0.60 g, 2.58 mmol). The resulting mixture was stirred at room temperature for 30 minutes. The reaction was diluted with EtOAc (100 ml) and water (100 ml). The organic phase was collected and the aqueous phase was extracted with EtOAc (100 ml). The combined organics were washed with saturated aqueous sodium chloride (100 ml), dried over magnesium sulfate and concentrated in vacuo. The crude product was purified by flash column chromatography (50-100% EtOAc/heptane then 5% methanol/EtOAc) to afford 736 mg (48%) of tert-butyl N-[(1S,4R,6S,7R)-2-{2-[1-(cyclopropylmethyl)-1H-pyrrolo[2,3-b]pyridin-2-yl]-7-methoxy-1-methyl-1H-1,3-benzodiazole-5-carbonyl}-6-hydroxy-2-azabicyclo[2.2.1]heptan-7-yl]carbamate EV-AY5029-001 as an off-white solid. LCMS (method D) retention time 1.19 min, M/z=587 (M+1).

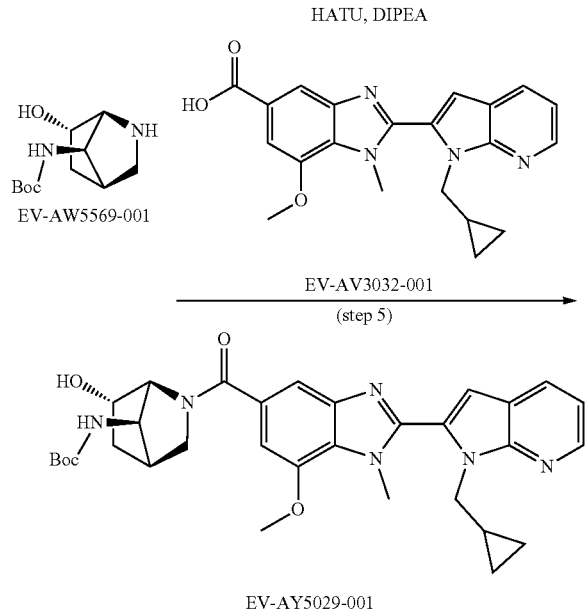

Scheme 1.10 Step 5

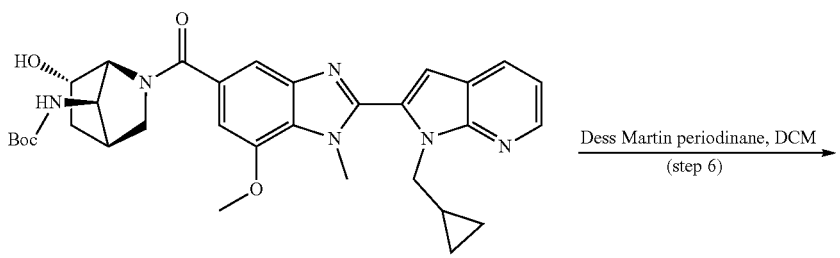

Scheme 1.10 Step 6

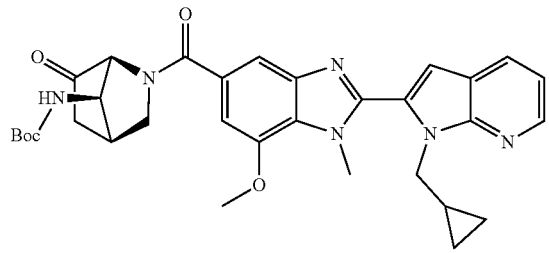

Tert-butyl N-[(1S,4R,7R)-2-{2-[1-(cyclopropylmethyl)-1H-pyrrolo[2,3-b]pyridin-2-yl]-7-methoxy-1-methyl-1H-1,3-benzodiazole-5-carbonyl}-6-oxo-2-azabicyclo[2.2.1]heptan-7-yl]carbamate EV-AZ4415-001—Step 6

To a solution of tert-butyl N-[(1S,4R,6S,7R)-2-{2-[1-(cyclopropylmethyl)-1H-pyrrolo[2,3-b]pyridin-2-yl]-7-methoxy-1-methyl-1H-1,3-benzodiazole-5-carbonyl}-6-hydroxy-2-azabicyclo[2.2.1]heptan-7-yl]carbamate (EV-AY5029-001, 490 mg, 0.84 mmol) in DCM (10 ml) at 0° C. was added Dess-Martin periodinane (710 mg, 1.67 mmol) and the reaction was allowed to warm to room temperature. The reaction mixture was stirred for 24 h, quenched with saturated aqueous sodium thiosulfate (10 ml) and extracted with DCM (3×20 ml). The combined organic layers were dried over sodium sulfate, filtered and concentrated in vacuo. The remaining residue was purified by preparative HPLC (acidic method) to afford 471 mg (89%) of tert-butyl N-[(1S,4R,7R)-2-{2-[1-(cyclopropylmethyl)-1H-pyrrolo[2,3-b]pyridin-2-yl]-7-methoxy-1-methyl-1H-1,3-benzodiazole-5-carbonyl}-6-oxo-2-azabicyclo[2.2.1]heptan-7-yl]carbamate EV-AZ4415-001 as a white solid. LCMS (method D): retention time 1.25 min, M/z=585 (M+1).

Tert-butyl N-[(1S,4R,7R)-6-[benzyl(methyl)amino]-2-{2-[1-(cyclopropylmethyl)-1H-pyrrolo[2,3-b]pyridin-2-yl]-7-methoxy-1-methyl-1H-1,3-benzodiazole-5-carbonyl}-2-azabicyclo[2.2.1]heptan-7-yl] carbamate EV-AZ4411-003—Step 7

A solution of tert-butyl N-[(1S,4R,7R)-2-{2-[1-(cyclopropylmethyl)-1H-pyrrolo[2,3-b]pyridin-2-yl]-7-methoxy-1-methyl-1H-1,3-benzodiazole-5-carbonyl}-6-oxo-2-azabicyclo[2.2.1]heptan-7-yl]carbamate (EV-AZ4415-001, 86%, 109 mg, 0.16 mmol) in DCE (1.5 ml) at room temperature was stirred with activated 3 Å molecular sieves. N-methyl-1-phenylmethanamine (41 µl, 0.32 mmol), sodium triacetoxyborohydride (STAB, 51 mg, 0.24 mmol) and acetic acid (10 µl, 0.17 mmol) were added and the reaction was stirred at room temperature for 72 h. The reaction mixture was filtered and the molecular sieves were washed with DCM (20 ml). The DCM solution was washed with saturated aqueous sodium bicarbonate (15 ml) and the aqueous was re-extracted with DCM (3×15 ml). The combined organics were washed with saturated aqueous sodium chloride (15 ml), dried over magnesium sulfate and concentrated in vacuo. The crude material was dissolved in methanol (5 ml) and loaded on to a 2 g SCX-II cartridge. The cartridge was flushed through with methanol and 2.8 M ammonia in methanol. The relevant fractions were concentrated in vacuo to obtain 71 mg (52%) of tert-butyl N-[(1S,4R,7R)-6-[benzyl(methyl)amino]-2-{2-[1-(cyclopropylmethyl)-1H-pyrrolo[2,3-b]pyridin-2-yl]-7-methoxy-1-methyl-1H-1,3-benzodiazole-5-carbonyl}-2-azabicyclo[2.2.1]heptan-7-yl] carbamate EV-AZ4411-003 as a colourless oil. LCMS (method H): retention time 4.43 min and 4.83 min, M/z=690 (M+1).

Scheme 1.10 Step 7

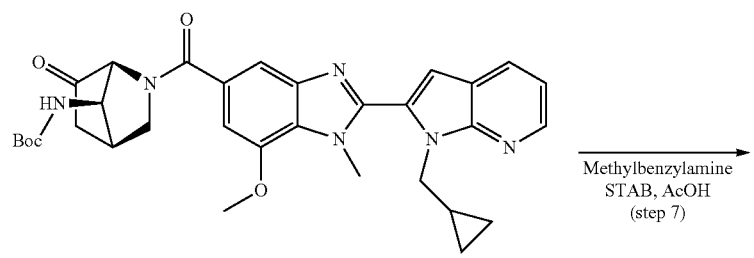

EV-AZ4415-001

Methylbenzylamine
STAB, AcOH
(step 7)

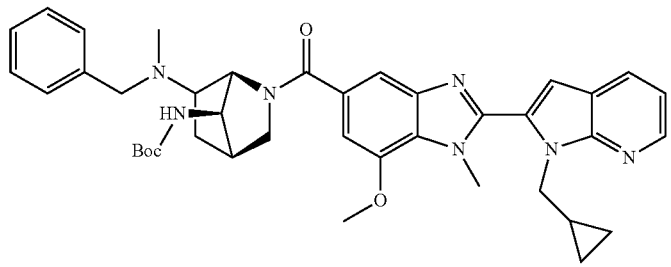

EV-AZ4411-003

Scheme 1.10 Step 8

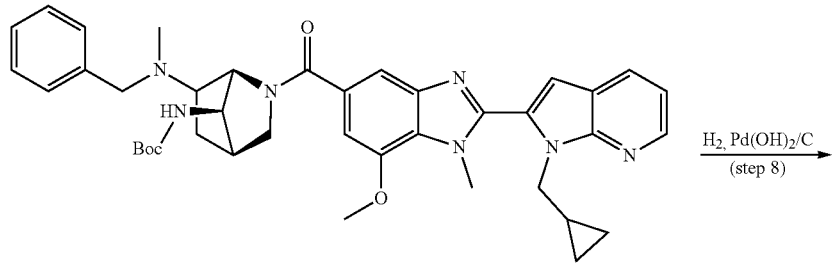

EV-AZ4411-003

EV-AZ4413-002

Tert-butyl N-[(1R,4R,6S,7R)-2-{2-[1-(cyclopropyl-methyl)-1H-pyrrolo[2,3-b]pyridin-2-yl]-7-methoxy-1-methyl-1H-1,3-benzodiazole-5-carbonyl}-6-(methylamino)-2-azabicyclo[2.2.1]heptan-7-yl]carbamate EV-AZ4413-002—Step 8

A solution of 0.05M tert-butyl N-[(1S,4R,6S,7R)-6-[benzyl(methyl)amino]-2-{2-[1-(cyclopropylmethyl)-1H-pyrrolo[2,3-b]pyridin-2-yl]-7-methoxy-1-methyl-1H-1,3-benzodiazole-5-carbonyl}-2-azabicyclo[2.2.1]heptan-7-yl]carbamate (EV-AZ4411-003, 81%, 71 mg, 0.08 mmol) in methanol (2.1 ml) was subjected to H-Cube conditions (1 ml/min, 60 bar, 60° C., 2 passes) over a Pearlman's catalyst (20% Pd(OH)$_2$/C) cartridge. The resulting solution was concentrated in vacuo to obtain 45 mg (60%) of tert-butyl N-[(1R,4R,6S,7R)-2-{2-[1-(cyclopropylmethyl)-1H-pyrrolo[2,3-b]pyridin-2-yl]-7-methoxy-1-methyl-1H-1,3-benzodiazole-5-carbonyl}-6-(methylamino)-2-azabicyclo[2.2.1]heptan-7-yl]carbamate EV-AZ4413-002 as a yellow oil. LCMS (method D): retention time 1.08 min, M/z=600 (M+1).

Scheme 1.10 Step 9

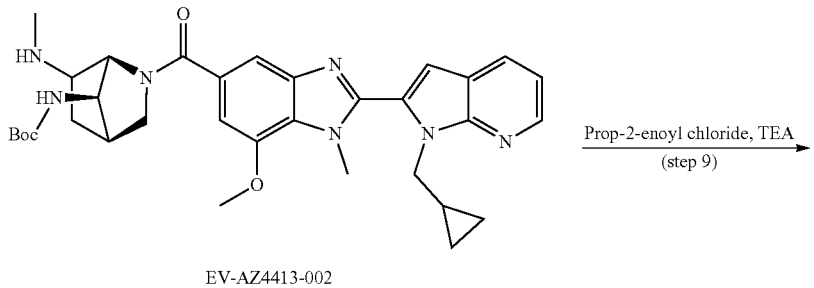

EV-AZ4413-002

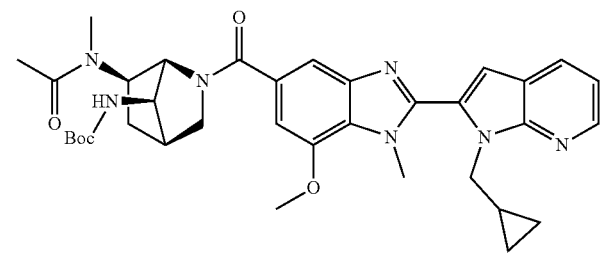

EV-AZ4414-002

119

Tert-butyl N-[(1S,4R,6R,7R)-2-{2-[1-(cyclopropylmethyl)-1H-pyrrolo[2,3-b]pyridin-2-yl]-7-methoxy-1-methyl-1H-1,3-benzodiazole-5-carbonyl}-6-(N-methylprop-2-enamido)-2-azabicyclo[2.2.1]heptan-7-yl]carbamate EV-AZ4414-002 and tert-butyl N-[(1S,4R,6S,7R)-2-{2-[1-(cyclopropylmethyl)-1H-pyrrolo[2,3-b]pyridin-2-yl]-7-methoxy-1-methyl-1H-1,3-benzodiazole-5-carbonyl}-6-(N-methylprop-2-enamido)-2-azabicyclo[2.2.1]heptan-7-yl] carbamate EV-AZ4414-003—Step 9

To a solution of tert-butyl N-[(1R,4R,6S,7R)-2-{2-[1-(cyclopropylmethyl)-1H-pyrrolo[2,3-b]pyridin-2-yl]-7-methoxy-1-methyl-1H-1,3-benzodiazole-5-carbonyl}-6-(methylamino)-2-azabicyclo[2.2.1]heptan-7-yl]carbamate (EV-AZ4413-002, 67%, 45 mg, 0.05 mmol) in dioxane (0.5 ml) was added triethylamine (14 µl, 0.1 mmol) followed by prop-2-enoyl chloride (9 µl, 0.11 mmol). The reaction mixture was stirred at room temperature for 50 minutes. Additional prop-2-enoyl chloride (5 ul) was added to the reaction and stirring was continued for an additional 1.5 h. The resulting reaction mixture was concentrated in vacuo and purified by preparative HPLC (acidic method) to obtain 14 mg (37%) of tert-butyl N-[(1S,4R,6R,7R)-2-{2-[1-(cyclopropylmethyl)-1H-pyrrolo[2,3-b]pyridin-2-yl]-7-methoxy-1-methyl-1H-1,3-benzodiazole-5-carbonyl}-6-(N-methylprop-2-enamido)-2-azabicyclo[2.2.1]heptan-7-yl]carbamate EV-AZ4414-002 (chirality arbitrarily assigned) as a white solid. LCMS (method A): retention time 3.19 min, M/z=654 (M+1). 4.4 mg (12%) of tert-butyl N-[(1S,4R,6S,7R)-2-{2-[1-(cyclopropylmethyl)-1H-pyrrolo[2,3-b]pyridin-2-yl]-7-methoxy-1-methyl-1H-1,3-benzodiazole-5-carbonyl}-6-(N-methylprop-2-enamido)-2-azabicyclo[2.2.1]heptan-7-yl] carbamate EV-AZ4414-003 (chirality arbitrarily assigned) were also isolated as a white solid. LCMS (method A): retention time 3.29 min, M/z=654 (M+1).

Scheme 1.10 Step 10

I-16

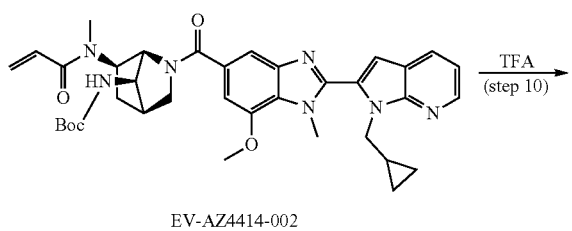

EV-AZ4414-002

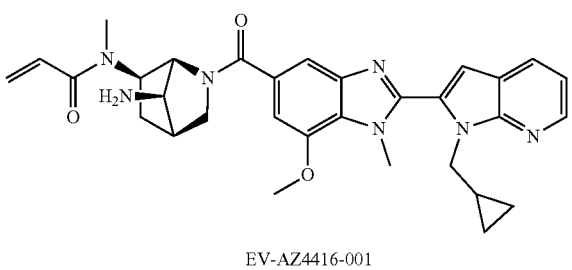

EV-AZ4416-001

-continued

I-17

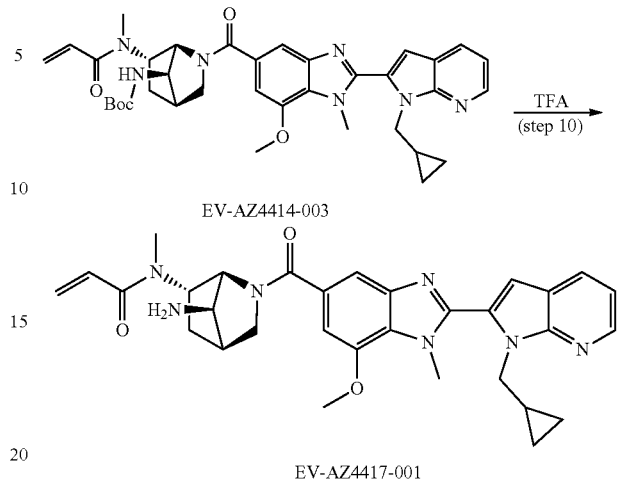

EV-AZ4414-003

EV-AZ4417-001

N-[(1S,4R,6R,7R)-7-Amino-2-{2-[1-(cyclopropylmethyl)-1H-pyrrolo[2,3-b]pyridin-2-yl]-7-methoxy-1-methyl-1H-1,3-benzodiazole-5-carbonyl}-2-azabicyclo[2.2.1]heptan-6-yl]-N-methylprop-2-enamide; trifluoroacetic acid 1-16 (EV-AZ4416-001) (EOAI3478697)—Step 10

To a stirred solution of tert-butyl N-[(1S,4R,6R,7R)-2-{2-[1-(cyclopropylmethyl)-1H-pyrrolo[2,3-b]pyridin-2-yl]-7-methoxy-1-methyl-1H-1,3-benzodiazole-5-carbonyl}-6-(N-methylprop-2-enamido)-2-azabicyclo[2.2.1]heptan-7-yl]carbamate (EV-AZ4414-002, 14 mg, 0.02 mmol) in DCM (0.5 ml) was added TFA (20 µl, 0.26 mmol). The reaction was stirred at room temperature for 0.5 h. Additional TFA (80 µl, 1.04 mmol) was added and the reaction was continued for 1 h. The reaction mixture was concentrated in vacuo, re-dissolved in water and dried by lyophilization to afford 12 mg (78%) of N-[(1S,4R,6R,7R)-7-amino-2-{2-[1-(cyclopropylmethyl)-1H-pyrrolo[2,3-b]pyridin-2-yl]-7-methoxy-1-methyl-1H-1,3-benzodiazole-5-carbonyl}-2-azabicyclo[2.2.1]heptan-6-yl]-N-methylprop-2-enamide; trifluoroacetic acid 1-16 (EV-AZ4416-001) (EOAI3478697) as a white solid. LCMS (method H): retention time 1.93 min, M/z=554 (M+1).

N-[(1S,4R,6S,7R)-7-amino-2-{2-[1-(cyclopropylmethyl)-1H-pyrrolo[2,3-b]pyridin-2-yl]-7-methoxy-1-methyl-1H-1,3-benzodiazole-5-carbonyl}-2-azabicyclo[2.2.1]heptan-6-yl]-N-methylprop-2-enamide; Trifluoroacetic Acid 1-17 (EV-AZ4417-001) (EOAI3478698)—Step 10

To a stirred solution of tert-butyl N-[(1S,4R,6S,7R)-2-{2-[1-(cyclopropylmethyl)-1H-pyrrolo[2,3-b]pyridin-2-yl]-7-methoxy-1-methyl-1H-1,3-benzodiazole-5-carbonyl}-6-(N-methylprop-2-enamido)-2-azabicyclo[2.2.1]heptan-7-yl]carbamate (EV-AZ4414-003, 92%, 4.4 mg, 0.01 mmol) in DCM (0.4 ml) was added TFA (29 µl, 0.38 mmol). The reaction was stirred at room temperature for 2 h. Additional TFA (20 µl, 0.26 mmol) was added and the reaction was continued for 30 minutes. The reaction mixture was concentrated in vacuo, re-dissolved in water and dried by lyophilization to afford 5 mg (quantitative) of N-[(1S,4R, 6S,7R)-7-amino-2-{2-[1-(cyclopropylmethyl)-1H-pyrrolo[2,3-b]pyridin-2-yl]-7-methoxy-1-methyl-1H-1,3-benzodiazole-5-carbonyl}-2-azabicyclo[2.2.1]heptan-6-yl]-N-methylprop-2-enamide; trifluoroacetic acid 1-17 (EV-AZ4417-001) (EOAI3478698) as a sticky white solid. LCMS (method A): retention time 2.10 min, M/z=554 (M+1).

Example 15. Synthesis of (1S,4R,6S,7R)-7-amino-2-{2-[1-(cyclopropylmethyl)-1H-pyrrolo[2,3-b]pyridin-2-yl]-7-methoxy-1-methyl-1H-1,3-benzodiazole-5-carbonyl}-2-azabicyclo[2.2.1]heptan-6-yl prop-2-enoate, I-15

(1S,4R,6S,7R)-7-amino-2-{2-[1-(cyclopropylmethyl)-1H-pyrrolo[2,3-b]pyridin-2-yl]-7-methoxy-1-methyl-1H-1,3-benzodiazole-5-carbonyl}-2-azabicyclo[2.2.1]heptan-6-yl prop-2-enoate I-15 (EV-AY5035-001) (EOAI3470264) LCMS (method A): retention time 2.23 min, M/z=541.3 (M+1) was synthesised according to the procedures described in Scheme 1 via synthesis of (1S,4R,6S,7R)-7-{[(tert-butoxy)carbonyl]amino}-2-{2-[1-(cyclopropylmethyl)-1H-pyrrolo[2,3-b]pyridin-2-yl]-7-methoxy-1-methyl-1H-1,3-benzodiazole-5-carbonyl}-2-azabicyclo[2.2.1]heptan-6-yl prop-2-enoate EV-AY5034-002 described in Scheme 1.10, step 11.

2-enoyl chloride (20 μl, 0.25 mmol). The reaction mixture was allowed to warm to room temperature and stirred for 1 h. Triethylamine (70 μl, 0.51 mmol) was added followed by prop-2-enoyl chloride (40 μl, 0.50 mmol). The mixture was stirred at room temperature for 30 minutes. The reaction was quenched using saturated aqueous ammonium chloride (25 ml) and extracted using DCM (3×25 ml). The organic extracts were combined, dried over magnesium sulfate and concentrated in vacuo. The crude product was purified by flash column chromatography (20-100% EtOAc/heptane) and by preparative HPLC (acidic method) to obtain 6 mg (18%) of (1S,4R,6S,7R)-7-{[(tert-butoxy)carbonyl]amino}-2-{2-[1-(cyclopropylmethyl)-1H-pyrrolo[2,3-b]pyridin-2-yl]-7-methoxy-1-methyl-1H-1,3-benzodiazole-5-carbonyl}-2-azabicyclo[2.2.1]heptan-6-yl prop-2-enoate EV-AY5034-002 as a white powder. LCMS (method D): retention time 1.25 min, M/z=641 (M+1).

Example 16. Synthesis of N-[(1S,4R,6S,7R)-7-amino-2-{2-[1-(cyclopropylmethyl)-1H-pyrrolo[2,3-b]pyridin-2-yl]-7-methoxy-1-methyl-1H-1,3-benzodiazole-5-carbonyl}-2-azabicyclo[2.2.1]heptan-6-yl]prop-2-enamide, I-14

N-[(1S,4R,6S,7R)-7-amino-2-{2-[1-(cyclopropylmethyl)-1H-pyrrolo[2,3-b]pyridin-2-yl]-7-methoxy-1-

Scheme 1.10 Step 11

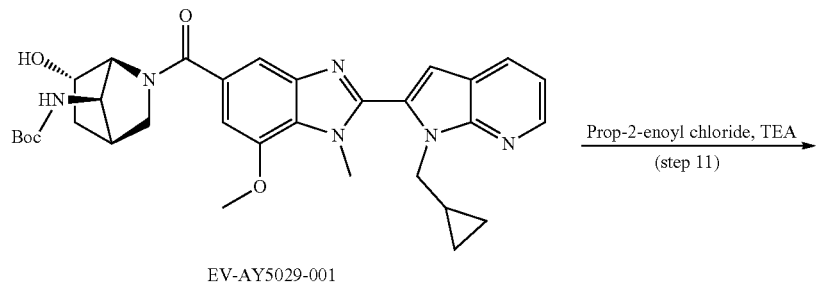

EV-AY5029-001

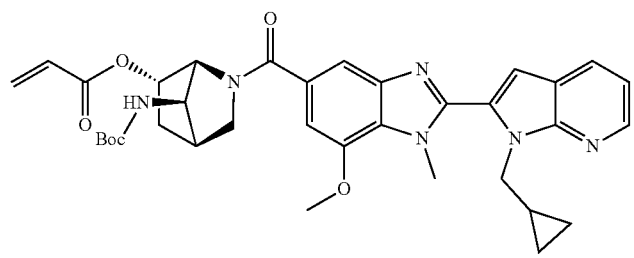

EV-AY5034-002

(1S,4R,6S,7R)-7-{[(Tert-butoxy)carbonyl]amino}-2-{2-[1-(cyclopropylmethyl)-1H-pyrrolo[2,3-b]pyridin-2-yl]-7-methoxy-1-methyl-1H-1,3-benzodiazole-5-carbonyl}-2-azabicyclo[2.2.1]heptan-6-yl prop-2-enoate (EV-AY5034-001)—Step 11

To a cold solution (0° C.) of tert-butyl N-[(1S,4R,6S,7R)-2-{2-[1-(cyclopropylmethyl)-1H-pyrrolo[2,3-b]pyridin-2-yl]-7-methoxy-1-methyl-1H-1,3-benzodiazole-5-carbonyl}-6-hydroxy-2-azabicyclo[2.2.1]heptan-7-yl]carbamate (EV-AY5029-001, 120 mg, 0.20 mmol) in DCM (2 ml) was added triethylamine (70 μl, 0.51 mmol) followed by propmethyl-1H-1,3-benzodiazole-5-carbonyl}-2-azabicyclo[2.2.1]heptan-6-yl]prop-2-enamide 1-14 (EV-AY4929-001) (EOAI3470263) LCMS (method A): retention time 2.07 min, M/z=540.3 (M+1) was synthesised according to procedures described in Scheme 1 via synthesis of tert-butyl N-[(1R,4R,6S,7R)-2-{2-[1-(cyclopropylmethyl)-1H-pyrrolo[2,3-b]pyridin-2-yl]-7-methoxy-1-methyl-1H-1,3-benzodiazole-5-carbonyl}-6-(prop-2-enamido)-2-azabicyclo[2.2.1]heptan-7-yl]carbamate EV-AW8586-002 described in Scheme 1.10, steps 12-14.

Scheme 1.10 Step 12

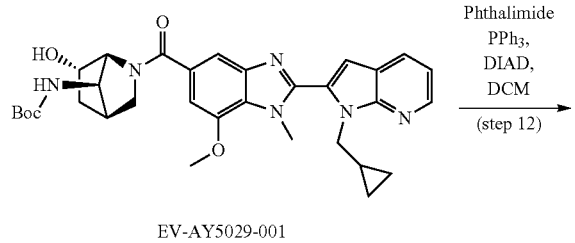

EV-AY5029-001

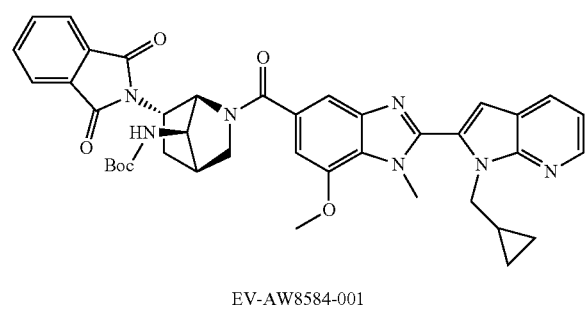

EV-AW8584-001

Tert-butyl N-[(1S,4R,6S,7R)-2-{2-[1-(cyclopropyl-methyl)-1H-pyrrolo[2,3-b]pyridin-2-yl]-7-methoxy-1-methyl-1H-1,3-benzodiazole-5-carbonyl}-6-(1,3-dioxo-2,3-dihydro-1H-isoindol-2-yl)-2-azabicyclo[2.2.1]heptan-7-yl]carbamate EV-AW8584-001—Step 12

DIAD (107 μl, 0.51 mmol) was added to a stirred solution of triphenylphosphane (134 mg, 0.51 mmol) in anhydrous THF (5 ml) under an atmosphere of nitrogen at 0° C. The reaction was stirred at 0° C. for 5 minutes then a solution of tert-butyl N-[(1S,4R,6S,7R)-2-{2-[1-(cyclopropylmethyl)-1H-pyrrolo[2,3-b]pyridin-2-yl]-7-methoxy-1-methyl-1H-1,3-benzodiazole-5-carbonyl}-6-hydroxy-2-azabicyclo[2.2.1]heptan-7-yl]carbamate (EV-AY5029-001, 200 mg, 0.34 mmol) in anhydrous THF (5 ml) was added followed by 1H-isoindole-1,3(2H)-dione (41 μl, 0.34 mmol). The reaction mixture was stirred at room temperature for 18 h, concentrated in vacuo and purified by flash column chromatography (0-100% EtOAc/heptane) to obtain 138 mg (48%) of tert-butyl N-[(1S,4R,6S,7R)-2-{2-[1-(cyclopropylmethyl)-1H-pyrrolo[2,3-b]pyridin-2-yl]-7-methoxy-1-methyl-1H-1,3-benzodiazole-5-carbonyl}-6-(1,3-dioxo-2,3-dihydro-1H-isoindol-2-yl)-2-azabicyclo[2.2.1]heptan-7-yl]carbamate EV-AW8584-001 as a white foam. LCMS (method D): retention time 1.28 min, M/z=716 (M+1).

Scheme 1.10 Step 13

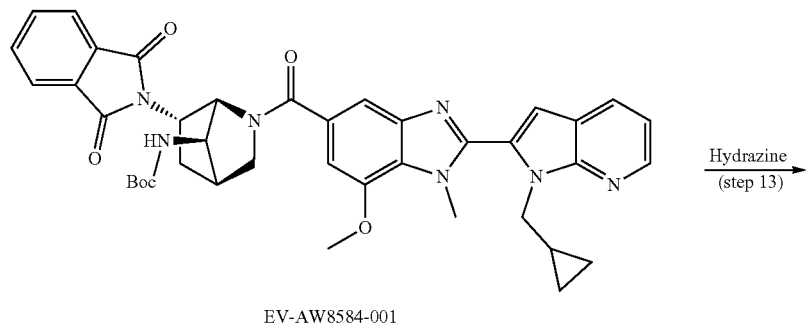

EV-AW8584-001

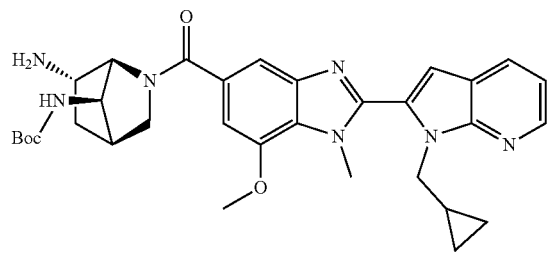

EV-AW8585-005

Tert-butyl N-[(1R,4R,6S,7R)-6-amino-2-{2-[1-(cyclopropylmethyl)-1H-pyrrolo[2,3-b]pyridin-2-yl]-7-methoxy-1-methyl-1H-1,3-benzodiazole-5-carbonyl}-2-azabicyclo[2.2.1]heptan-7-yl]carbamate EV-AW8585-005—Step 13

To a solution of tert-butyl N-[(1S,4R,6S,7R)-2-{2-[1-(cyclopropylmethyl)-1H-pyrrolo[2,3-b]pyridin-2-yl]-7-methoxy-1-methyl-1H-1,3-benzodiazole-5-carbonyl}-6-(1,3-dioxo-2,3-dihydro-1H-isoindol-2-yl)-2-azabicyclo[2.2.1]heptan-7-yl]carbamate (EV-AW8584-001, 134 mg, 0.19 mmol) in DCM (3 ml) was added hydrazine hydrate (1:1) (27 μl, 0.56 mmol). The reaction mixture was stirred at room temperature for 45 minutes and at 50° C. for 18 h, filtered and the filtrate was concentrated in vacuo. EtOAc (10 ml) was added to the residue and the mixture was stirred for 5 minutes then filtered. The filtrate was concentrated in vacuo and purified by flash column chromatography (20-100% EtOAc/heptane) to obtain 75 mg (63%) of tert-butyl N-[(1R,4R,6S,7R)-6-amino-2-{2-[1-(cyclopropylmethyl)-1H-pyrrolo[2,3-b]pyridin-2-yl]-7-methoxy-1-methyl-1H-1,3-benzodiazole-5-carbonyl}-2-azabicyclo[2.2.1]heptan-7-yl]carbamate EV-AW8585-005 as a white foam. LCMS (method D): retention time 1.05 min, M/z=586 (M+1).

N-[(1R,4R,6S,7R)-2-{2-[1-(cyclopropylmethyl)-1H-pyrrolo[2,3-b]pyridin-2-yl]-7-methoxy-1-methyl-1H-1,3-benzodiazole-5-carbonyl}-6-(prop-2-enamido)-2-azabicyclo[2.2.1]heptan-7-yl]carbamate EV-AW8586-002 as a white solid. LCMS (method A): retention time 3.13 min, M/z=640 (M+1).

Biological Assays

Example 17. PAD4 RapidFire Mass Spectrometry (RFMS) Activity Assay

Compounds of the present invention were assayed as inhibitors of PAD4 using the assay protocol described below.

Compounds were solubilized in 100% DMSO to achieve 100 mM final compound concentration. Compound stock solutions were stored at RT. A series of dilutions were prepared in DMSO and mixed 8 times with 20 μL mixing volume. Final assay conditions were as follows:

Reaction volume: 20 μl
Assay buffer (as aforementioned): 100 mM Tris-HCl (pH 7.6), 2 mM DTT, 1 mM $CaCl_2$

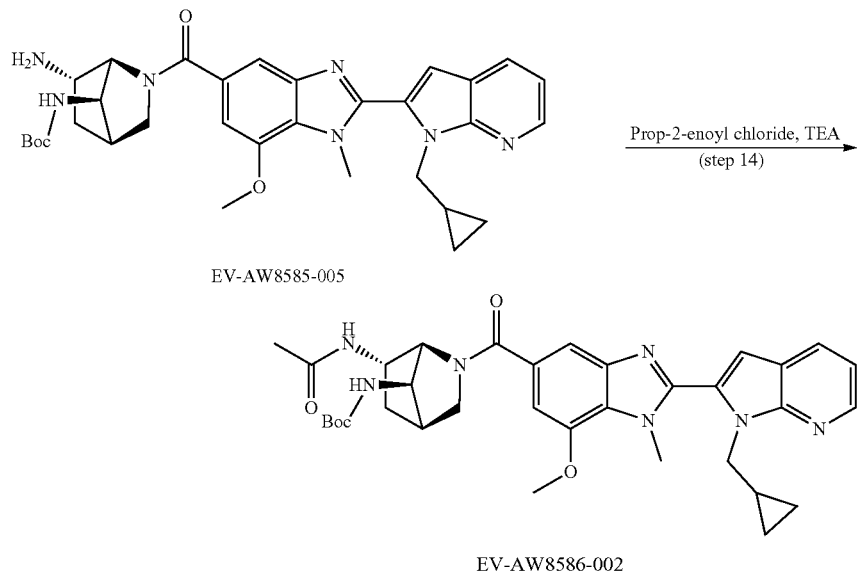

Scheme 1.10 Step 14

EV-AW8585-005

Prop-2-enoyl chloride, TEA
(step 14)

EV-AW8586-002

Tert-butyl N-[(1R,4R,6S,7R)-2-{2-[1-(cyclopropylmethyl)-1H-pyrrolo[2,3-b]pyridin-2-yl]-7-methoxy-1-methyl-1H-1,3-benzodiazole-5-carbonyl}-6-(prop-2-enamido)-2-azabicyclo[2.2.1]heptan-7-yl]carbamate EV-AW8586-002—Step 14

To a solution of tert-butyl N-[(1R,4R,6S,7R)-6-amino-2-{2-[1-(cyclopropylmethyl)-1H-pyrrolo[2,3-b]pyridin-2-yl]-7-methoxy-1-methyl-1H-1,3-benzodiazole-5-carbonyl}-2-azabicyclo[2.2.1]heptan-7-yl]carbamate (EV-AW8585-005, 92%, 75 mg, 0.12 mmol) in dioxane (2 ml) was added triethylamine (18 μl, 0.13 mmol) followed by prop-2-enoyl chloride (10 μl, 0.13 mmol). The reaction mixture was stirred at room temperature for 30 minutes, concentrated in vacuo and the resulting residue was purified by preparative HPLC (acidic method) to obtain 44 mg (59%) of tert-butyl Final concentrations:
  100 nM hPAD4 enzyme
  50 μM (8-fold sub-$K_m$) substrate peptide
  0.5% DMSO
Total incubation time: 65 mins at 37° C.
Stop solution: 40 μl 5% TCA in ACN 0.25 μL of compound solution was added to 10 μL of 200 nM PAD4 in assay buffer (100 mM Tris-HCl pH 7.6, 2 mM DTT). After 5 mins, 10 μL of 100 μM of substrate in buffer (100 mM Tris-HCl pH 7.6, 2 mM DTT, 2 mM $CaCl_2$) was added and the reaction incubated for 60 mins at 37° C. The enzymatic reaction was quenched by addition of 40 μl of 5% TCA in ACN (1.7% TCA final concentration) stop solution. Arginine containing substrate and citrulline containing product (+1 Da mass shift) were subjected to solid phase extraction on Agilent RapidFire (RF) 300 system and detected on a coupled, triple quadrupole Agilent 6460 QQQ mass spectrometry (MS) device under application of multiple reaction monitoring (MRM) for quantitation.

Table 2, below, shows the activity of selected compounds of this invention in the PAD4 assays described above. The compound numbers correspond to the compound numbers in Table 1. Compounds having an activity designated as "A" provided an $IC_{50}$ of 0.1-1 µM; compounds having an activity designated as "B" provided an $IC_{50}$ of 1-5 µM; compounds having an activity designated as "C" provided an $IC_{50}$ of 5-10 µM; and compounds having an activity designated as "D" provided an $IC_{50}$ of >10 µM. The term $pIC_{50}=-\log (IC_{50})$. Compounds having an activity designated as "E" provided a $pIC_{50}$ of 1-4; compounds having an activity designated as "F" provided a $pIC_{50}$ of 4-5; and compounds having an activity designated as "G" provided a $pIC_{50}$ of >5. "NA" stands for "not assayed."

Example 18. Covalent Modification Study Using MS (Mass Spectrometry)

Mass spectrometry was used to analyze covalent modification of protein by selected inhibitors. Recombinant human PAD4 was used at 4 mg/ml in 20 mM Tris pH7.6, 400 mM NaCl, 5 mM TCEP. Where applicable, buffer was supplemented with 5 mM $CaCl_2$) to determine Calcium sensitivity of modification. Inhibitors were dissolved in DMSO at final concentrations of 0.2 mM to 5 mM and incubated with protein at 27° C. for 16 hours prior to analysis. Control experiments were performed with protein and DMSO in absence of inhibitor. Samples were centrifuged for 15 seconds at 10000 rpm at room temperature immediately prior to analysis using a Waters LCT-Premier TOF mass spectrometer, using a mobile phase from 5% to 80% acetonitrile in water supplemented by 0.1% formic acid.

Example 19. Inactivation Kinetics

Covalent binding of an active compound to the target enzyme leads to time dependent loss of the enzyme activity. The rate of inactivation depends on the inhibitor concentration ([I]) and can be quantified under pseudo-first order conditions ([I]>>[hPAD4]).

Inactivation kinetics experiments were performed in 384-well polystyrene plates at 37° C. Compounds (10-200 µM) and hPAD4 (4 µM) solutions were pre-incubated in assay buffer (100 mM Tris-HCl, pH 7.6) containing 10 mM $CaCl_2$ and 2 mM DTT for 10 minutes to reach a temperature of 37° C. Equal volumes (10 µl) of compound and hPAD4 solutions were mixed at various time points between 0 and 70 minutes. At 70 minutes time point, the inactivation solution was diluted 10-fold in enzymatic reaction buffer (100 mM Tris-HCl, pH 7.6) containing 166.7 µM peptide substrate (H-TSTGGRQGSHH-$CONH_2$), 1.1 mM $CaCl_2$ and 2 mM DTT. After 30 minutes of incubation at 37° C. the enzymatic reaction was quenched by 3-fold dilution in 5% TCA solution in ACN. Substrate peptide arginine citrullination was determined by solid phase extraction mass spectrometry (SPE-MS). An Agilent RapidFire 300 equipped with a HILIC (H1) cartridge was used for sampling with solvents 0.1% TFA in $H_2O$/ACN (20/80) for P1 and 0.1% TFA in $H_2O$/ACN (50/50) for P2 and P3. Substrate and product peptide were detected using a coupled Agilent 6460 QQQ and multiple reaction monitoring (MRM) on transitions 562.3/969.4 and 562.8/541, respectively, in positive ion mode. DMSO content of the inactivation reaction was 1%. Cl-amidine (100 mM, final concentration during enzyme inactivation reaction) and 1% DMSO were used as positive and negative controls of the inactivation reaction, respectively.

Pseudo-first order rate constants of inactivation reaction, $k_{obs}$, were determined by fitting the time dependent loss of residual hPAD4 activity, $A_{res}$, with equation: $A_{res}(t)=e^{-kobs*t}$. A plot of the pseudo-first order rate constants versus molar concentrations of the inhibitors allowed determination of the kinetic reaction constants: $k_{inact}$—maximum rate of inactivation at infinite [I]; $K_I$—inhibitor concentration, at which rate of inactivation is equal to $½k_{inact}$; $k_{inact}/K_I$.

Certain compounds of the present invention were assayed according to the procedures described above and were found to covalently modify PAD4.

Table 3, below, shows the activity of selected compounds of this invention in the covalent modification assay described above. The compound numbers correspond to the compound numbers in Table 1.

TABLE 2

| | PAD4 Activity | | | |
|---|---|---|---|---|
| Compound # | hPAD4 RFMS $IC_{50}$ µM | hPAD4 RFMS $pIC_{50}$ | mPAD4 RFMS $IC_{50}$ µM | mPAD4 RFMS $pIC_{50}$ |
| I-1 | B | G | B | G |
| I-2 | A | G | A | G |
| I-3 | D | E | D | F |
| I-4 | D | F | D | F |
| I-5 | B | G | A | G |
| I-6 | D | E | NA | NA |
| I-7 | D | E | NA | NA |
| I-8 | C | G | C | F |
| I-9 | B | G | A | G |
| I-10 | D | F | D | F |
| I-11 | D | F | NA | NA |
| I-12 | D | F | NA | NA |
| I-13 | D | E | NA | NA |
| I-14 | B | G | A | G |
| I-15 | A | G | NA | NA |
| I-16 | D | E | NA | NA |
| I-17 | D | E | NA | NA |

TABLE 3

| Covalent Modification Study: Inactivation Kinetics* | | | |
|---|---|---|---|
| Compound # | $k_{inact}$ ($min^{-1}$) | $K_i$ (µM) | $k_{inact}/K_i$ ($min^{-1}M^{-1}$) |
| I-1 | 0.3414 | 182.3 | 1872 |
| I-2 | 0.6469 | 89.9 | 7801 |
| I-5 | 0.9225 | 181.4 | 5085 |
| I-8 | 0.0563 | 39.63 | 1420 |
| I-9 | 0.368 | 165 | 2231 |

*hPAD4 isoform; $Ca^{++}$ concentration = 10 mM

We claim:
1. A compound of formula I

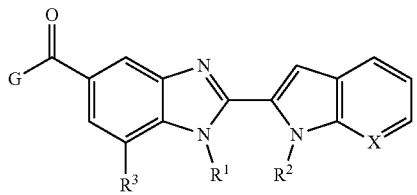

or a pharmaceutically acceptable salt thereof, wherein:
G is

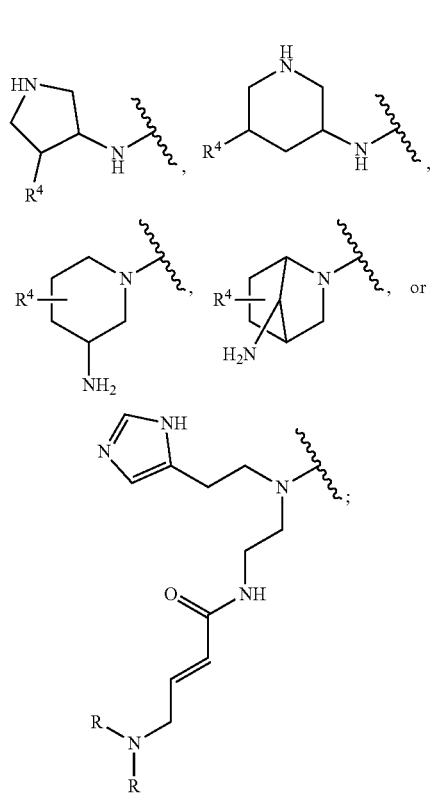

each R⁴ is independently selected from

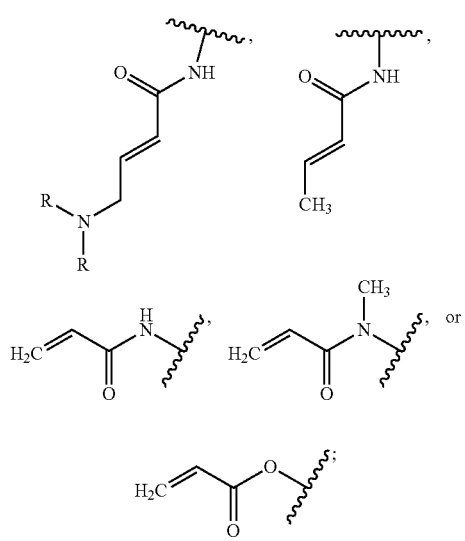

R¹ is hydrogen or $C_{1-6}$ aliphatic;
R² is hydrogen or $C_{1-10}$ aliphatic;
X is selected from N or CH;
R³ is R, or OR; and
each R is independently hydrogen or $C_{1-6}$ aliphatic optionally substituted with 1-3 fluorine atoms.

2. The compound according to claim 1, wherein G is

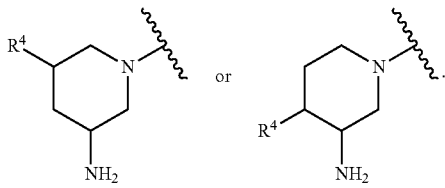

3. The compound according to claim 1, wherein G is

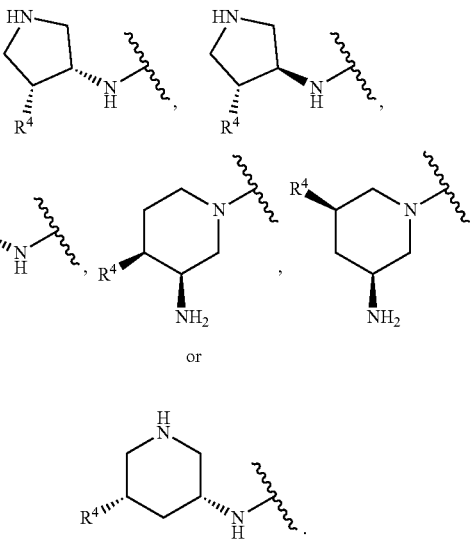

4. The compound according to claim 1, wherein G is selected from

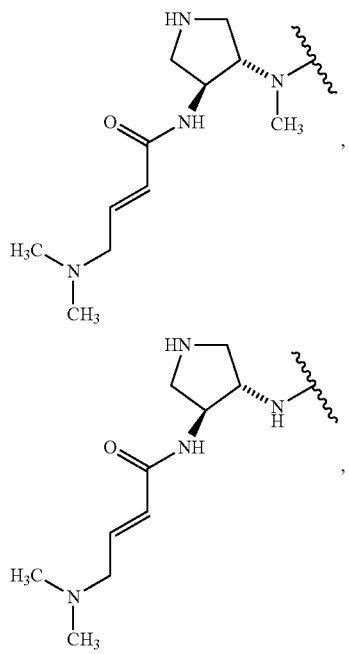

131
-continued

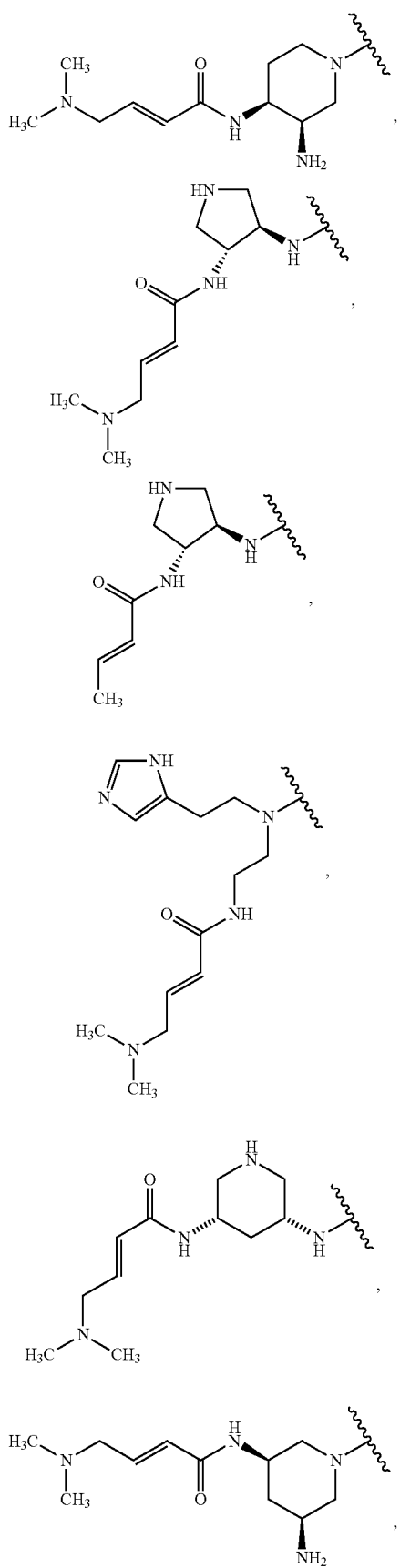

132
-continued

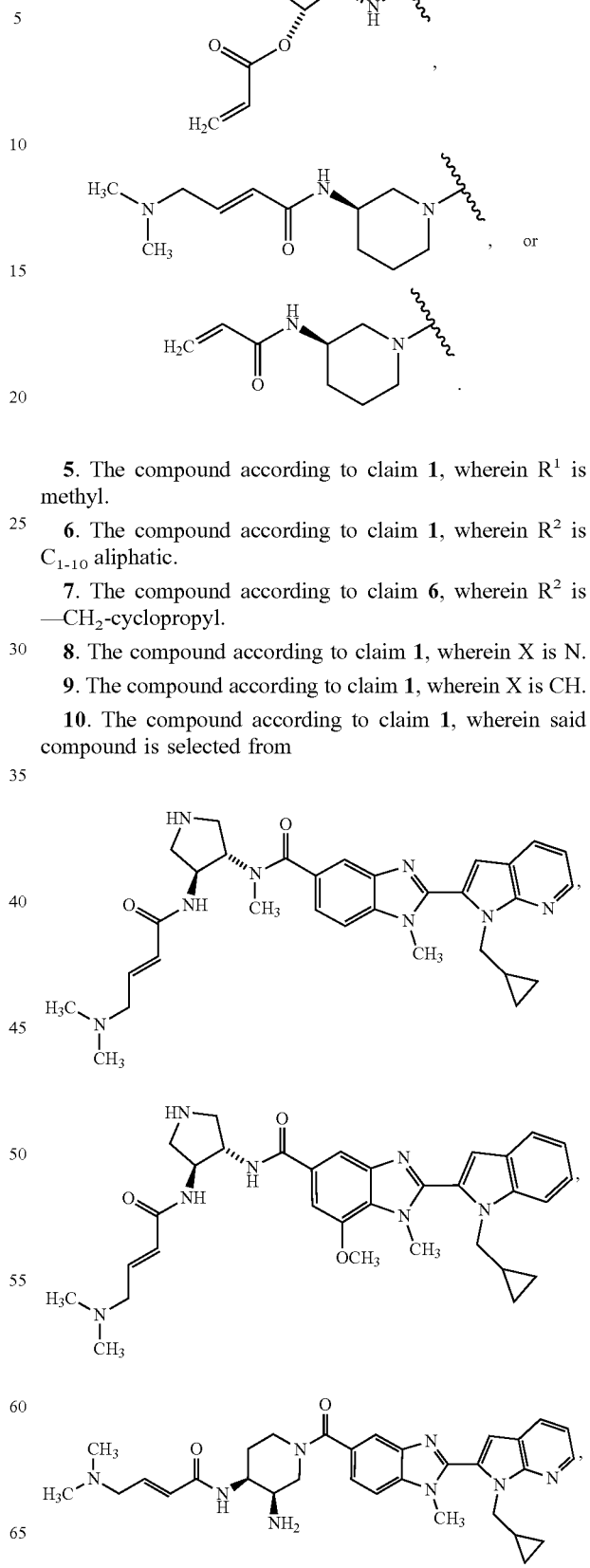

5. The compound according to claim 1, wherein $R^1$ is methyl.

6. The compound according to claim 1, wherein $R^2$ is $C_{1-10}$ aliphatic.

7. The compound according to claim 6, wherein $R^2$ is —$CH_2$-cyclopropyl.

8. The compound according to claim 1, wherein X is N.

9. The compound according to claim 1, wherein X is CH.

10. The compound according to claim 1, wherein said compound is selected from

133
-continued
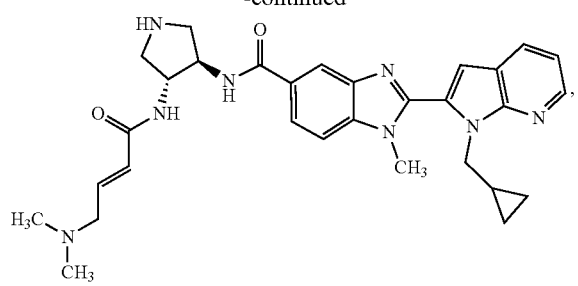
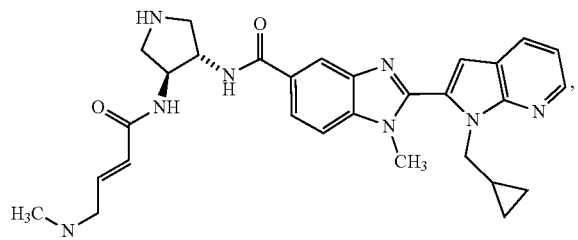
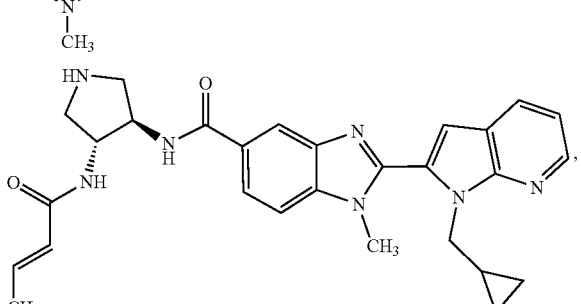
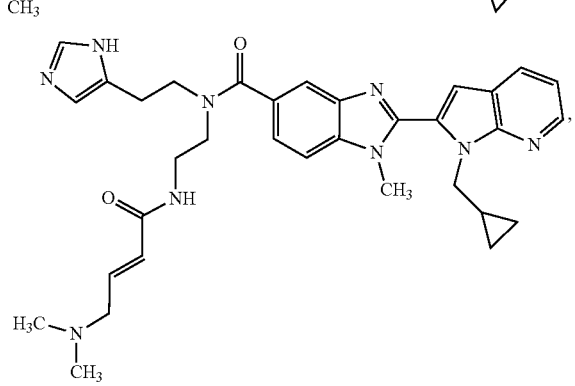
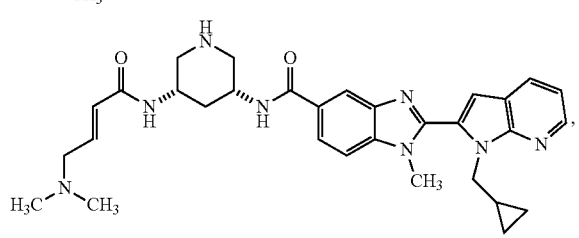
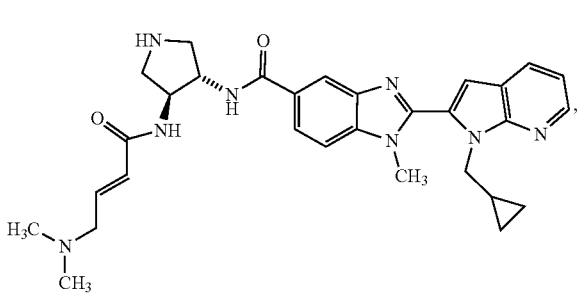
134
-continued
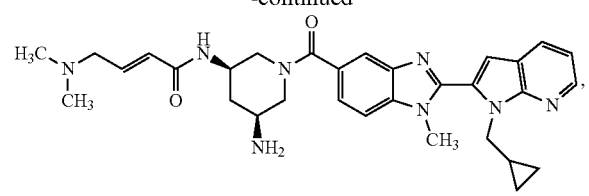
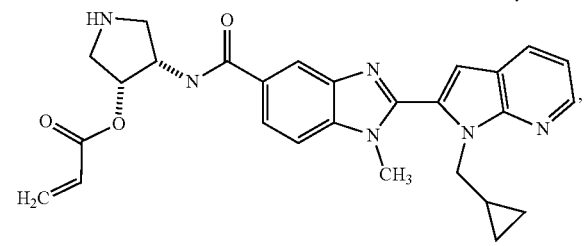
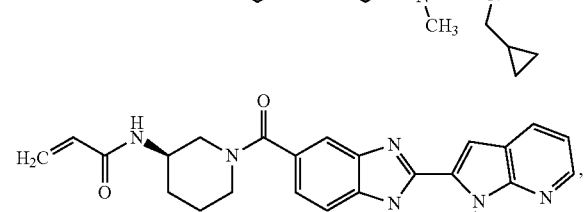
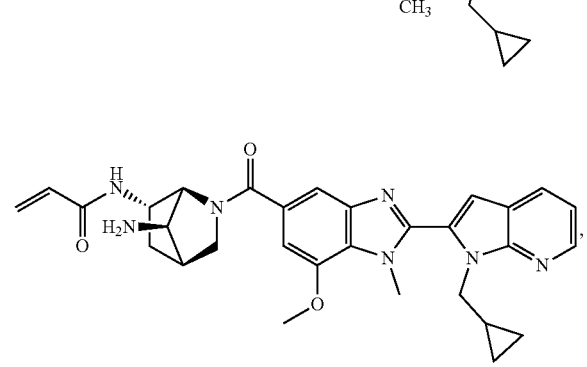
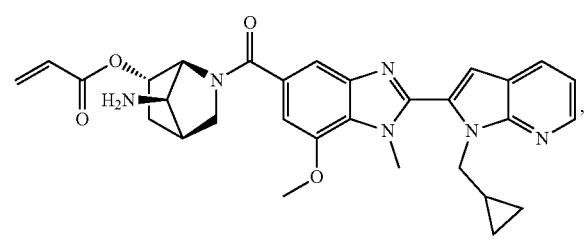
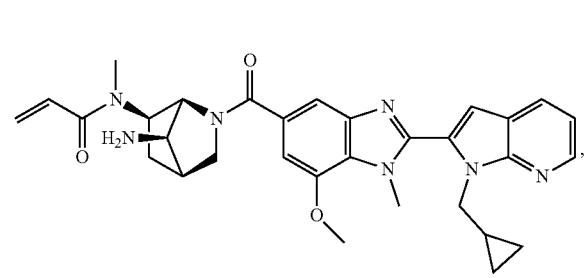

-continued

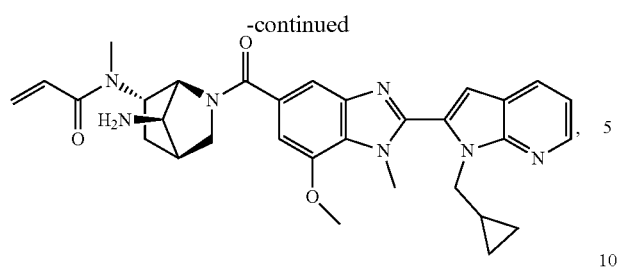

or a pharmaceutically acceptable salt thereof.

11. A pharmaceutically acceptable composition comprising the compound according to claim 1, and a pharmaceutically acceptable carrier, adjuvant, or vehicle.

12. The composition according to claim 11, in combination with an additional therapeutic agent.

13. A method of inhibiting PAD4 in a subject or in a biological sample comprising the step of contacting the PAD4 with a compound according to claim 1.

* * * * *